(12) United States Patent
Cohen et al.

(10) Patent No.: US 8,110,568 B2
(45) Date of Patent: Feb. 7, 2012

(54) INHIBITORS OF IAP

(75) Inventors: Frederick Cohen, San Francisco, CA (US); Kurt Deshayes, San Francisco, CA (US); Wayne J. Fairbrother, Burlingame, CA (US); Bainian Feng, Foster City, CA (US); John A. Flygare, Burlingame, CA (US); Lewis J. Gazzard, Belmont, CA (US); Vickie Hsiao-Wei Tsui, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 12/727,218

(22) Filed: Mar. 18, 2010

(65) Prior Publication Data

US 2010/0256115 A1 Oct. 7, 2010

Related U.S. Application Data

(63) Continuation of application No. 11/739,030, filed on Apr. 23, 2007, now abandoned, which is a continuation of application No. 11/174,784, filed on Jul. 5, 2005, now Pat. No. 7,244,851.

(60) Provisional application No. 60/585,501, filed on Jul. 2, 2004.

(51) Int. Cl.
| | |
|---|---|
| A61K 31/55 | (2006.01) |
| A61K 31/4035 | (2006.01) |
| A61K 31/427 | (2006.01) |
| A61K 31/4155 | (2006.01) |
| A61K 31/433 | (2006.01) |
| A61K 31/40 | (2006.01) |
| A61K 31/4192 | (2006.01) |
| A61K 31/42 | (2006.01) |
| A61K 31/41 | (2006.01) |
| A61K 31/4245 | (2006.01) |
| A61K 31/4439 | (2006.01) |
| A61P 35/00 | (2006.01) |

(52) U.S. Cl. .................. 514/212.06; 514/417; 514/365; 514/407; 514/361; 514/427; 514/359; 514/380; 514/381; 514/364; 514/342

(58) Field of Classification Search ........................ None
See application file for complete search history.

(56) References Cited

U.S. PATENT DOCUMENTS

| | | | |
|---|---|---|---|
| 4,149,003 A | 4/1979 | Carlsson et al. | |
| 4,278,793 A | 7/1981 | Durckheimer et al. | |
| 4,720,484 A | 1/1988 | Vincent et al. | |
| 4,837,165 A | 6/1989 | Hawke | |
| 4,935,494 A | 6/1990 | Miller | |
| 5,411,942 A | 5/1995 | Widmer et al. | |
| 5,559,209 A | 9/1996 | Nishimoto | |
| 6,472,172 B1 | 10/2002 | Deng et al. | |
| 6,608,026 B1 | 8/2003 | Wang et al. | |
| 6,992,063 B2 | 1/2006 | Shi | |
| 7,041,784 B2 | 5/2006 | Wang et al. | |
| 7,067,274 B2 | 6/2006 | Fairbrother et al. | |
| 7,244,851 B2 | 7/2007 | Cohen et al. | |
| 2002/0177557 A1 | 11/2002 | Shi | |
| 2003/0157522 A1 | 8/2003 | Boudreault et al. | |
| 2004/0171554 A1 | 9/2004 | Franklin et al. | |
| 2006/0052311 A1 | 3/2006 | Sharma et al. | |

FOREIGN PATENT DOCUMENTS

| | | |
|---|---|---|
| WO | 92/01938 | 2/1992 |
| WO | 94/11026 | 5/1994 |
| WO | WO 00/00823 | 1/2000 |
| WO | WO 00/39585 | 7/2000 |
| WO | 02/16402 A2 | 2/2002 |
| WO | 02/16418 A2 | 2/2002 |
| WO | 02/26775 A2 | 4/2002 |
| WO | 02/30959 A2 | 4/2002 |
| WO | 02/096930 A2 | 12/2002 |
| WO | 03/010184 A2 | 2/2003 |
| WO | 03/086470 A2 | 10/2003 |
| WO | 2004/005248 A1 | 1/2004 |
| WO | 2004/007529 | 1/2004 |
| WO | 2004/017991 A1 | 3/2004 |
| WO | 2004/072641 A1 | 8/2004 |
| WO | WO 2004/106371 A1 | 12/2004 |
| WO | 2005/049853 A2 | 6/2005 |
| WO | 2005/097791 A1 | 10/2005 |
| WO | 2006/020060 A2 | 2/2006 |

OTHER PUBLICATIONS

Arnt et al., "Synthetic Smac/DIABLO Peptides Enhance the Effects of Chemotherapeutic Agents by Binding XIAP and cIAP1 in Situ" *J. Bio. Chem.* 277(46):44236-44243 (Nov. 2002).

(Continued)

*Primary Examiner* — Yong Chu
(74) *Attorney, Agent, or Firm* — Brian L. Buckwalter

(57) ABSTRACT

The invention provides novel inhibitors of IAP that are useful as therapeutic agents for treating malignancies where the compounds have the general formula I:

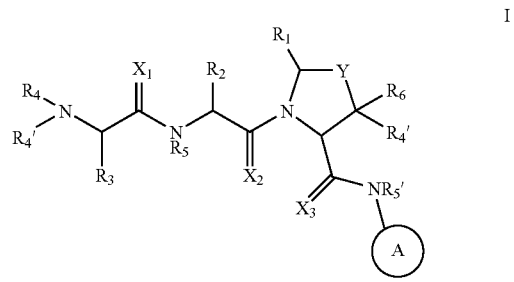

wherein X, Y, A, $R_1$, $R_2$, $R_3$, $R_4$, $R_4'$, $R_5$, $R_5'$, $R_6$ and $R_6'$ are as described herein.

4 Claims, No Drawings

OTHER PUBLICATIONS

Chai Jijie et al., "Structural and biochemical basis of apoptotic activation by SMAC/Diablo" *Nature*, London, GB:Nature Publishing Group vol. 406(6798):855-862 (Aug. 24, 2000).

Chari et al., "Immunoconjugates Containing Novel Maytansinoids: Promising Anticancer Drugs" *Cancer Research* 52:127-131 (Jan. 1992).

Fulda et al., "Smac Agonists Sensitize for Apo2L/TRAIL- or Anticancer Drug-Induced Apoptosis and Induce Regression of Malignant Glioma in Vivo" *Nature Medicine* 8(8):808-815 (Aug. 2002).

Guo et al., "Ectopic Overexpression of Second Mitochondria-Derived Activator of Caspases (Smac/DIABLO) or Cotreatment with N-Terminus of Smac/DIABLO Peptide Potentiates Epothilone B Derivative—(BMS 247550) and Apo-2L/TRAIL-Induced Apoptosis" *Blood* 99:3419-3426 (2002).

Liu et al., "Structural Basis for Binding of Smac/DIABLO to the XIAP BIR3 Domain" *Nature* 408:1004-1008 (Dec. 2000).

Murray, D. et al., "Synthetic peptide substrate for the erythrocyte protein carboxyl methyltransferase" *J Biol. Chem.* 259(17):10722-10732 (1984).

STN-11739030B_09152009, (2009).

Stark, "Sequential degradation of peptides from their carboxyl termini with ammonium thiocyanate and acetic anhydride" *Biochemistry* 7(5):1796-1807 (1968).

Vippagunta, et al., "Crystalline solids" *Advanced Drug Delivery Reviews* 48:3-26 (2001).

Vucic et al., "SMAC Negatively Regulates the Anti-apoptotic Activity of Melanoma Inhibitor of Apoptosis (ML-IAP)" *The Journal of Biological Chemistry* 277:12275-12279 (2002).

Yang et al., "Predominant suppression of apoptosome by inhibitor of apoptosis protein in non-small cell lung cancer H460 cells: therapeutic effect of a novel polyarginine-conjugated smac peptide" *Cancer Research* 63(4):831-837 (2003).

INHIBITORS OF IAP

CROSS REFERENCE TO RELATED APPLICATIONS

This application is a continuation of U.S. patent application Ser. No. 11/739,030, filed on 23 Apr. 2007 now abandoned, which is a continuation of U.S. patent application Ser. No. 11/174,784, filed on 5 Jul. 2005, now U.S. Pat. No. 7,224,851, which claims priority under 35 USC §119(e) to U.S. provisional application Ser. No. 60/585,501, filed 2 Jul. 2004, the entire disclosures of which are incorporated herein by reference.

FIELD OF THE INVENTION

The present invention relates to organic compounds useful for therapy and/or prophylaxis in a mammal, and in particular to inhibitors of IAP proteins useful for treating cancers.

BACKGROUND OF THE INVENTION

Apoptosis or programmed cell death is a genetically and biochemically regulated mechanism that plays an important role in development and homeostasis in invertebrates as well as vertebrates. Aberrancies in apoptosis that lead to premature cell death have been linked to a variety of developmental disorders. Deficiencies in apoptosis that result in the lack of cell death have been linked to cancer and chronic viral infections (Thompson et al., (1995) Science 267, 1456-1462).

One of the key effector molecules in apoptosis are the caspases (cysteine containing aspartate specific proteases). Caspases are strong proteases, cleaving after aspartic acid residues and once activated, digest vital cell proteins from within the cell. Since caspases are such strong proteases, tight control of this family of proteins is necessary to prevent premature cell death. In general, caspases are synthesized as largely inactive zymogens that require proteolytic processing in order to be active. This proteolytic processing is only one of the ways in which caspases are regulated. The second mechanism is through a family of proteins that bind and inhibit caspases.

A family of molecules that inhibit caspases are the Inhibitors of Apoptosis (IAP) (Deveraux et al., J Clin Immunol (1999), 19:388-398). IAPs were originally discovered in baculovirus by their functional ability to substitute for P35 protein, an anti-apoptotic gene (Crook et al. (1993) J Virology 67, 2168-2174). IAPs have been described in organisms ranging from Drosophila to human. Regardless of their origin, structurally, IAPs comprise one to three Baculovirus IAP repeat (BIR) domains, and most of them also possess a carboxyl-terminal RING finger motif. The BIR domain itself is a zinc binding domain of about 70 residues comprising 4 alpha-helices and 3 beta strands, with cysteine and histidine residues that coordinate the zinc ion (Hinds et al., (1999) Nat. Struct. Biol. 6, 648-651). It is the BIR domain that is believed to cause the anti-apoptotic effect by inhibiting the caspases and thus inhibiting apoptosis. As an example, human X-chromosome linked IAP (XIAP) inhibits caspase 3, caspase 7 and the Apaf-1-cytochrome C mediated activation of caspase 9 (Deveraux et al., (1998) EMBO J. 17, 2215-2223). Caspases 3 and 7 are inhibited by the BIR2 domain of XIAP, while the BIR3 domain of XIAP is responsible for the inhibition of caspase 9 activity. XIAP is expressed ubiquitously in most adult and fetal tissues (Liston et al, Nature, 1996, 379(6563): 349), and is overexpressed in a number of tumor cell lines of the NCI 60 cell line panel (Fong et al, Genomics, 2000, 70:113; Tamm et al, Clin. Cancer Res. 2000, 6(5):1796). Overexpression of XIAP in tumor cells has been demonstrated to confer protection against a variety of pro-apoptotic stimuli and promotes resistance to chemotherapy (LaCasse et al, Oncogene, 1998, 17(25):3247). Consistent with this, a strong correlation between XIAP protein levels and survival has been demonstrated for patients with acute myelogenous leukemia (Tamm et al, supra). Down-regulation of XIAP expression by antisense oligonucleotides has been shown to sensitize tumor cells to death induced by a wide range of pro-apoptotic agents, both in vitro and in vivo (Sasaki et al, Cancer Res., 2000, 60(20):5659; Lin et al, Biochem J., 2001, 353:299; Hu et al, Clin. Cancer Res., 2003, 9(7):2826). Smac/DIABLO-derived peptides have also been demonstrated to sensitize a number of different tumor cell lines to apoptosis induced by a variety of pro-apoptotic drugs (Arnt et al, J. Biol. Chem., 2002, 277(46):44236; Fulda et al, Nature Med., 2002, 8(8):808; Guo et al, Blood, 2002, 99(9):3419; Vucic et al, J. Biol. Chem., 2002, 277(14):12275; Yang et al, Cancer Res., 2003, 63(4):831).

Melanoma IAP (ML-IAP) is an IAP not detectable in most normal adult tissues but is strongly upregulated in melanoma (Vucic et al., (2000) Current Bio 10:1359-1366). Determination of protein structure demonstrated significant homology of the ML-IAP BIR and RING finger domains to corresponding domains present in human XIAP, C-IAP1 and C-IAP2. The BIR domain of ML-IAP appears to have the most similarities to the BIR2 and BIR3 of XIAP, C-IAP1 and C-IAP2, and appears to be responsible for the inhibition of apoptosis, as determined by deletional analysis. Furthermore, Vucic et al., demonstrated that ML-IAP could inhibit chemotherapeutic agent induced apoptosis. Agents such as adriamycin and 4-tertiary butylphenol (4-TBP) were tested in a cell culture system of melanomas overexpressing ML-IAP and the chemotherapeutic agents were significantly less effective in killing the cells when compared to a normal melanocyte control. The mechanism by which ML-IAP produces an anti-apoptotic activity is in part through inhibition of caspase 3 and 9. ML-IAP did not effectively inhibit caspases 1, 2, 6, or 8.

Since apoptosis is a strictly controlled pathway with multiple interacting factors, the discovery that IAPs themselves are regulated was not unusual. In the fruit fly Drosophila, the Reaper (rpr), Head Involution Defective (hid) and GRIM proteins physically interact with and inhibit the anti-apoptotic activity of the Drosophila family of IAPs. In the mammal, the proteins SMAC/DIABLO act to block the IAPs and allow apoptosis to proceed. It was shown that during normal apoptosis, SMAC is processed into an active form and is released from the mitochondria into the cytoplasm where it physically binds to IAPs and prevents the IAP from binding to a caspase. This inhibition of the IAP allows the caspase to remain active and thus proceed with apoptosis. Interestingly, sequence homology between the IAP inhibitors shows that there is a four amino acid motif in the N-terminus of the processed, active proteins. This tetrapeptide appears to bind into a hydrophobic pocket in the BIR domain and disrupts the BIR domain binding to caspases (Chai et al., (2000) Nature 406: 855-862, Liu et al., (2000) Nature 408:1004-1008, Wu et al., (2000) Nature 408 1008-1012).

SUMMARY OF THE INVENTION

In one aspect of the present invention there is provided novel inhibitors of IAP proteins having the general formula (I)

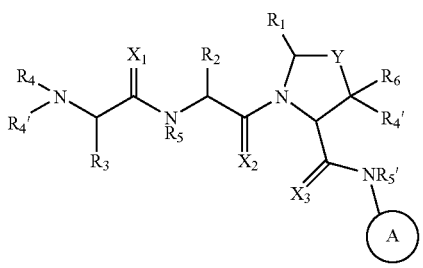

wherein $X_1$, $X_2$ and $X_3$ are independently O or S;

Y is $(CHR_7)_n$, O or S; wherein n is 1 or 2 and $R_7$ is H, halogen, alkyl, aryl, aralkyl, amino, arylamino, alkylamino, aralkylamino, alkoxy, aryloxy or aralkyloxy;

A is a 5-member heterocycle comprising 1 to 4 heteroatoms optionally substituted with amino, hydroxyl, mercapto, halogen, carboxyl, amidino, guanidino, alkyl, alkoxy, aryl, aryloxy, acyl, acyloxy, acylamino, alkoxycarbonylamino, cycloalkyl, alkylthio, alkylsulfinyl, alkylsulfonyl, aminosulfonyl, alkylaminosulfonyl, alkylsulfonylamino or a heterocycle; wherein each alkyl, alkoxy, aryl, aryloxy, acyl, acyloxy, acylamino, cycloalkyl and heterocycle substitution is optionally substituted with hydroxyl, halogen, mercapto, carboxyl, alkyl, alkoxy, haloalkyl, amino, nitro, cyano, cycloalkyl, aryl or a heterocycle;

$R_1$ is H or $R_1$ and $R_2$ together form a 5-8 member ring;

$R_2$ is alkyl, cycloalkyl, cycloalkylalkyl, aryl, aralkyl, a heterocycle or heterocyclylalkyl; each optionally substituted with hydroxyl, mercapto, halogen, amino, carboxyl, alkyl, haloalkyl, alkoxy or alkylthio;

$R_3$ is H or alkyl;

$R_4$ and $R_4'$ are independently H, hydroxyl, amino, alkyl, aryl, aralkyl, cycloalkyl, cycloalkylalkyl, heteroaryl, or heteroarylalkyl wherein each alkyl, aryl, aralkyl, cycloalkyl, cycloalkylalkyl, heteroaryl and heteroarylalkyl is optionally substituted with halogen, hydroxyl, mercapto, carboxyl, alkyl, alkoxy, amino and nitro;

$R_5$, and $R_5'$ are each independently H or alkyl;

$R_6$, and $R_6'$ are each independently H, alkyl, aryl or aralkyl; and salts and solvates thereof.

In another aspect of the invention, there are provided compositions comprising compounds of formula I and a carrier, diluent or excipient.

In another aspect of the invention, there is provided a method of inducing apoptosis in a cell comprising introducing into said cell a compound of formula I.

In another aspect of the invention, there is provided a method of sensitizing a cell to an apoptotic signal comprising introducing into said cell a compound of formula I.

In another aspect of the invention, there is provided a method for inhibiting the binding of an IAP protein to a caspase protein comprising contacting said IAP protein with a compound of formula I.

In another aspect of the invention, there is provided a method for treating a disease or condition associated with the overexpression of an IAP protein in a mammal, comprising administering to said mammal an effective amount of a compound of formula I.

DETAILED DESCRIPTION OF THE PREFERRED EMBODIMENTS

"Alkyl" means a branched or unbranched, saturated or unsaturated (i.e. alkenyl, alkynyl) aliphatic hydrocarbon group, having up to 12 carbon atoms unless otherwise specified. When used as part of another term, for example "alkylamino", the alkyl portion is preferably a saturated hydrocarbon chain, however also includes unsaturated hydrocarbon carbon chains such as "alkenylamino" and "alkynylamino. Examples of preferred alkyl groups include methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The terms "lower alkyl" "$C_1$-$C_4$ alkyl" and "alkyl of 1 to 4 carbon atoms" are synonymous and used interchangeably to mean methyl, ethyl, 1-propyl, isopropyl, cyclopropyl, 1-butyl, sec-butyl or t-butyl. Unless specified, substituted, alkyl groups may contain one (preferably), two, three or four substituents which may be the same or different. Examples of the above substituted alkyl groups include, but are not limited to; cyanomethyl, nitromethyl, hydroxymethyl, trityloxymethyl, prop ionyloxymethyl, aminomethyl, carboxymethyl, carboxyethyl, carboxypropyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-amino(iso-propyl), 2-carbamoyloxyethyl and the like. The alkyl group may also be substituted with a carbocycle group. Examples include cyclopropylmethyl, cyclobutylmethyl, cyclopentylmethyl, and cyclohexylmethyl groups, as well as the corresponding -ethyl, -propyl, -butyl, -pentyl, -hexyl groups, etc. Preferred substituted alkyls are substituted methyls e.g. a methyl group substituted by the same substituents as the "substituted $C_n$-$C_m$ alkyl" group. Examples of the substituted methyl group include groups such as hydroxymethyl, protected hydroxymethyl (e.g. tetrahydropyranyloxymethyl), acetoxymethyl, carbamoyloxymethyl, trifluoromethyl, chloromethyl, carboxymethyl, bromomethyl and iodomethyl.

"Amidine" denotes the group —C(NH)—NHR wherein R is H or alkyl or aralkyl. A preferred amidine is the group —NH—C(NH)—NH$_2$.

"Amino" denotes primary (i.e. —NH$_2$), secondary (i.e. —NRH) and tertiary (i.e. —NRR) amines. Preferred secondary and tertiary amines are alkylamine, dialkylamine, arylamine, diarylamine, aralkylamine and diaralkylamine. Particular preferred secondary and tertiary amines are methylamine, ethylamine, propylamine, isopropylamine, phenylamine, benzylamine dimethylamine, diethylamine, dipropylamine and disopropylamine.

"Amino-protecting group" as used herein refers to a derivative of the groups commonly employed to block or protect an amino group while reactions are carried out on other functional groups on the compound. Examples of such protecting groups include carbamates, amides, alkyl and aryl groups, imines, as well as many N-heteroatom derivatives which can be removed to regenerate the desired amine group. Preferred amino protecting groups are Boc, Fmoc and Cbz. Further examples of these groups are found in T. W. Greene and P. G. M. Wuts, "Protective Groups in Organic Synthesis", $2^{nd}$ ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino" refers to an amino group substituted with one of the above amino-protecting groups.

"Aryl" when used alone or as part of another term means a carbocyclic aromatic group whether or not fused having the number of carbon atoms designated or if no number is designated, up to 14 carbon atoms. Preferred aryl groups include phenyl, naphthyl, biphenyl, phenanthrenyl, naphthacenyl, and the like (see e.g. *Lang's Handbook of Chemistry* (Dean, J. A., ed) $13^{th}$ ed. Table 7-2 [1985]) and most preferred phenyl. Substituted phenyl or substituted aryl denotes a phenyl group or aryl group substituted with one, two, three, four or five, preferably 1-2, 1-3 or 1-4 substituents chosen, unless otherwise specified, from halogen (F, Cl, Br, I), hydroxy, protected hydroxy, cyano, nitro, alkyl (preferably $C_1$-$C_6$ alkyl), alkoxy (preferably $C_1$-$C_6$ alkoxy), benzyloxy, carboxy, protected carboxy, carboxymethyl, protected carboxymethyl, hydroxymethyl, protected hydroxymethyl, aminomethyl, protected aminomethyl, trifluoromethyl, alkylsulfonylamino, arylsulfonylamino, heterocyclylsulfonylamino, heterocyclyl, aryl, or other groups specified. One or more methyne (CH) and/or methylene ($CH_2$) groups in these substituents may in turn be substituted with a similar group as those denoted above. Examples of the term "substituted phenyl" includes but is not limited to a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl) phenyl and the like; a mono or di(alkoxy)phenyl group, for example, 3,4-dimethoxyphenyl, 3-methoxy-4-benzyloxyphenyl, 3-methoxy-4-(1-chloromethyl)benzyloxy-phenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl, a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl) phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetra-substituted phenyl groups where the substituents are different such as 3-methoxy-4-benzyloxy-5-methyl-6-phenyl sulfonylamino. Preferred substituted phenyl groups include the 2-chlorophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-phenyl, 3-methoxy-4-(1-chloromethyl) benzyloxy-6-methyl sulfonyl aminophenyl groups. Fused aryl rings may also be substituted with any, preferably 1, 2 or 3, of the substituents specified herein in the same manner as substituted alkyl groups.

"Carbocyclyl", "carbocyclylic", "carbocycle" and "carbocyclo" alone and when used as a moiety in a complex group such as a carbocycloalkyl group, refers to a mono-, bi-, or tricyclic aliphatic ring having 3 to 14 carbon atoms and preferably 3 to 7 carbon atoms which may be saturated or unsaturated, aromatic or non-aromatic. Preferred saturated carbocyclic groups include cyclopropyl, cyclobutyl, cyclopentyl and cyclohexyl groups and more preferred are cyclopropyl and cyclohexyl and most preferred is cyclohexyl. Preferred unsaturated carbocycles are aromatic e.g. aryl groups as previously defined, the most preferred being phenyl. The terms "substituted carbocyclyl", "carbocycle" and "carbocyclo" mean these groups substituted by the same substituents as the "substituted alkyl" group.

"Carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl such as t-butyl or t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the molecule and can be removed at the appropriate point without disrupting the remainder of the molecule. In particular, it is important not to subject a carboxy-protected molecule to strong nucleophilic bases, such as lithium hydroxide or NaOH, or reductive conditions employing highly activated metal hydrides such as $LiAlH_4$. (Such harsh removal conditions are also to be avoided when removing amino-protecting groups and hydroxy-protecting groups, discussed below.) Preferred carboxylic acid protecting groups are the alkyl (e.g. methyl, ethyl, t-butyl), allyl, benzyl and p-nitrobenzyl groups. Similar carboxy-protecting groups used in the cephalosporin, penicillin and peptide arts can also be used to protect a carboxy group substituents. Further examples of these groups are found in T. W. Greene and P. G. M. Wuts, "Protective Groups in Organic Synthesis", $2^{nd}$ ed., John Wiley & Sons, Inc., New York, N.Y., 1991, chapter 5; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The term "protected carboxy" refers to a carboxy group substituted with one of the above carboxy-protecting groups.

"Guanidine" denotes the group —NH—C(NH)—NHR wherein R is H or alkyl or aralkyl. Preferred guanidine is the group —NH—C(NH)—$NH_2$.

"Hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, benzoyl, acetoxy, carbamoyloxy, benzyl, and silylethers (e.g. TBS, TBDPS) groups. Further examples of these groups are found in T. W. Greene and P. G. M. Wuts, "Protective Groups in Organic Synthesis", $2^{nd}$ ed., John Wiley & Sons, Inc., New York, N.Y., 1991, chapters 2-3; E. Haslam, "Protective Groups in Organic Chemistry", J. G. W. McOmie, Ed., Plenum Press, New York, N.Y., 1973, Chapter 5, and T. W.

Greene, "Protective Groups in Organic Synthesis", John Wiley and Sons, New York, N.Y., 1981. The term "protected hydroxy" refers to a hydroxy group substituted with one of the above hydroxy-protecting groups.

"Heterocyclic group", "heterocyclic", "heterocycle", "heterocyclyl", or "heterocyclo" alone and when used as a moiety in a complex group such as a heterocycloalkyl group, are used interchangeably and refer to any mono-, bi-, or tricyclic, saturated or unsaturated, aromatic (heteroaryl) or non-aromatic ring having the number of atoms designated, generally from 5 to about 14 ring atoms, where the ring atoms are carbon and at least one heteroatom (nitrogen, sulfur or oxygen) and preferably 1 to 4 heteroatoms. Typically, a 5-membered ring has 0 to 2 double bonds and 6- or 7-membered ring has 0 to 3 double bonds and the nitrogen or sulfur heteroatoms may optionally be oxidized (e.g. SO, $SO_2$), and any nitrogen heteroatom may optionally be quaternized. Preferred non-aromatic heterocycles include morpholinyl (morpholino), pyrrolidinyl, oxiranyl, oxetanyl, tetrahydrofuranyl, 2,3-dihydrofuranyl, 2H-pyranyl, tetrahydropyranyl, thiiranyl, thietanyl, tetrahydrothietanyl, aziridinyl, azetidinyl, 1-methyl-2-pyrrolyl, piperazinyl and piperidinyl. A "heterocycloalkyl" group is a heterocycle group as defined above covalently bonded to an alkyl group as defined above. Preferred 5-membered heterocycles containing a sulfur or oxygen atom and one to three nitrogen atoms include thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, preferably oxazol-2-yl, and oxadiazolyl, such as 1,3,4-oxadiazol-5-yl, and 1,2,4-oxadiazol-5-yl. Preferred 5-membered ring heterocycles containing 2 to 4 nitrogen atoms include imidazolyl, preferably imidazol-2-yl; triazolyl, preferably 1,3,4-triazol-5-yl; 1,2,3-triazol-5-yl, 1,2,4-triazol-5-yl, and tetrazolyl, preferably 1H-tetrazol-5-yl. Preferred benzo-fused 5-membered heterocycles are benzoxazol-2-yl, benzthiazol-2-yl and benzimidazol-2-yl. Preferred 6-membered heterocycles contain one to three nitrogen atoms and optionally a sulfur or oxygen atom, for example pyridyl, such as pyrid-2-yl, pyrid-3-yl, and pyrid-4-yl; pyrimidyl, preferably pyrimid-2-yl and pyrimid-4-yl; triazinyl, preferably 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are a preferred group. Substituents for optionally substituted heterocycles, and further examples of the 5- and 6-membered ring systems discussed above can be found in W. Druckheimer et al., U.S. Pat. No. 4,278,793.

"Heteroaryl" alone and when used as a moiety in a complex group such as a heteroaralkyl group, refers to any mono-, bi-, or tricyclic aromatic ring system having the number of atoms designated where at least one ring is a 5-, 6- or 7-membered ring containing from one to four heteroatoms selected from the group nitrogen, oxygen, and sulfur, and preferably at least one heteroatom is nitrogen (*Lang's Handbook of Chemistry*, supra). Included in the definition are any bicyclic groups where any of the above heteroaryl rings are fused to a benzene ring. Heteroaryls in which nitrogen or oxygen is the heteroatom are preferred. The following ring systems are examples of the heteroaryl (whether substituted or unsubstituted) groups denoted by the term "heteroaryl": thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzofuryl, benzothiazolyl, benzothiadiazolyl, benzotriazolyl, benzoimidazolyl and indolyl. A particularly preferred group of "heteroaryl" include; 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl sodium salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino) eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-as-triazin-3-yl sodium salt, 2,5-dihydro-5-oxo-6-hydroxy-2-methyl-astriazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo[1,5-b]-pyridazin-6-yl. An alternative group of "heteroaryl" includes; 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl.

"Inhibitor" means a compound which reduces or prevents the binding of IAP proteins to caspase proteins or which reduces or prevents the inhibition of apoptosis by an IAP protein. Alternatively, "inhibitor" means a compound which prevents the binding interaction of X-IAP with caspases or the binding interaction of ML-IAP with SMAC.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, aralphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

The present invention provides novel compounds having the general formula I:

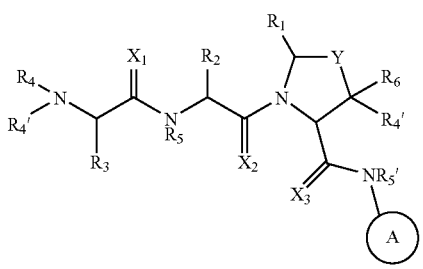

wherein X, Y, A, $R_1$, $R_2$, $R_3$, $R_4$, $R_4'$, $R_5$, $R_5'$, $R_6$ and $R_6'$ are as described herein.

$X_1$ and $X_2$ are each independently O or S. In a preferred embodiment, $X_1$ and $X_2$ are both O. In another preferred embodiment $X_1$ and $X_2$ are both S. In another preferred embodiment, $X_1$ is S while $X_2$ is O. In another preferred embodiment, $X_1$ is O while $X_2$ is S.

Y is $(CHR_7)_n$, O or S; wherein n is 1 or 2 and $R_7$ is H, halogen, alkyl, aryl, aralkyl, amino, arylamino, alkylamino, aralkylamino, alkoxy, aryloxy or aralkyloxy. In a particular embodiment, Y is $CH_2$. In a particular embodiment n is 1. In a particular embodiment n is 1 and Y is $CHR_7$ wherein $R_7$ is aralkyloxy, for example benzyloxy. In a particular embodiment n is 1 and Y is $CHR_7$ wherein $R_7$ is F. In a particular embodiment n is 1 and Y is $CHR_7$ wherein $R_7$ is aralkylamino, for example benzylamino. In another particular embodiment Y is O. In another particular embodiment Y is S.

Ring 'A' is a 5-member heterocycle comprising 1 to 4 heteroatoms optionally substituted with amino, hydroxyl, mercapto, halogen, carboxyl, amidino, guanidino, alkyl, alkoxy, aryl, aryloxy, acyl, acyloxy, acylamino, alkoxycarbonylamino, cycloalkyl, alkylthio, alkylsulfinyl, alkylsulfonyl, aminosulfonyl, alkylaminosulfonyl, alkylsulfonylamino or a heterocycle; wherein each alkyl, alkoxy, aryl, aryloxy, acyl, acyloxy, acylamino, cycloalkyl and heterocycle substitution is optionally substituted with hydroxyl, halogen, mercapto, carboxyl, alkyl, alkoxy, haloalkyl, amino, nitro, cyano, cycloalkyl, aryl or a heterocycle. In an embodiment, the 5-member heterocycle ring A groups are optionally substituted with amino, hydroxyl, mercapto, halogen, carboxyl, amidino, guanidino, alkyl, alkoxy, aryl, aryloxy, acyl, acyloxy, acylamino, cycloalkyl or a heterocycle; wherein each alkyl, alkoxy, aryl, aryloxy, acyl, acyloxy, acylamino, cycloalkyl and heterocycle substitution is optionally substituted with hydroxyl, halogen, mercapto, carboxyl, alkyl, haloalkyl, amino, nitro, cycloalkyl, aryl or a heterocycle. In a particular embodiment ring A is aromatic. In a particular embodiment ring A has the formula IIa or IIb:

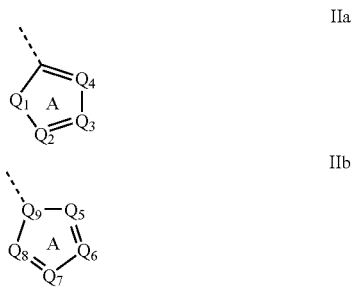

wherein $Q_1$ is $NR_8$, O or S; $Q_2$, $Q_3$, $Q_4$, $Q_5$, $Q_6$, $Q_7$, and $Q_8$, are independently $CR_9$ or N; wherein $R_9$ is H, amino, hydroxyl, mercapto, halogen, carboxyl, amidino, guanidino, alkyl, alkoxy, aryl, aryloxy, acyl, acyloxy, acylamino, cycloalkyl or a heterocycle; wherein each alkyl, alkoxy, aryl, aryloxy, acyl, acyloxy, acylamino, cycloalkyl and heterocycle substitution is optionally substituted with hydroxyl, halogen, mercapto, carboxyl, alkyl, haloalkyl, amino, nitro, cycloalkyl, aryl or a heterocycle; $R_8$ is H, alkyl, acyl, aryl, cycloalkyl or a heterocycle; wherein each alkyl, aryl, cycloalkyl and heterocycle is optionally substituted with hydroxyl, halogen, mercapto, carboxyl, alkyl, haloalkyl, amino, nitro, cycloalkyl, aryl or a heterocycle; and $Q_9$ is CH or N. In a particular embodiment, ring A is a group of formula II. In a particular embodiment ring A is a group of formula II wherein $Q_4$ is $CR_9$ wherein $R_9$ is aryl or heteroaryl optionally substituted as described above. In a particular embodiment ring A is a group of formula II wherein $Q_4$ is $CR_9$ and $R_9$ is phenyl. In a particular embodiment, ring A is a group of formula II wherein $Q_4$ is $CR_9$ and $R_9$ is phenyl and $Q_3$ is CH or CF. In another embodiment, ring A is a group of formula II wherein $Q_4$ is $CR_9$ and $R_9$ is pyridin-2-yl. In another embodiment, ring A is a group of formula II wherein $Q_4$ is $CR_9$, $R_9$ is pyridin-2-yl and $Q_3$ is C-Me.

In another embodiment, ring A according to IIa or IIb is a pyrrole ring optionally substituted with alkyl, aryl, aralkyl, cycloalkyl, cycloalkylalkyl, a heterocycle or a heterocyclealkyl optionally substituted with halogen hydroxyl, mercapto, carboxyl, alkyl, haloalkyl, amino, nitro, aryl or heteroaryl. In an embodiment ring A is substituted with an aryl or heteroaryl group. In a particular embodiment, ring A is selected from the group consisting of:

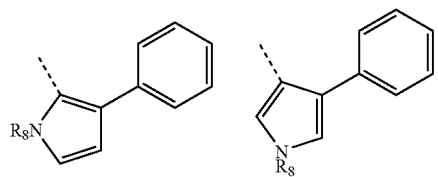

-continued

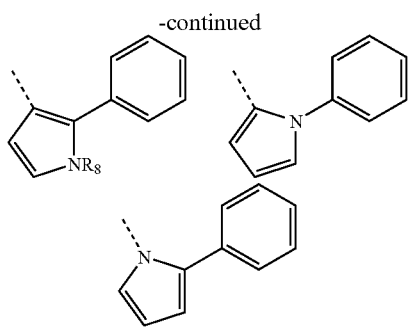

wherein $R_8$ is H, alkyl (for example methyl, ethyl or propyl) or acyl (for example acetyl). In a particular embodiment $R_8$ is H.

In another embodiment ring A is furan optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring A is substituted with an aryl or heteroaryl group. In a particular embodiment, ring A is selected from the group consisting of:

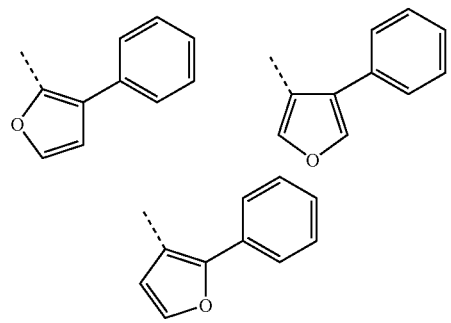

In another embodiment ring A is thiophene optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring A is substituted with an aryl or heteroaryl group. In a particular embodiment, ring A is selected from the group consisting of:

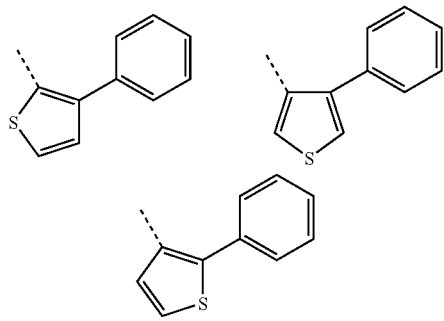

In another embodiment ring A is pyrazole optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring A is substituted with an aryl or heteroaryl group. In a particular embodiment, ring A is selected from the group consisting of:

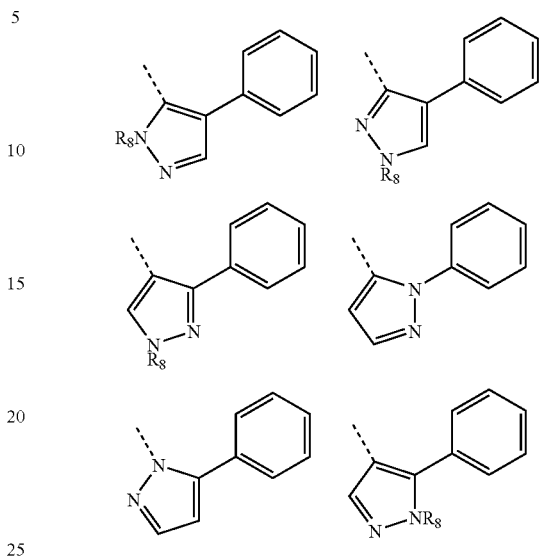

wherein $R_8$ is H, alkyl (for example methyl, ethyl or propyl) or acyl (for example acetyl). In a particular embodiment $R_8$ is H.

In another embodiment ring A is imidazole optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring A is substituted with an aryl or heteroaryl group. In a particular embodiment, ring A is selected from the group consisting of:

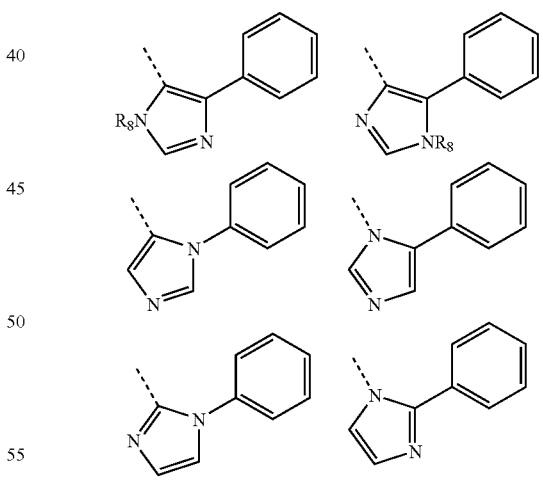

wherein $R_8$ is H, alkyl (for example methyl, ethyl or propyl) or acyl (for example acetyl). In a particular embodiment $R_8$ is H.

In another embodiment ring A is oxazole optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring A is substituted with an aryl or heteroaryl group. In a particular embodiment, ring A is selected from the group consisting of:

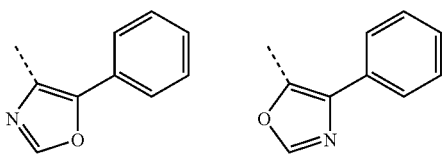

In another embodiment ring A is isoxazole optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring A is substituted with an aryl or heteroaryl group. In a particular embodiment, ring A is selected from the group consisting of:

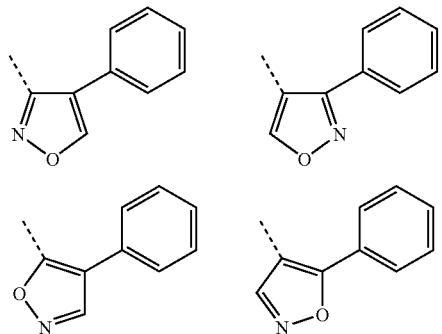

In another embodiment ring A is thiazole optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring A is substituted with an aryl or heteroaryl group. In a particular embodiment, ring A is selected from the group consisting of:

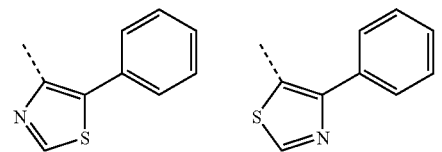

In another embodiment ring A is isothiazole optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring A is substituted with an aryl or heteroaryl group. In a particular embodiment, ring A is selected from the group consisting of:

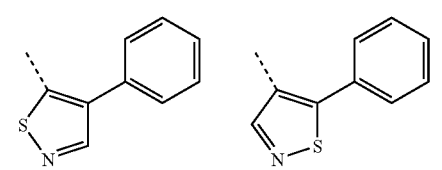

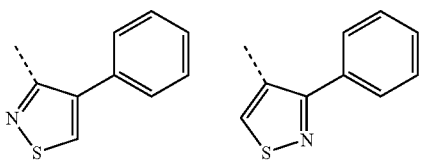

In another embodiment ring A is 1,2,3-triazole optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring A is substituted with an aryl or heteroaryl group. In a particular embodiment, ring A is selected from the group consisting of:

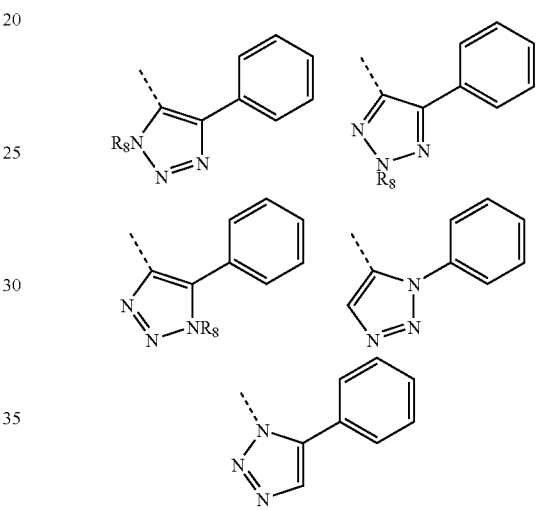

wherein $R_8$ is H, alkyl (for example methyl, ethyl or propyl) or acyl (for example acetyl). In a particular embodiment $R_8$ is H.

In another embodiment ring A is 1,2,4-triazole optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring A is substituted with an aryl or heteroaryl group. In a particular embodiment, ring A is selected from the group consisting of:

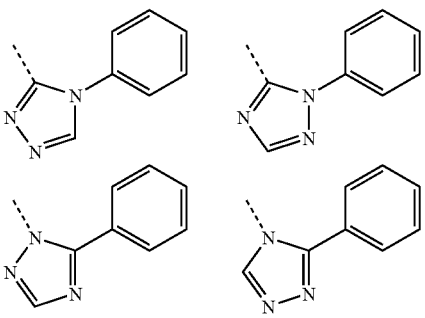

In another embodiment ring A is oxadiazole optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring A is substituted with an aryl or heteroaryl group. In a particular embodiment, ring A is selected from the group consisting of:

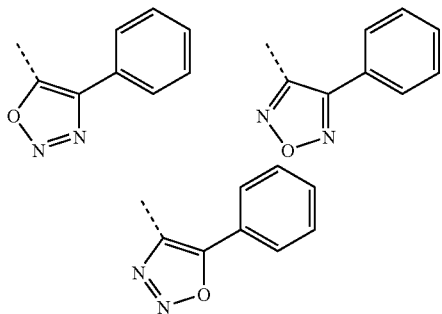

In another embodiment ring A is thiadiazole optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring A is substituted with an aryl or heteroaryl group. In a particular embodiment, ring A is selected from the group consisting of:

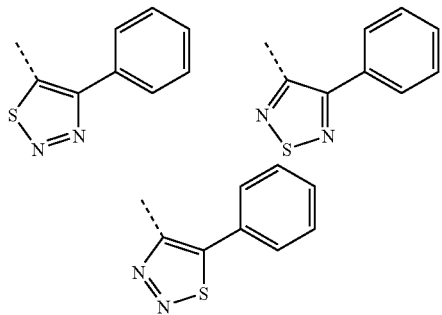

In another embodiment ring A is tetrazole optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring A is substituted with an aryl or heteroaryl group. In a particular embodiment, ring A is selected from the group consisting of:

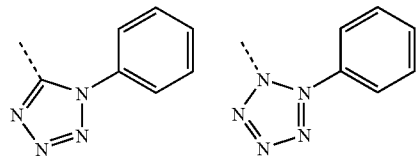

In a particular embodiment ring A is:

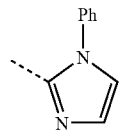

In a particular embodiment ring A is:

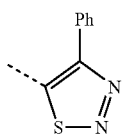

$R_1$ is H or $R_1$ and $R_2$ together form a 5-8 member ring. In a particular embodiment, $R_1$ is H. In a particular embodiment, $R_1$ and $R_2$ together form a 6-member ring. In a particular embodiment, $R_1$ and $R_2$ together form a 7-member ring. In another particular embodiment, $R_1$ and $R_2$ together form an 8-member ring. In another particular embodiment, $R_1$ and $R_2$ together form a 7-member ring while Y is S. In another particular embodiment, $R_1$ is H, while Y is $CH_2$. In another particular embodiment, $R_1$ is H, while Y is S. In another particular embodiment, $R_1$ is H, while Y is O.

$R_2$ is alkyl, cycloalkyl, cycloalkylalkyl, aryl, aralkyl, a heterocycle or heterocyclylalkyl. In a preferred embodiment $R_2$ is alkyl or cycloalkyl. In an embodiment, each $R_2$ group is each optionally substituted with hydroxyl, mercapto, halogen, amino, carboxyl, alkyl, haloalkyl, alkoxy or alkylthio; In an embodiment of the invention $R_2$ is t-butyl, isopropyl, cyclohexyl, cyclopentyl or phenyl. In a particular embodiment, $R_2$ is cyclohexyl. In another embodiment $R_2$ is tetrahydropyran-4-yl. In another particular embodiment, $R_2$ is isopropyl (i.e. the valine amino acid side chain). In another particular embodiment, $R_2$ is t-butyl. In a particular embodiment $R_2$ is oriented such that the amino acid, or amino acid analogue, which it comprises is in the L-configuration.

$R_3$ is H or alkyl. In a preferred embodiment $R_3$ is H or methyl, ethyl, propyl or isopropyl. In a particularly preferred embodiment $R_3$ is H or methyl. In a most preferred embodiment $R_3$ is methyl. In another particular embodiment, $R_3$ is t-butyl. In a preferred embodiment $R_3$ is oriented such that the amino acid, or amino acid analogue, which it comprises is in the L-configuration.

$R_4$ and $R_4'$ are independently H, hydroxyl, amino, alkyl, aryl, aralkyl, cycloalkyl, cycloalkylalkyl, heteroaryl, or heteroarylalkyl wherein each alkyl, aryl, aralkyl, cycloalkyl, cycloalkylalkyl, heteroaryl and heteroarylalkyl is optionally substituted with halogen, hydroxyl, mercapto, carboxyl, alkyl, alkoxy, amino and nitro. In a particular embodiment $R_4$ and $R_4'$ are both H. In another particular embodiment $R_4$ is methyl and $R_4'$ is H. In a particular embodiment one of $R_4$ and $R_4'$ is hydroxyl (OH) while the other is H. In another embodiment, one of $R_4$ and $R_4'$ is amino, such as $NH_2$, NHMe and NHEt, while the other is H. In a particular embodiment, $R_4'$ is H and $R_4$ is H, alkyl, aryl, aralkyl, cycloalkyl, cycloalkylalkyl, heteroaryl or heteroarylalkyl. In a particular embodiment $R_4$ is a group selected from the group consisting of:

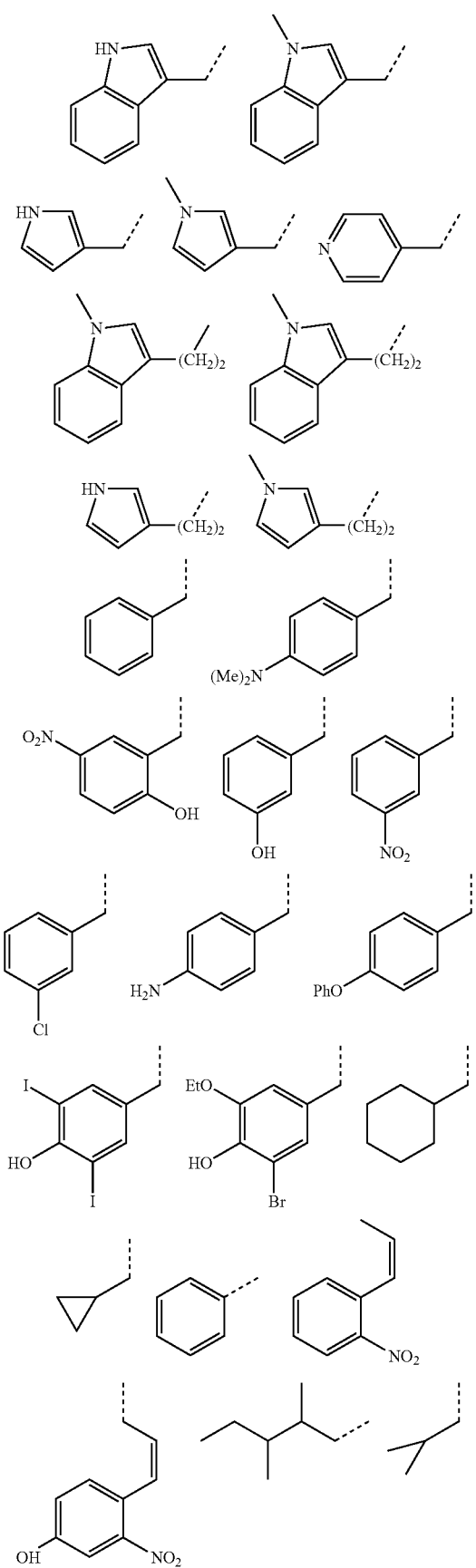
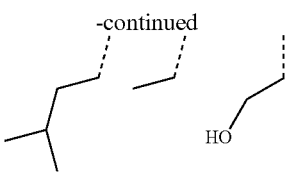

-continued

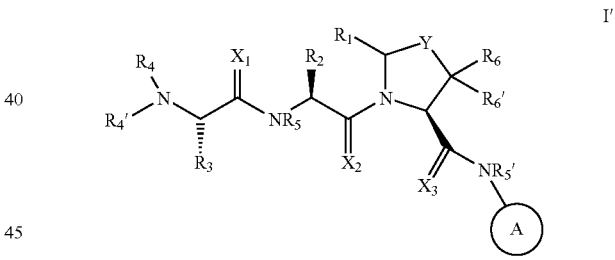

$R_5$ and $R_5'$ are each independently H or alkyl. In a preferred embodiment, $R_5$ and $R_5'$ are H or methyl. In a particular embodiment, $R_5$ is H and $R_5'$ is methyl. In another particular embodiment, $R_5$ is methyl and $R_5'$ is H. In another particular embodiment $R_5$ and $R_5'$ are both methyl. In another particular embodiment, $R_5$ and $R_5'$ are both H.

$R_6$, and $R_6'$ are each independently H, alkyl, aryl or aralkyl. In a particular embodiment, $R_6$ is alkyl, for example methyl. In another particular embodiment $R_6$ is aryl, for example phenyl. In another particular embodiment $R_6$ is aralkyl, for example benzyl. In a particular embodiment $R_6$ and $R_6'$ are the same, for example both alkyl, e.g. both methyl. In another particular embodiment $R_6$ is methyl and $R_6'$ is H.

Compounds of the invention contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention. Preferably, compounds of the invention have the following stereochemical configuration of formula I'

I' wherein X, Y, A, $R_1$, $R_2$, $R_3$, $R_4$, $R_4'$, $R_5$, $R_5'$, $R_6$ and $R_6'$ are as described herein.

The invention also encompasses prodrugs of the compounds described above. Suitable prodrugs where applicable include known amino-protecting and carboxy-protecting groups which are released, for example hydrolyzed, to yield the parent compound under physiologic conditions. A preferred class of prodrugs are compounds in which a nitrogen atom in an amino, amidino, aminoalkyleneamino, iminoalkyleneamino or guanidino group is substituted with a hydroxy (OH) group, an alkylcarbonyl (—CO—R) group, an alkoxycarbonyl (—CO—OR), an acyloxyalkyl-alkoxycarbonyl (—CO—O—R—O—CO—R) group where R is a monovalent or divalent group and as defined above or a group having the formula —C(O)—O—CP1P2-haloalkyl, where P1 and P2 are the same or different and are H, lower alkyl, lower alkoxy, cyano, halo lower alkyl or aryl. Preferably the nitrogen atom is one of the nitrogen atoms of the amidino group of the compounds of the invention. These prodrug compounds are prepared reacting the compounds of the invention described above with an activated acyl compound to bond a nitrogen atom in the compound of the invention to the carbonyl of the activated acyl compound. Suitable activated carbonyl compounds contain a good leaving group bonded to the carbonyl carbon and include acyl halides, acyl amines, acyl pyridinium salts, acyl alkoxides, in particular acyl phenoxides such as p-nitrophenoxy acyl, dinitrophenoxy acyl, fluorophenoxy acyl, and difluorophenoxy acyl. The reactions are generally exothermic and are carried out in inert solvents at reduced temperatures such as −78 to about 50 C. The reactions are usually also carried out in the presence of an inorganic base such as potassium carbonate or sodium bicarbonate, or an organic base such as an amine, including pyridine, triethylamine, etc. One manner of preparing prodrugs is described in U.S. Ser. No. 08/843,369 filed Apr. 15, 1997 (corresponding to PCT publication WO9846576) the contents of which are incorporated herein by reference in their entirety.

Particular compounds of formula I include the following:

1

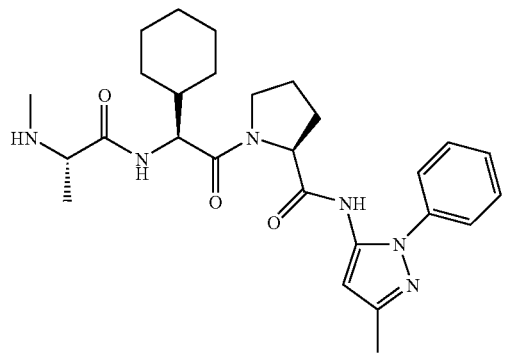

2

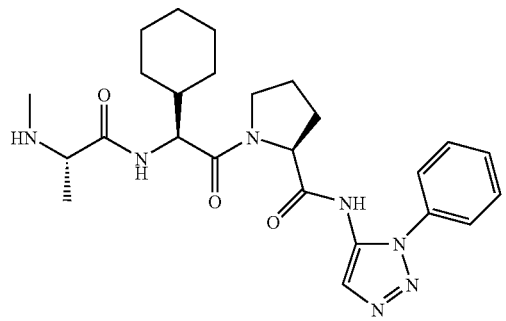

3

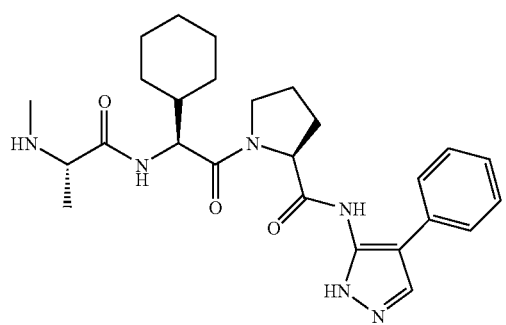

-continued

4

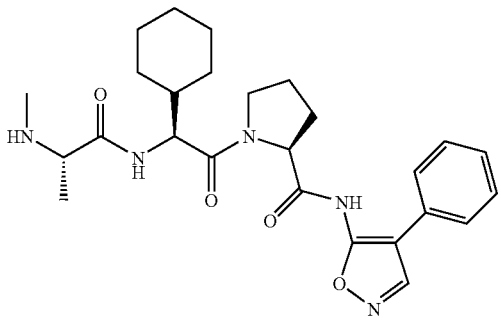

5

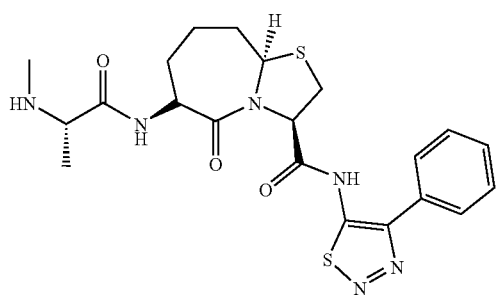

6

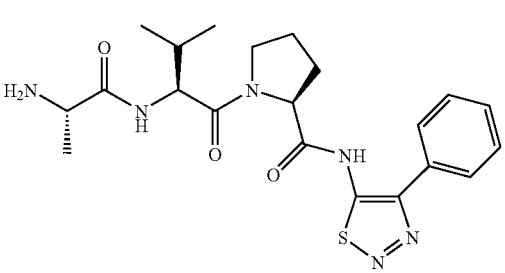

7

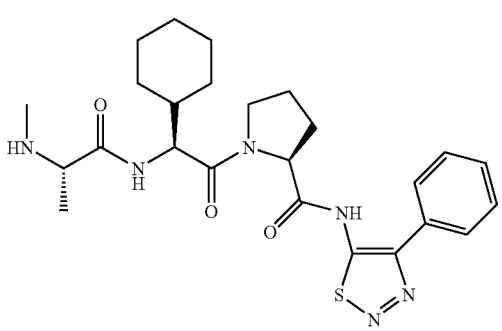

8

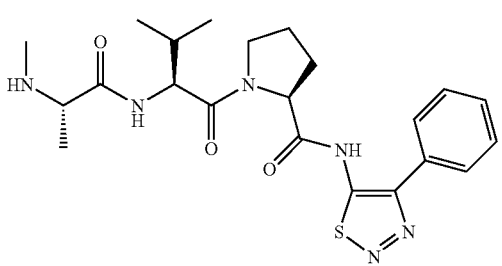

9
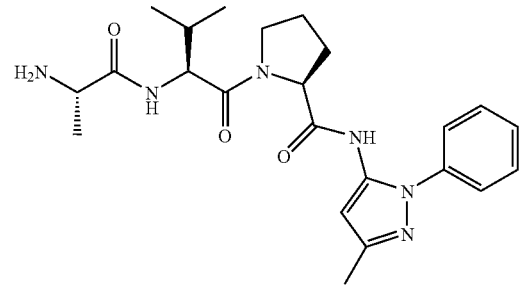
10
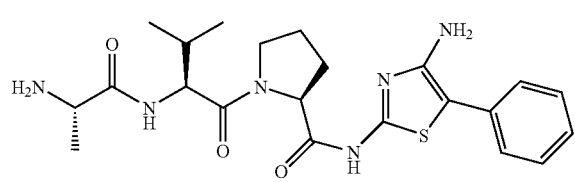
11
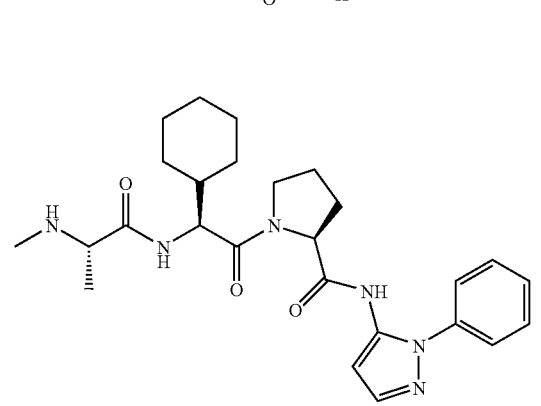
12
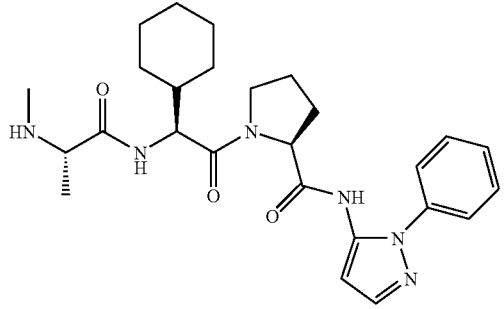
13
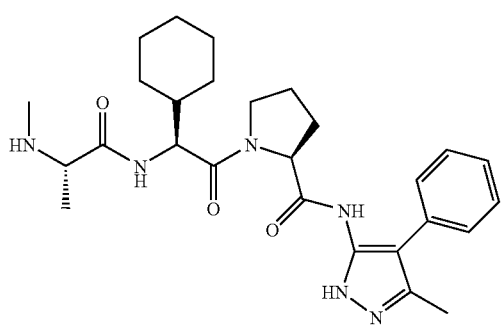
14
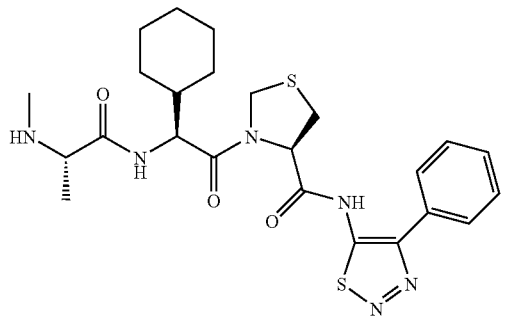
15
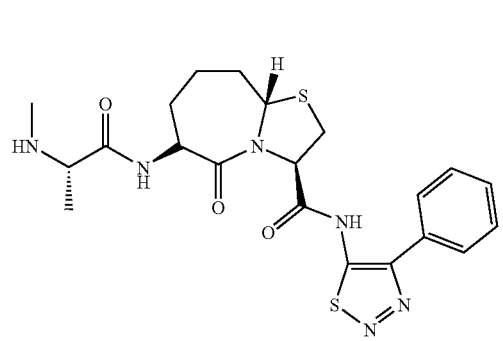
16
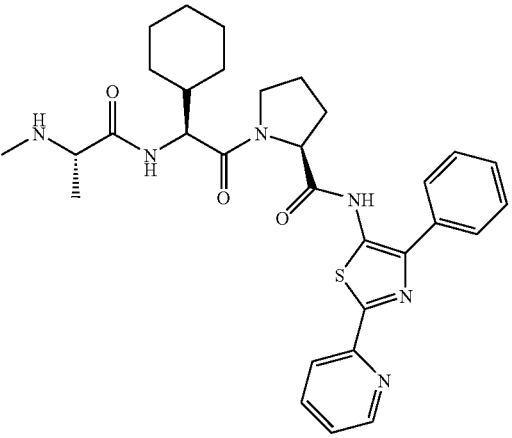
17
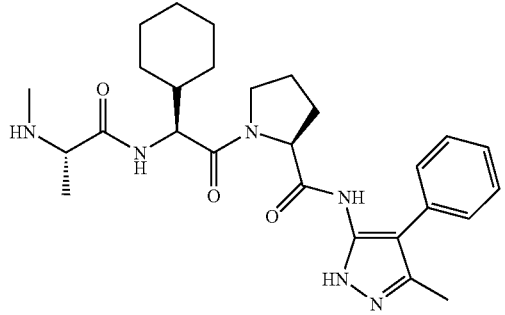

18
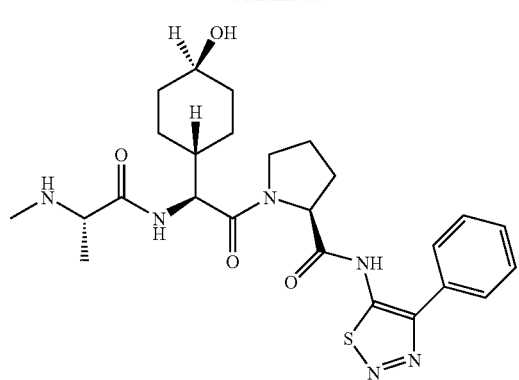
19
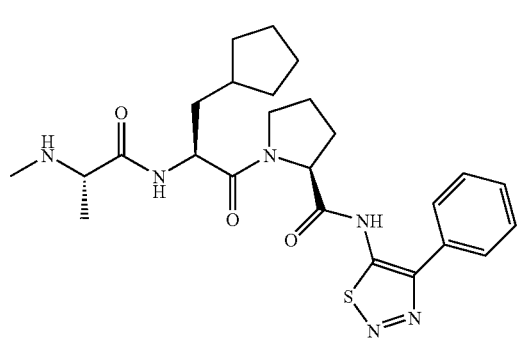
20
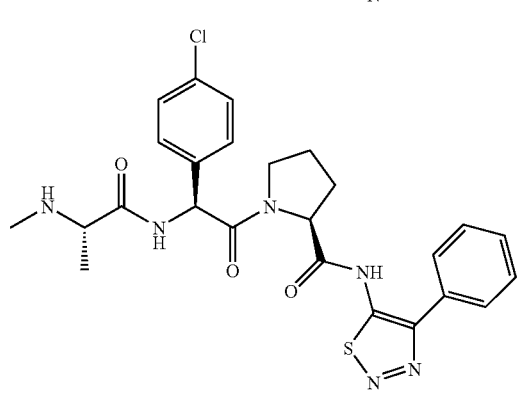
21
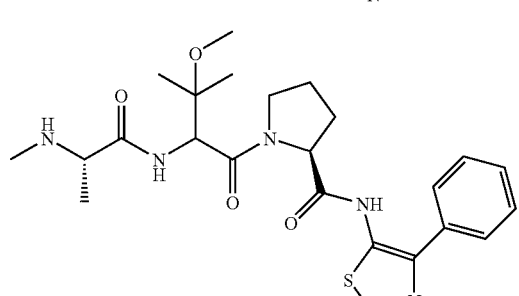
22
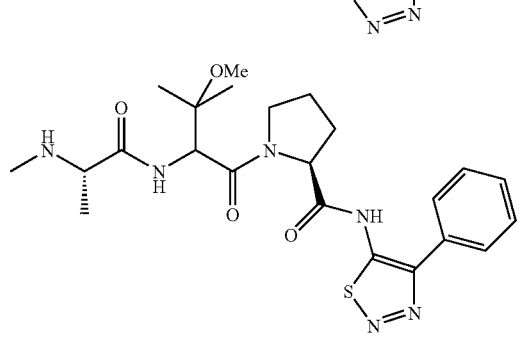
23
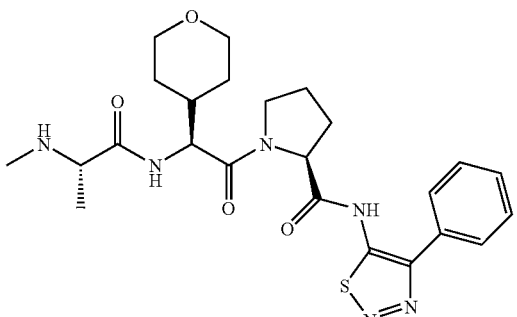
24
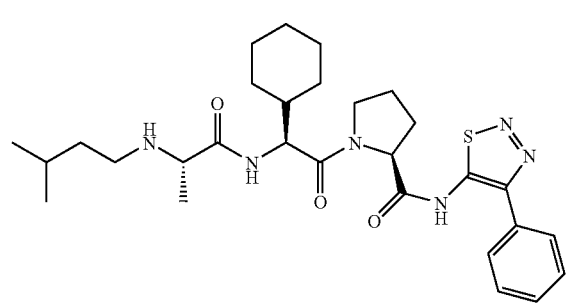
25
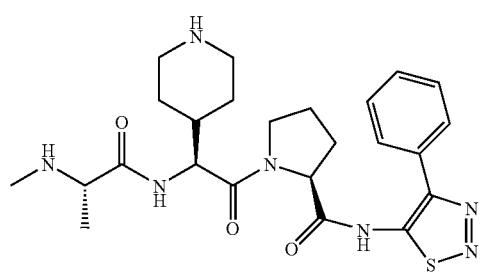
26
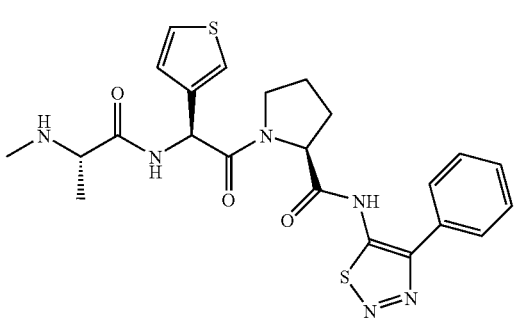
27
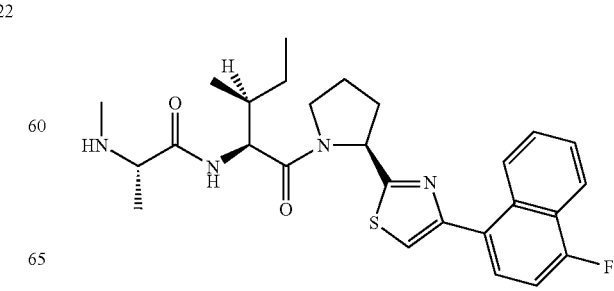

25
-continued
28
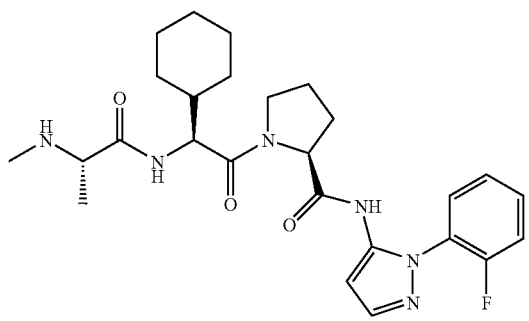
29
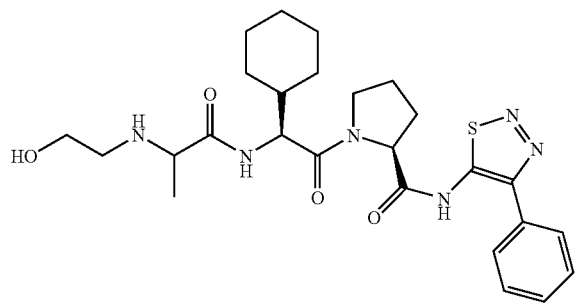
30
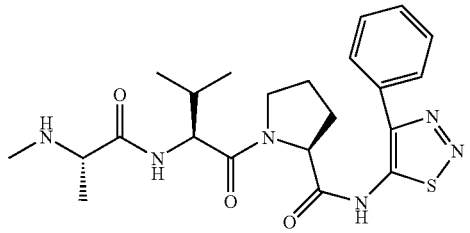
31
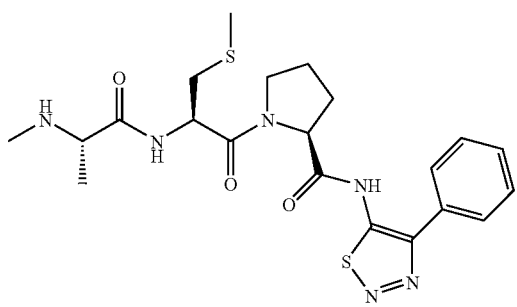
32
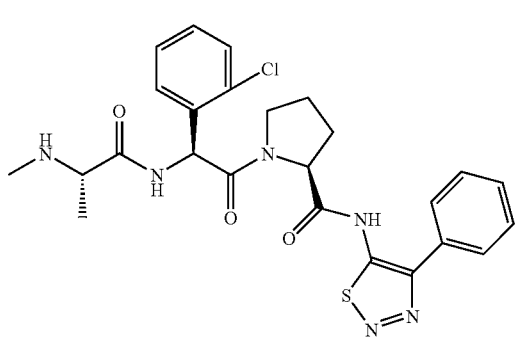
26
-continued
33
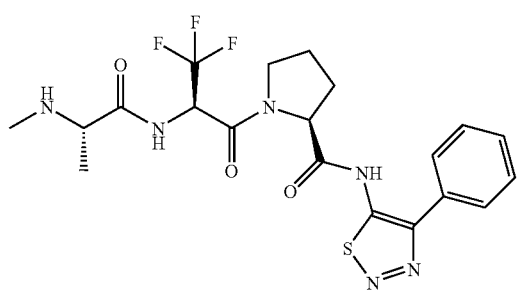
34
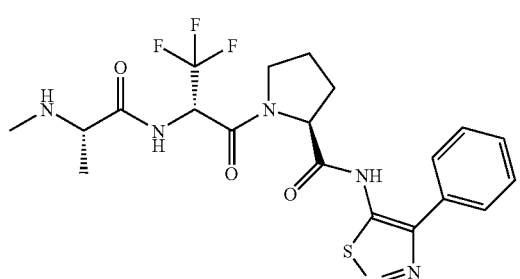
35
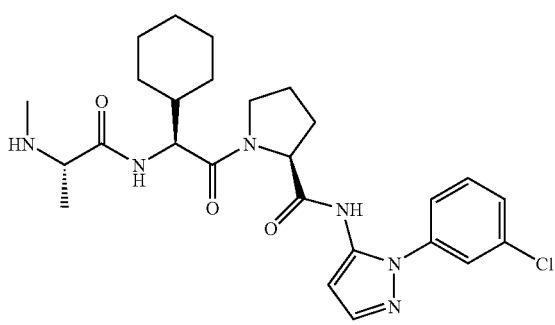
36
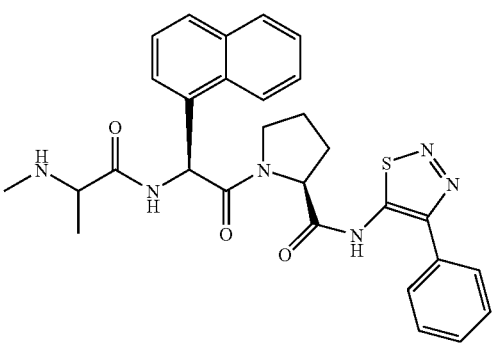
37
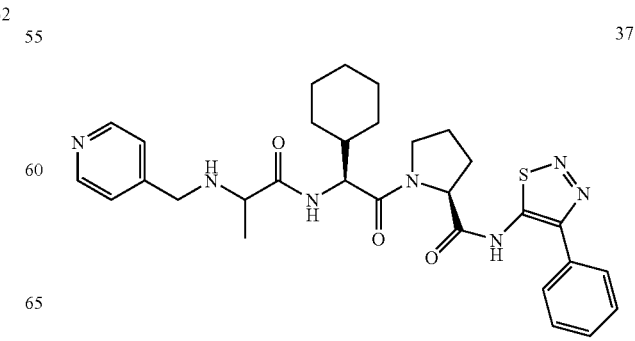

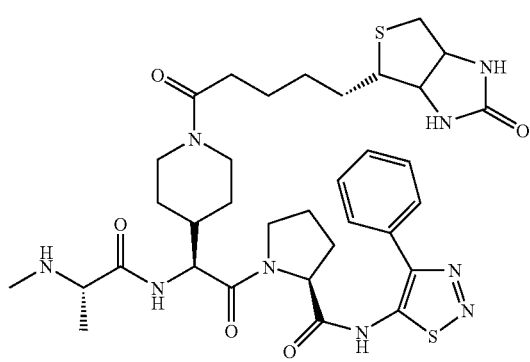
38
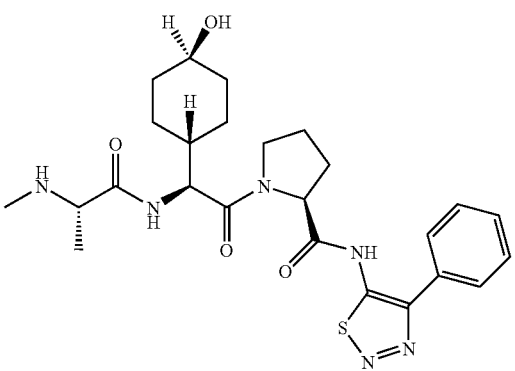
42
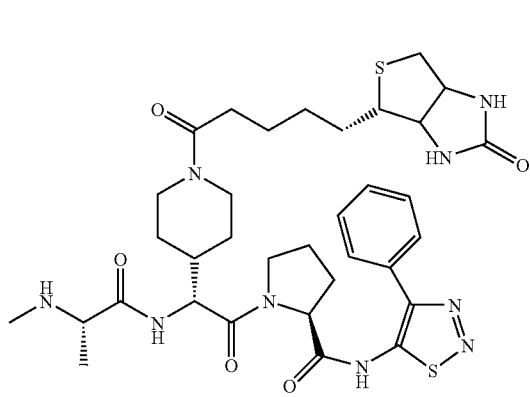
39
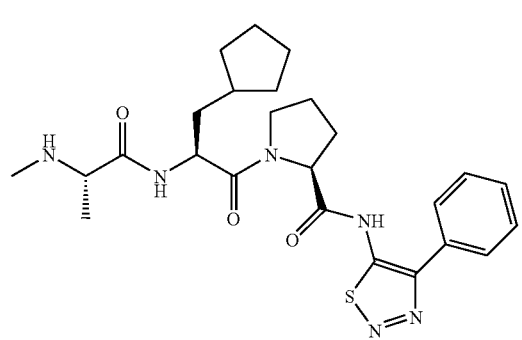
43
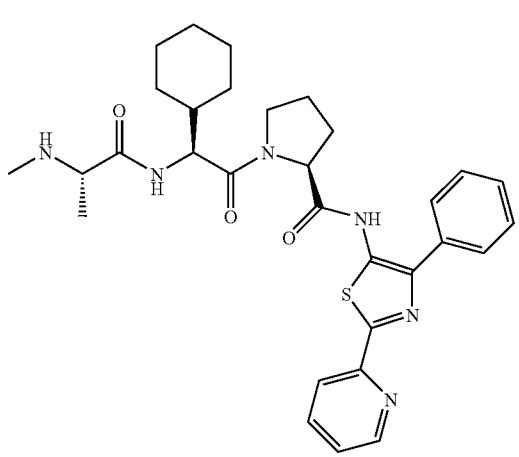
40
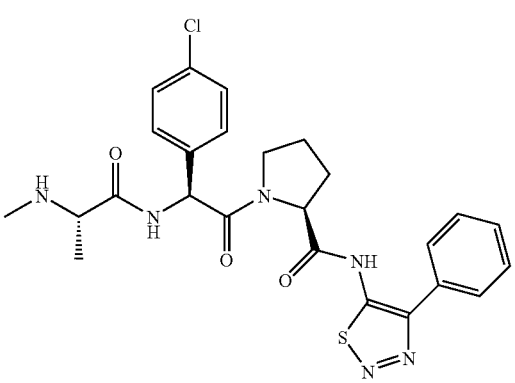
44
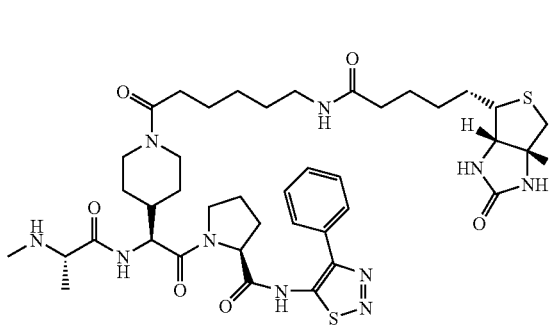
41
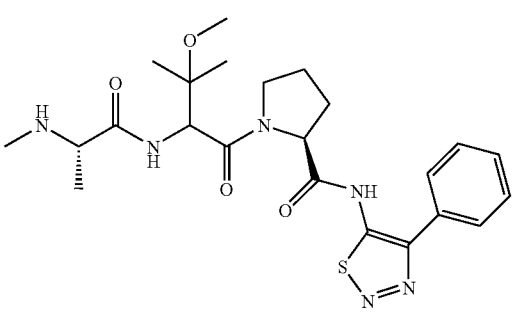
45

46
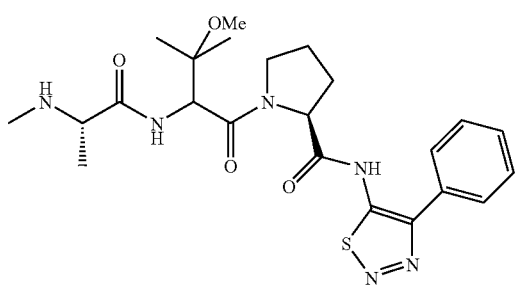
47
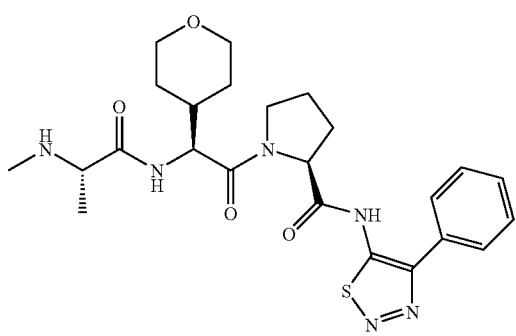
48
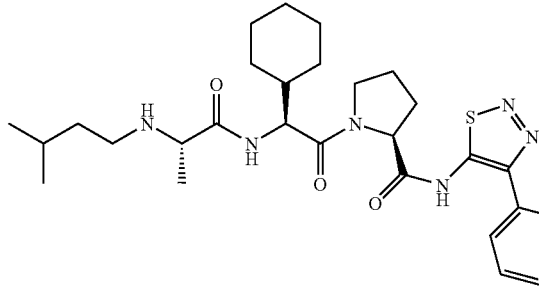
49
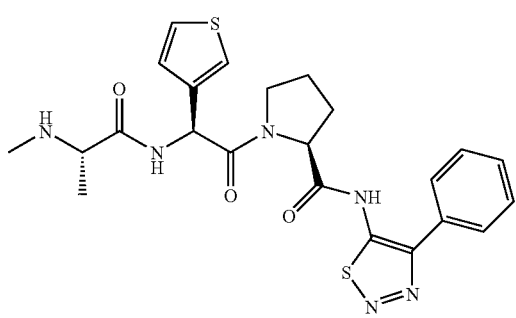
51
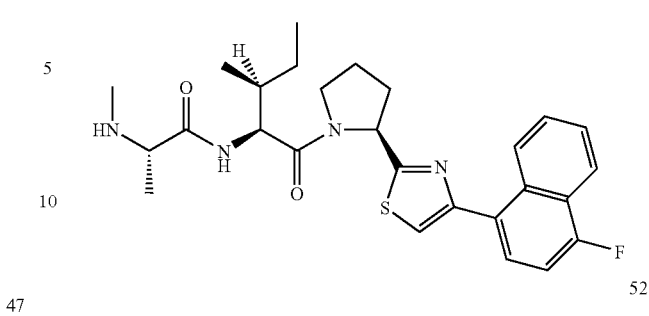
52
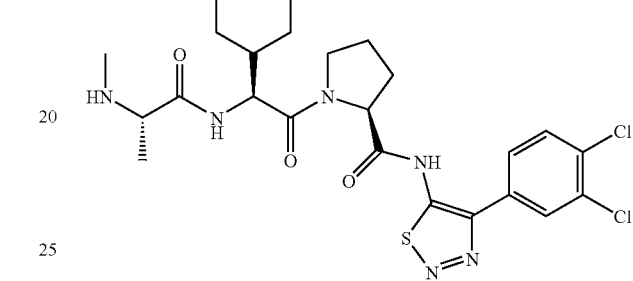
53
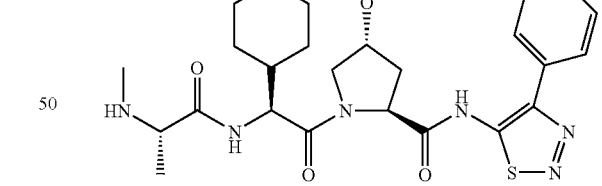
54
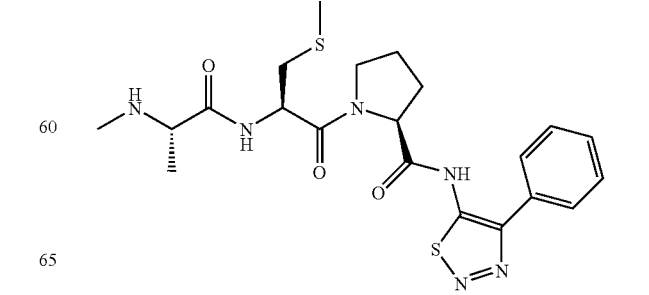

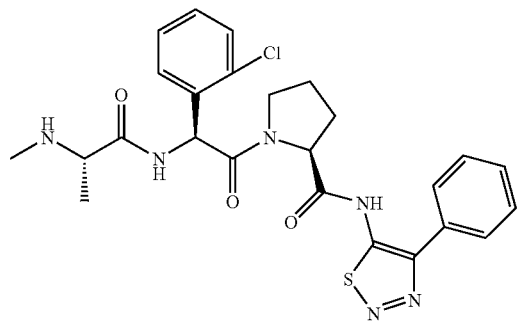
56
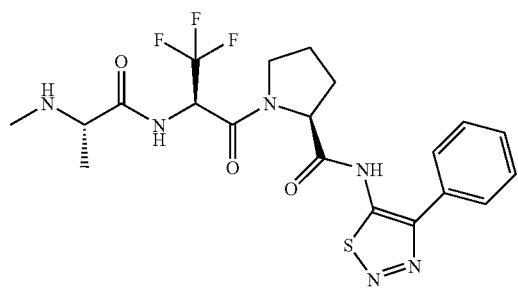
57
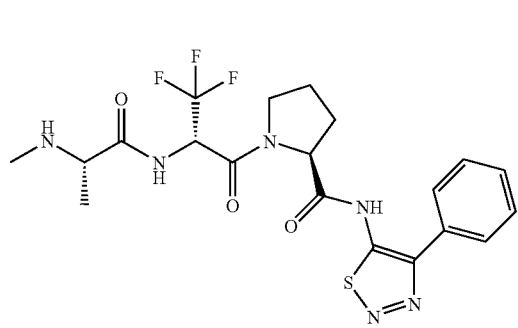
58
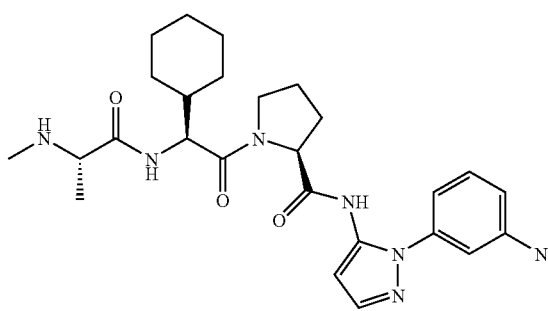
59
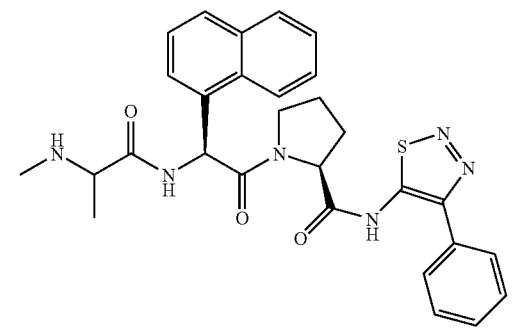
60
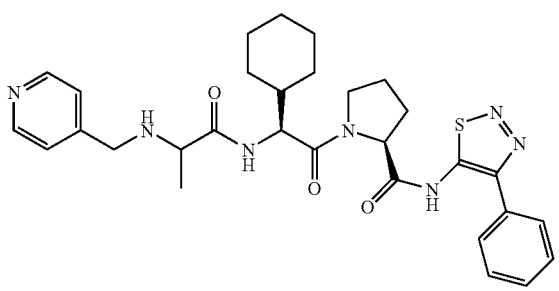
61
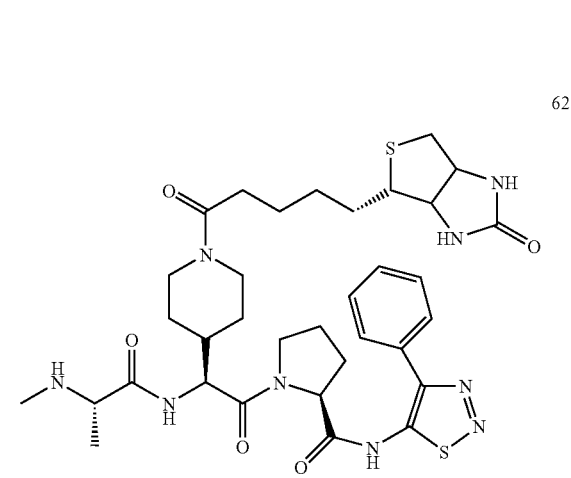
62
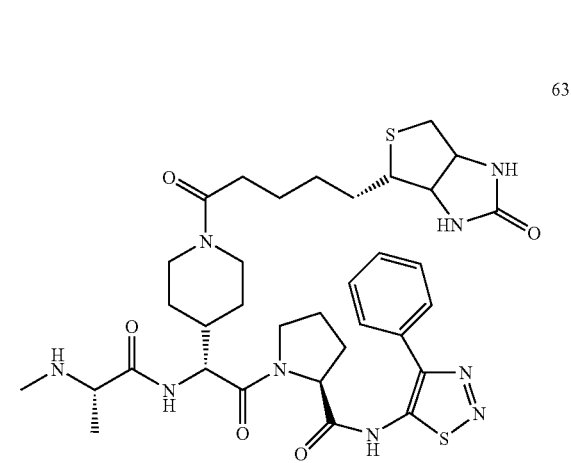
63
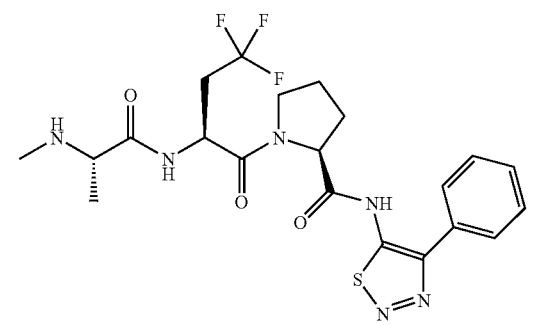
64

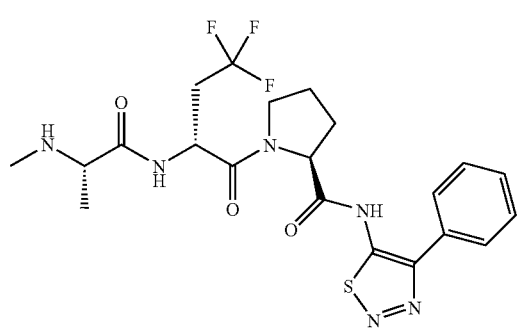
65
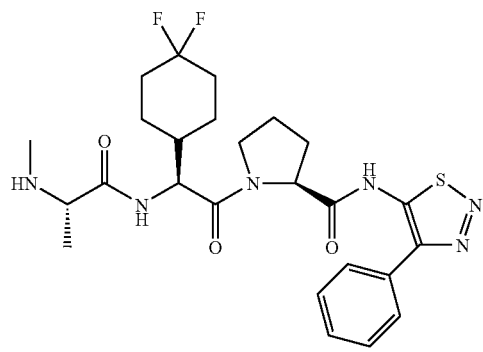
69
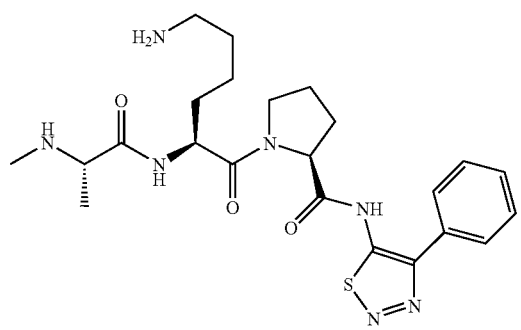
66
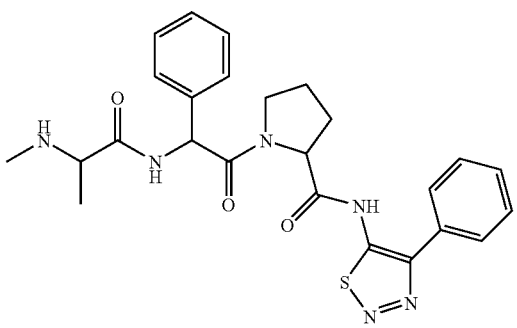
70
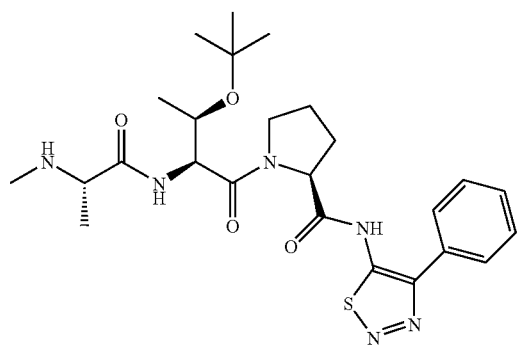
67
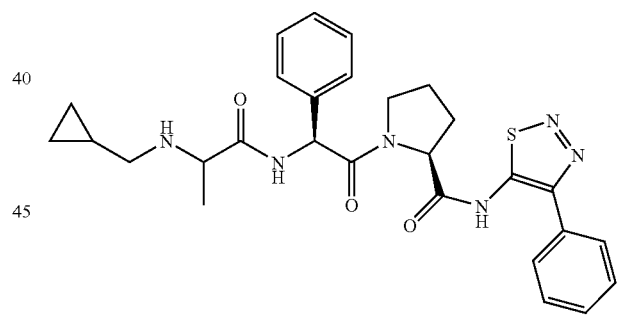
71
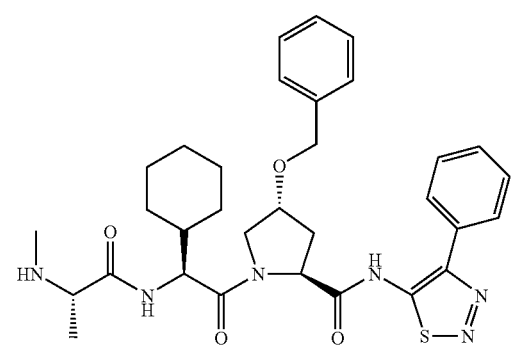
68
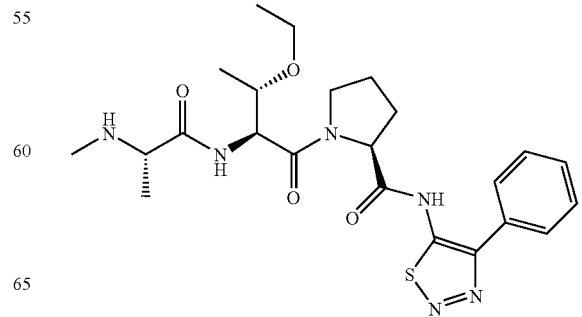
72

35
-continued
73
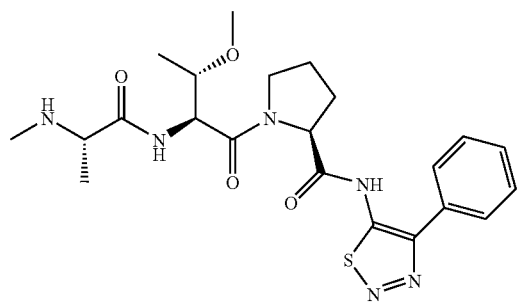
74
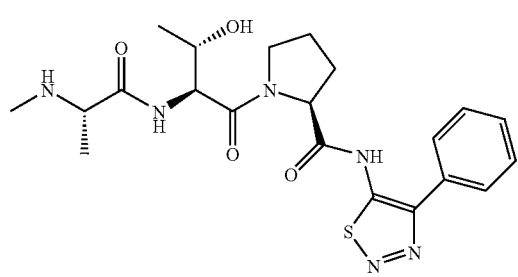
75
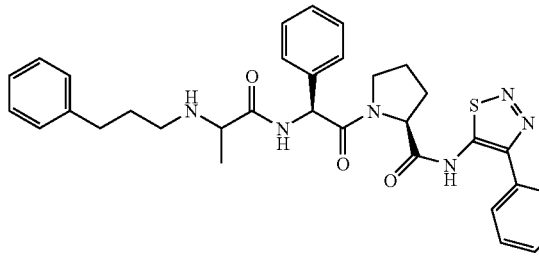
76
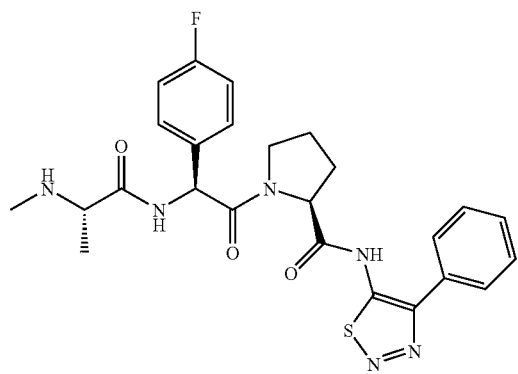
77
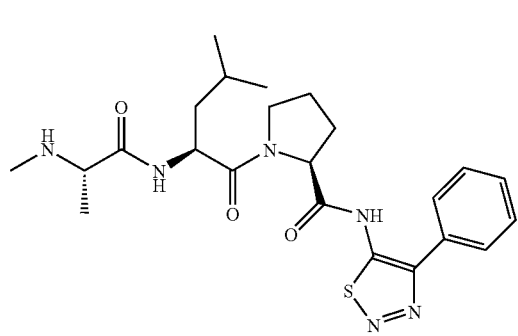
36
-continued
78
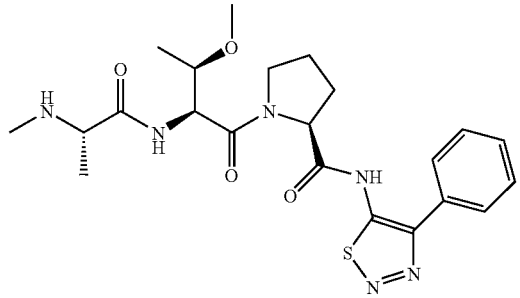
79
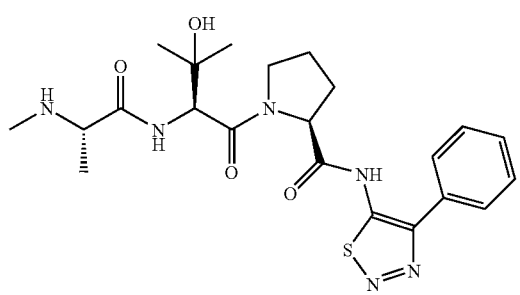
80
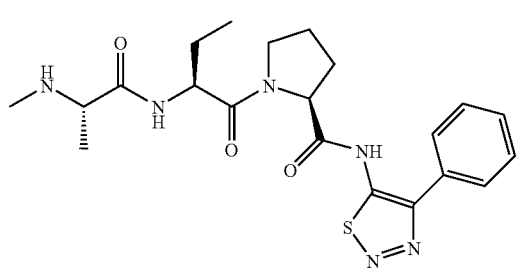
81
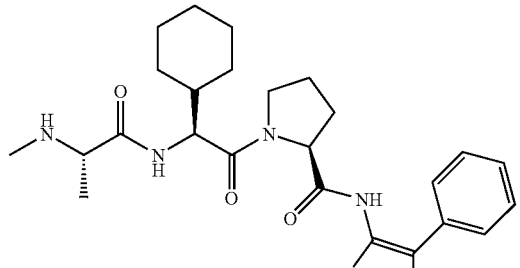
82
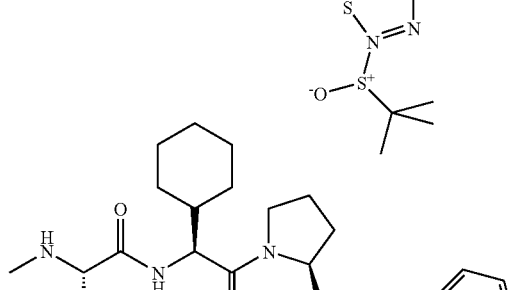
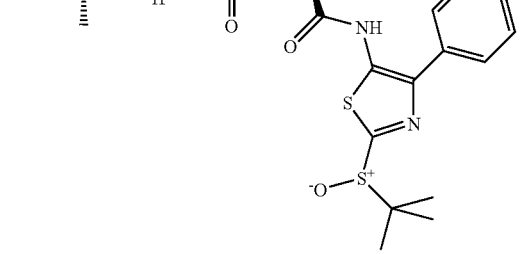

83
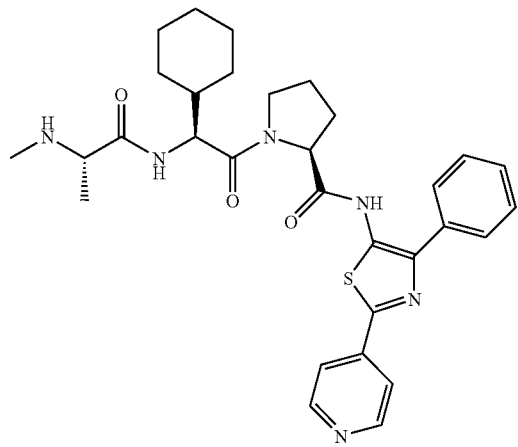
84
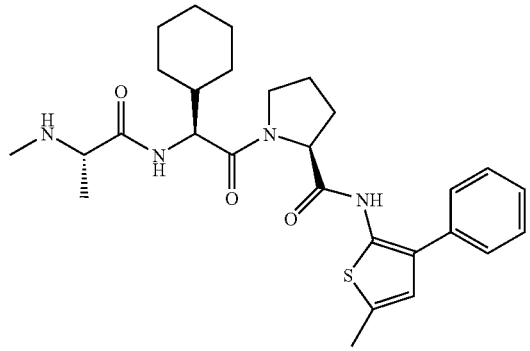
85
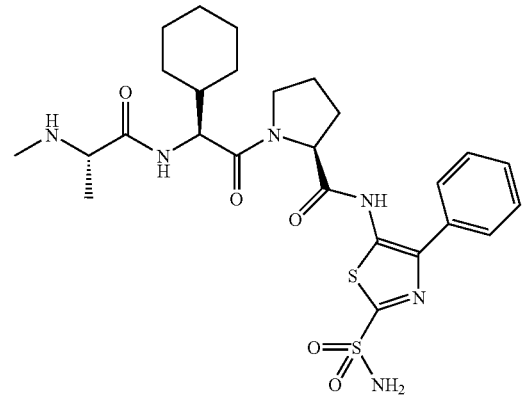
86
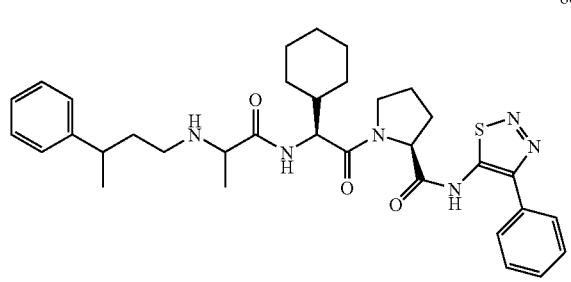
87
88
89
90
91
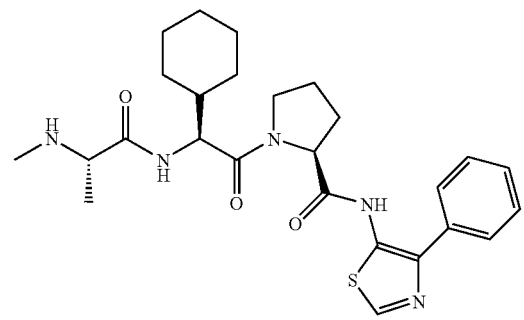
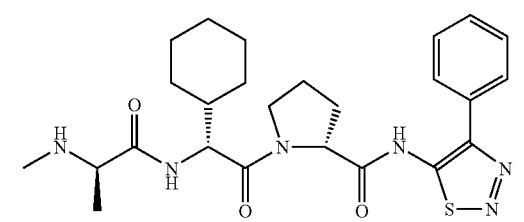

39 40
-continued -continued
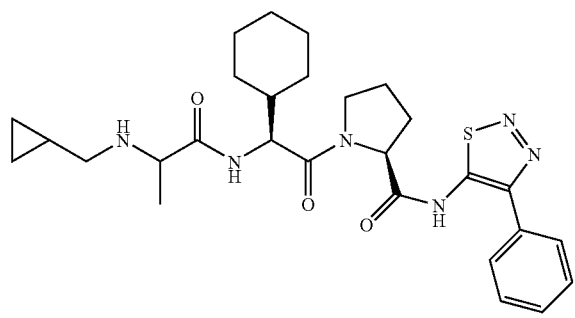
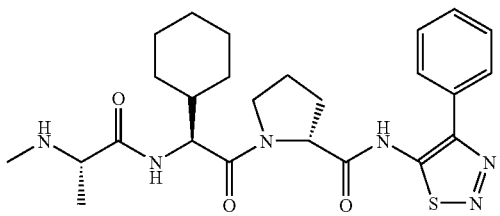
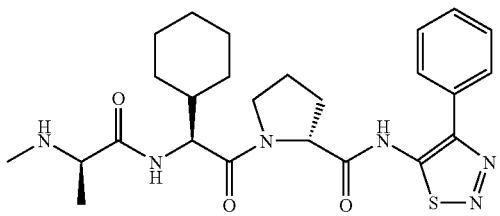
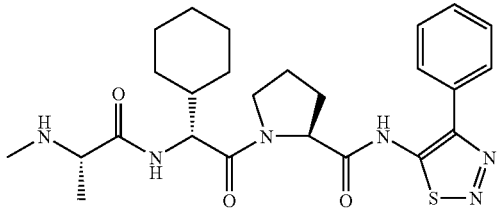
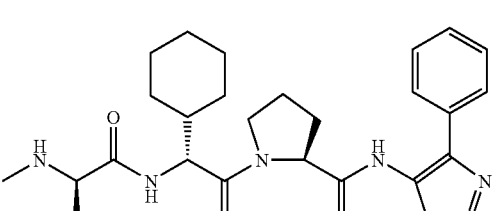
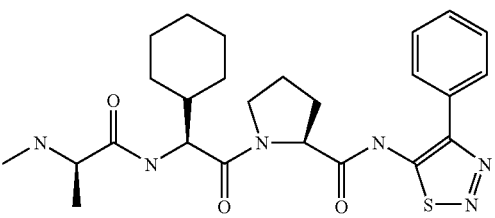
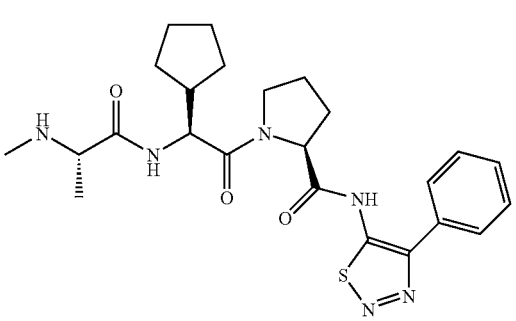

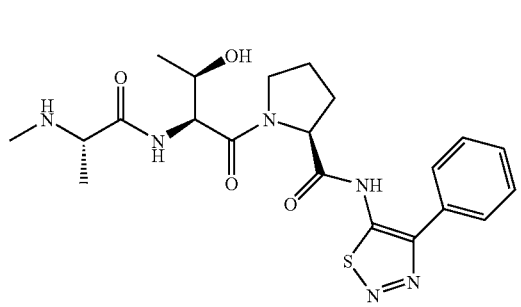
103
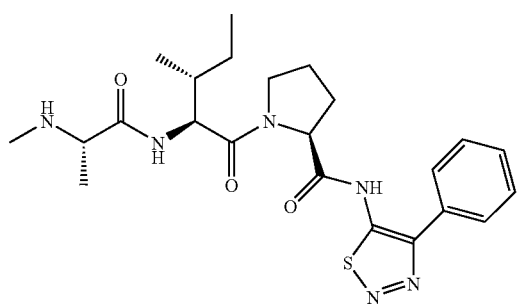
104
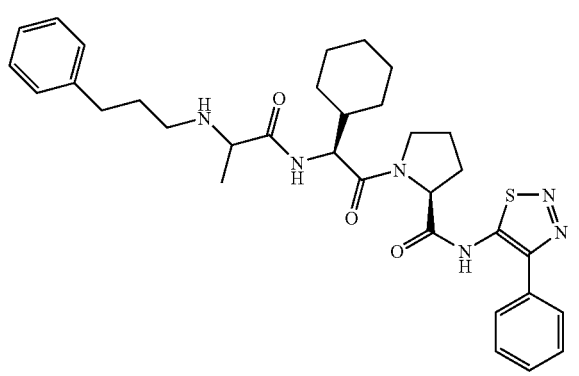
105
106
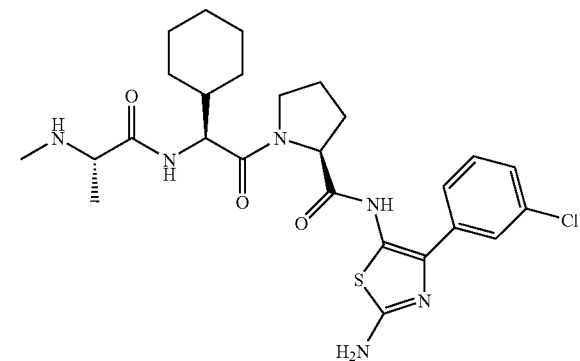
107
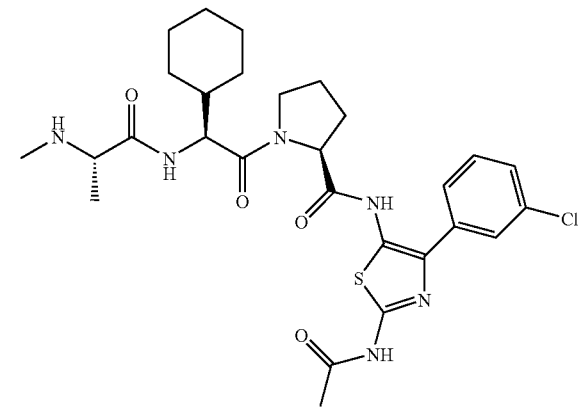
108
109
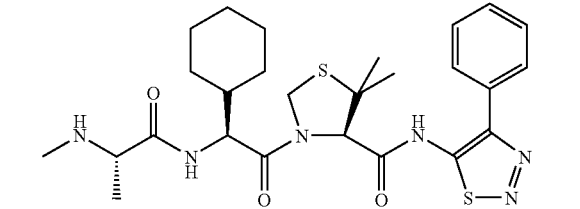
110
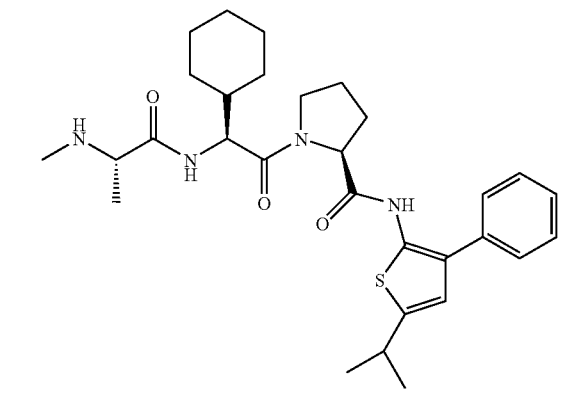

111 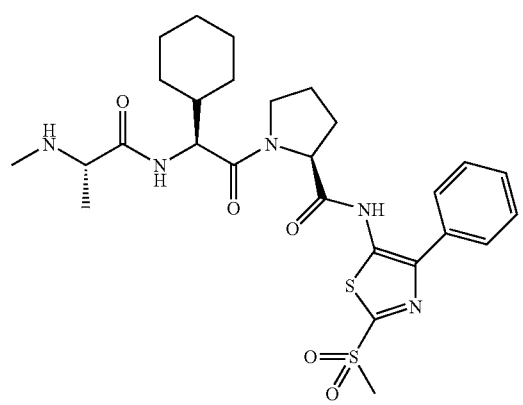
115 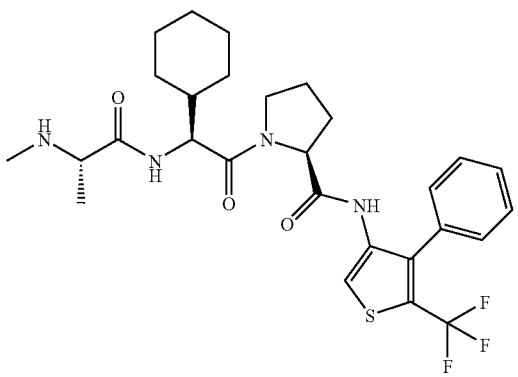
112 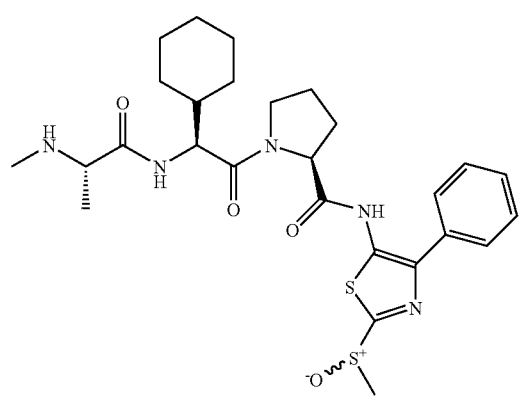
116 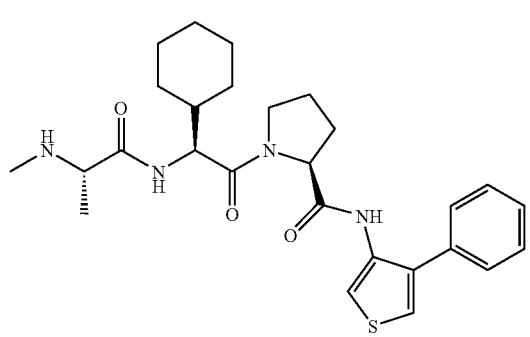
113 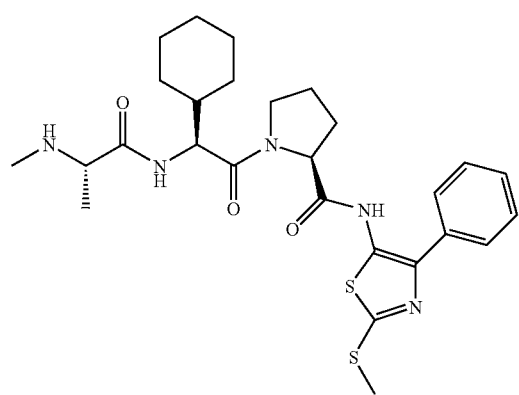
117 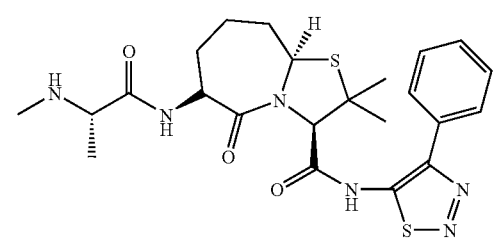
118
114 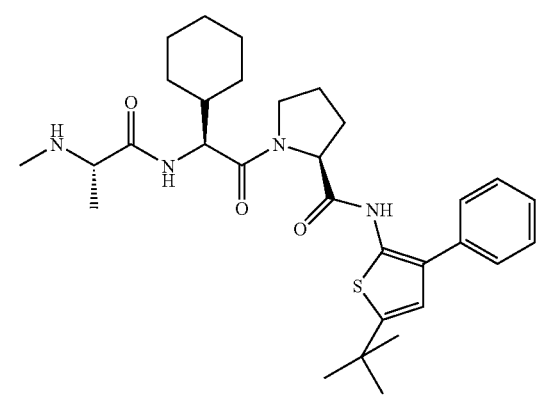
119 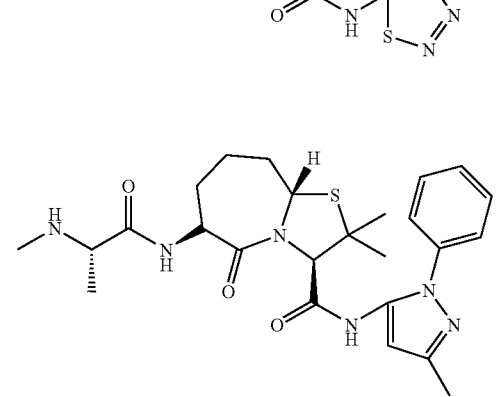

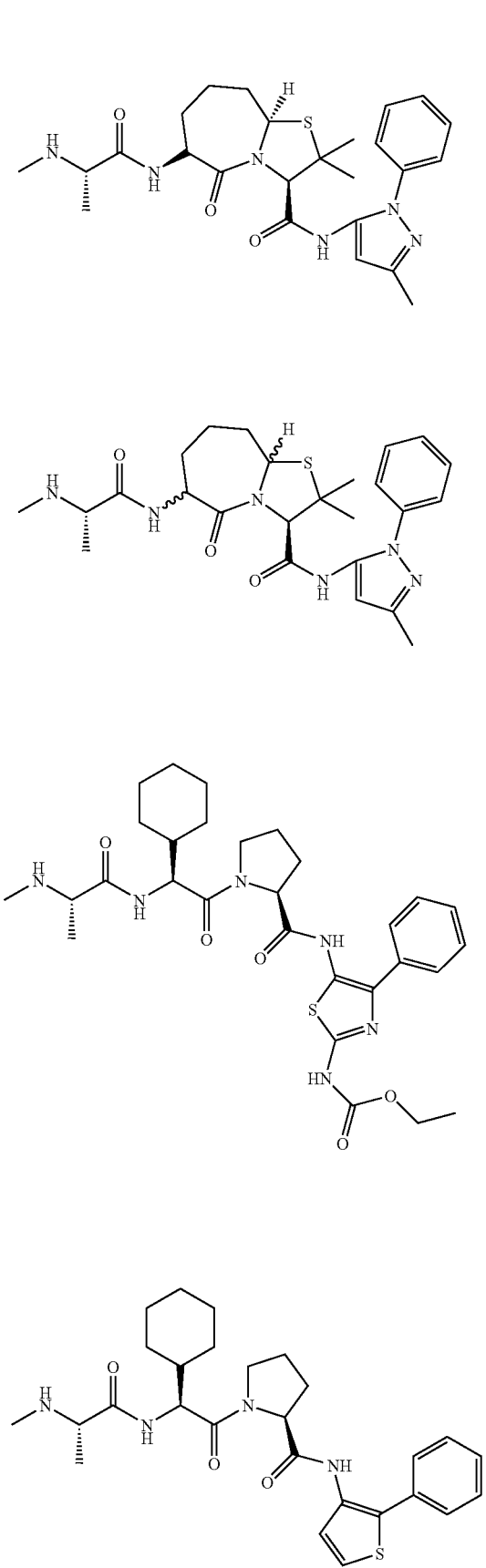
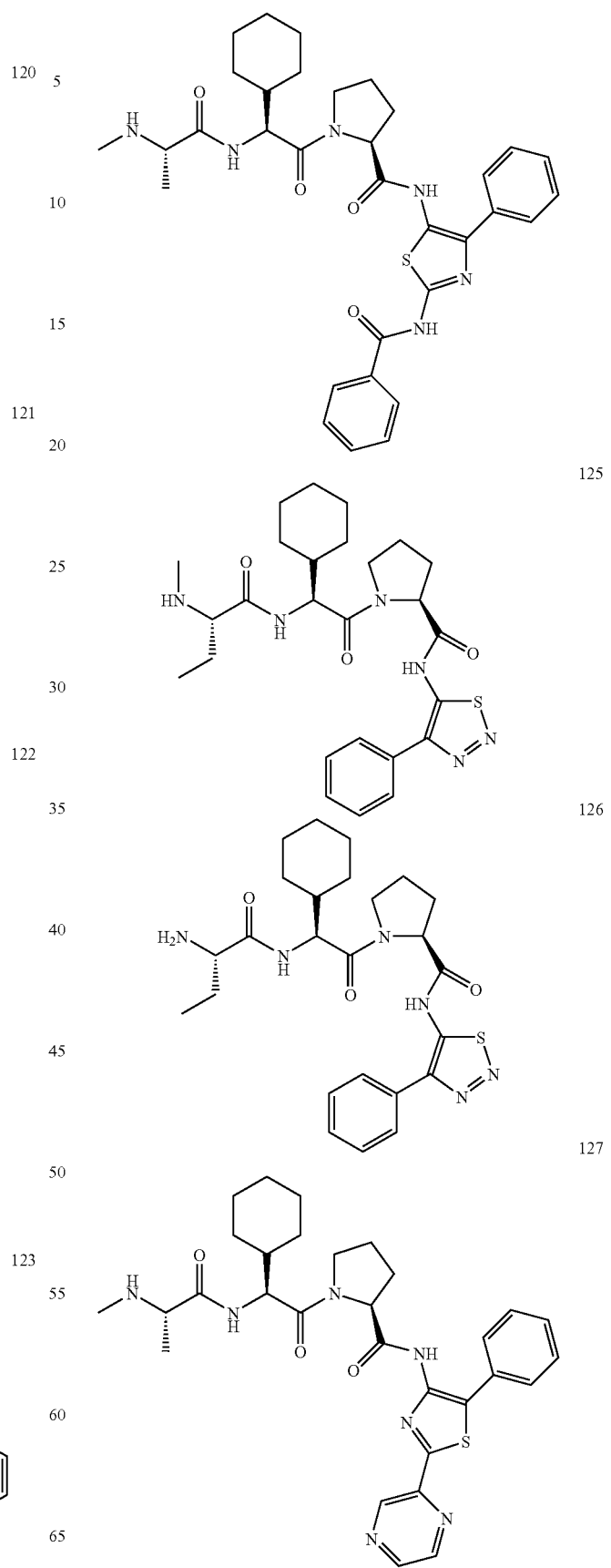

128 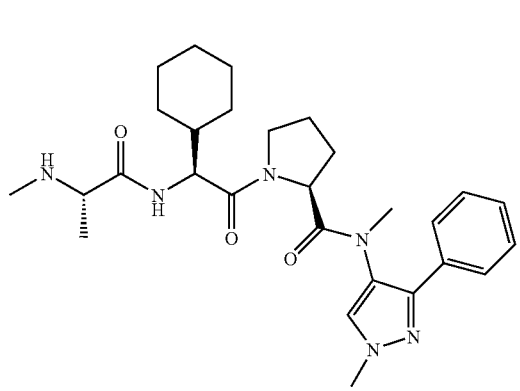
132 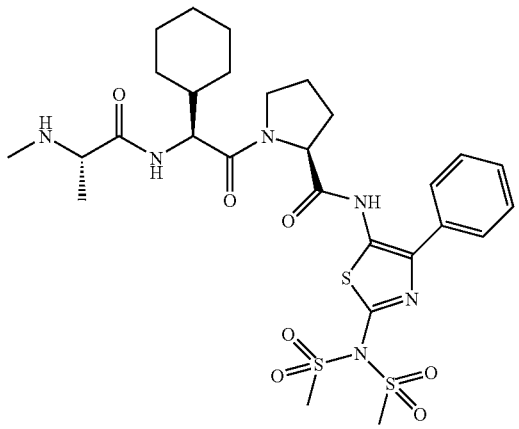
129 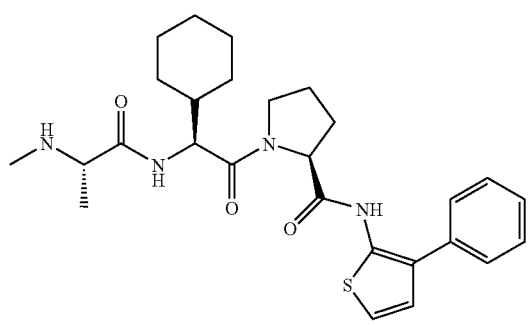
133 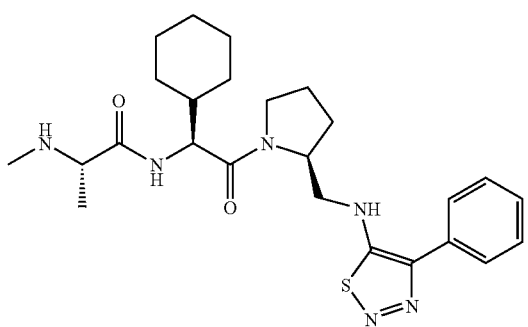
130 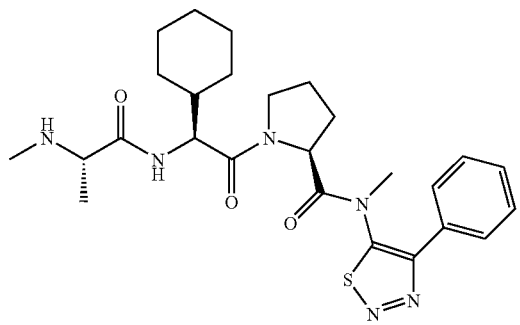
134 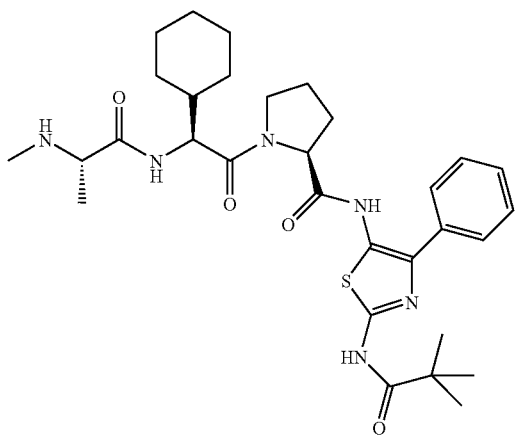
131 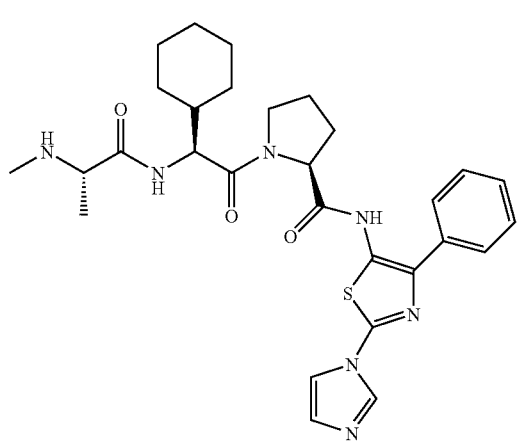
135 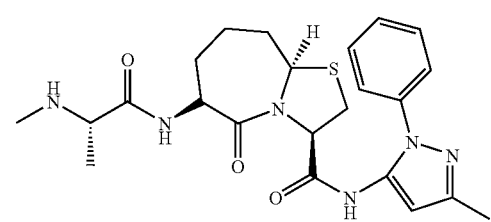

136
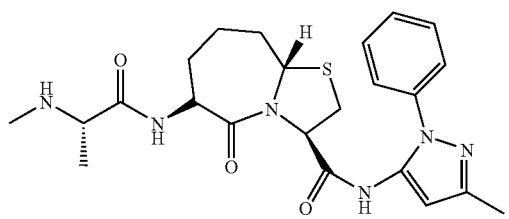
137
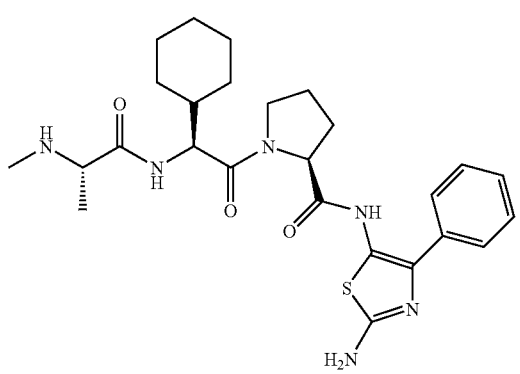
138
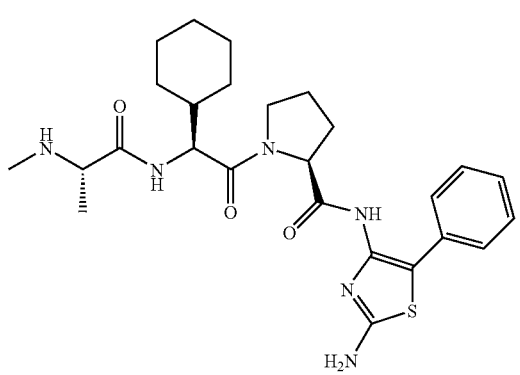
139
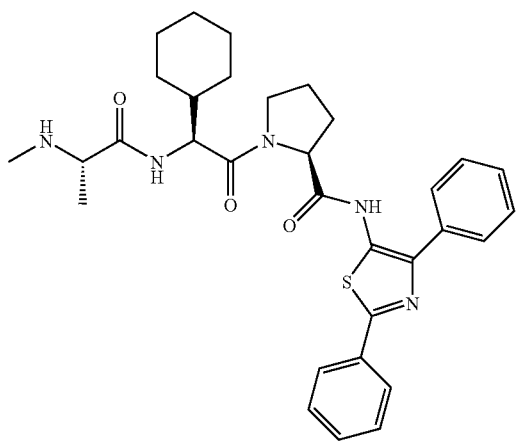
140
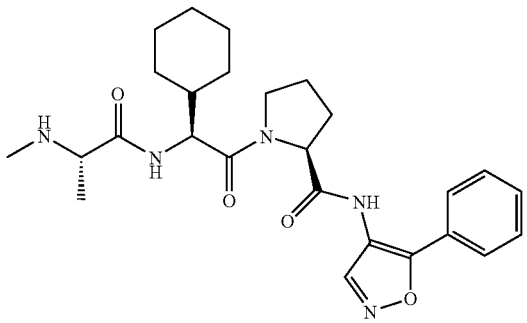
141
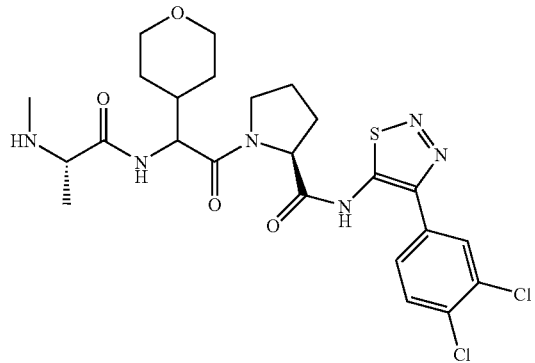
142
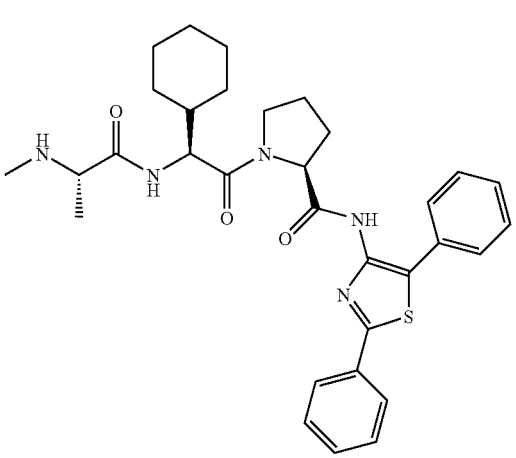
143
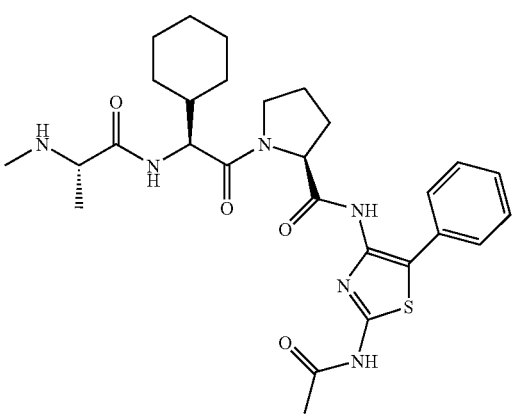

51
-continued
144
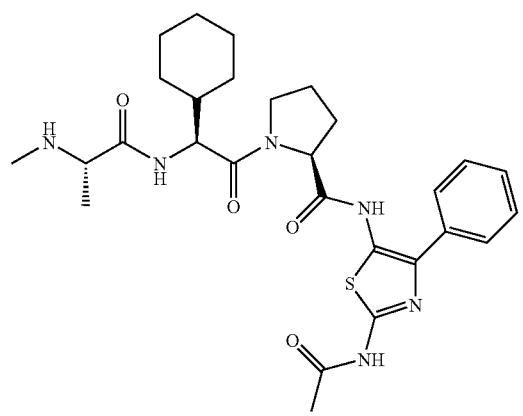
145
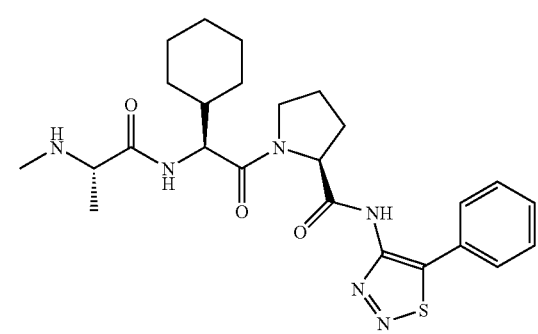
146
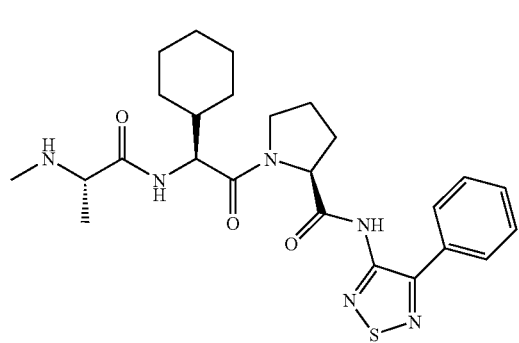
147
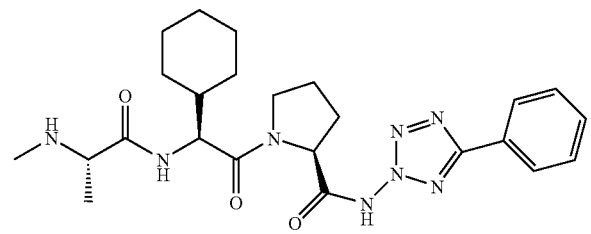
52
-continued
148
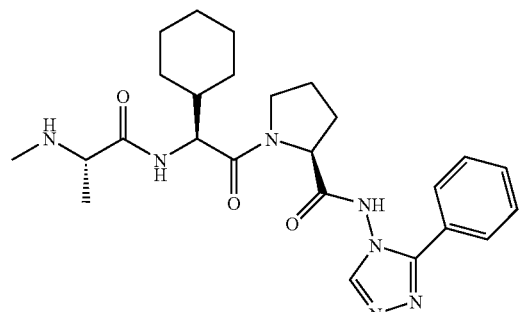
149
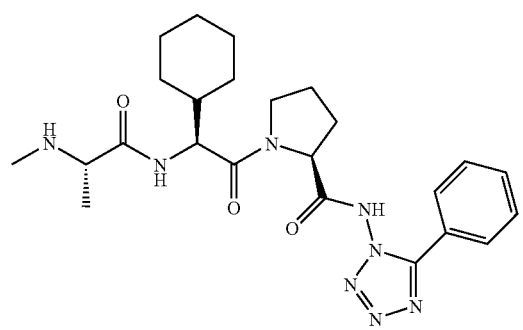
150
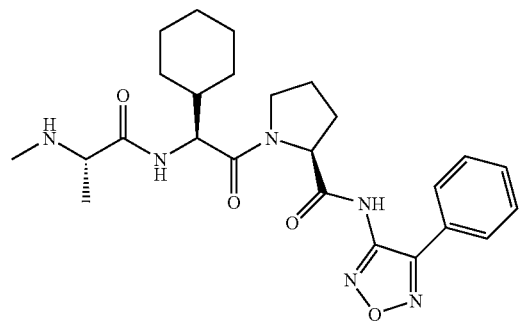
151
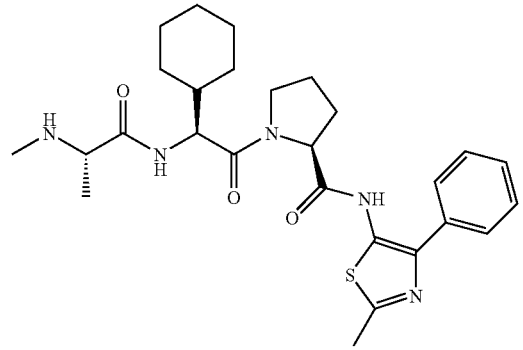

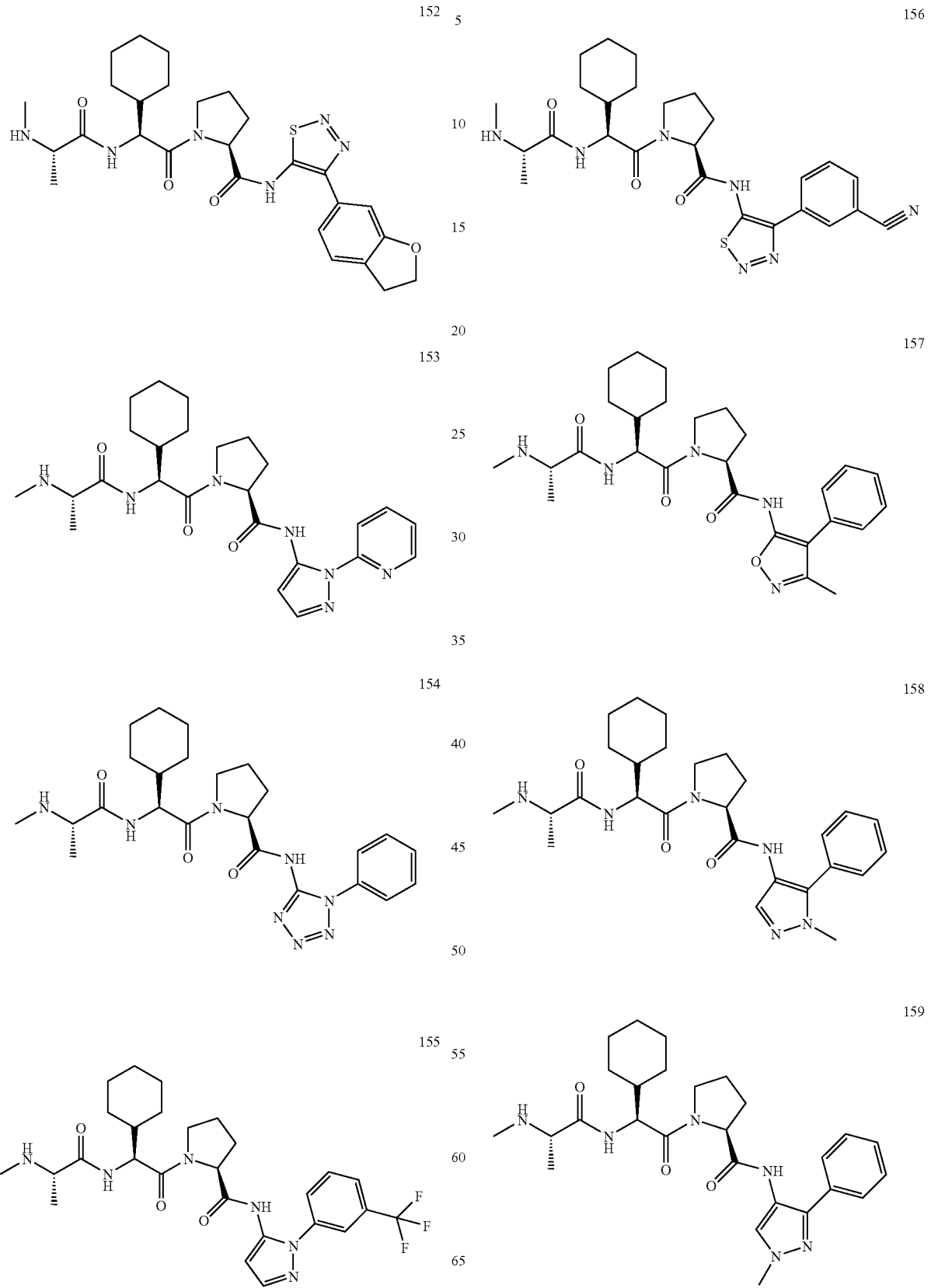

-continued

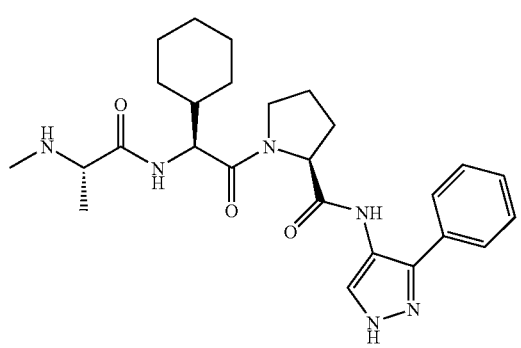
160

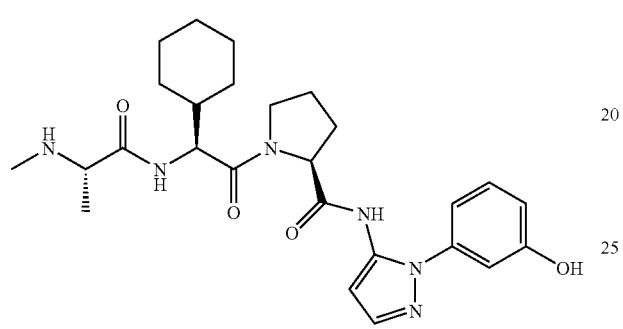
161

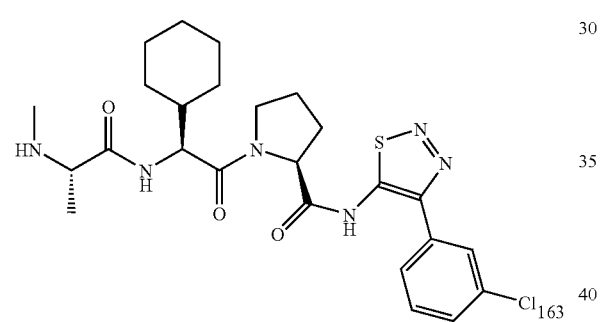
162

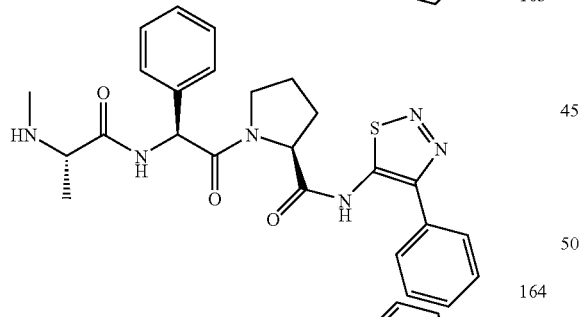
163

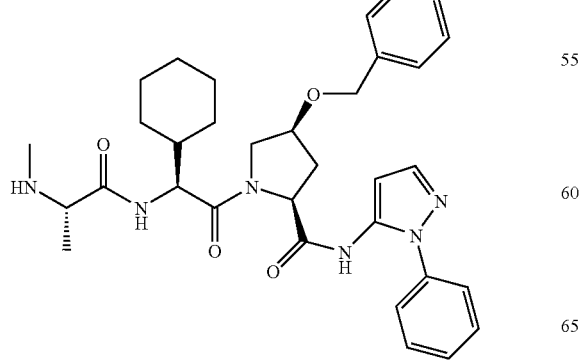
164

-continued

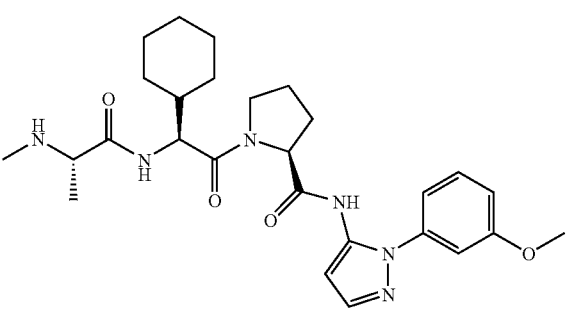
165

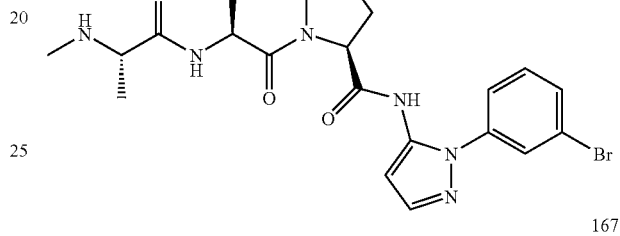
166

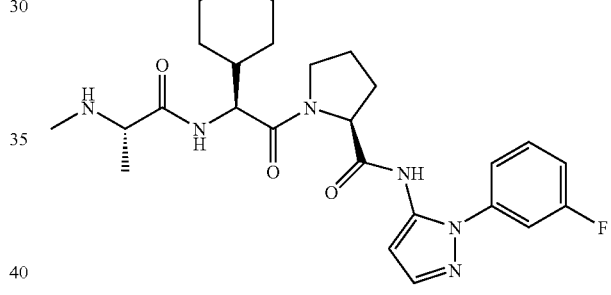
167

Synthesis

Compounds of the invention are prepared using standard organic synthetic techniques from commercially available starting materials and reagents. It will be appreciated that synthetic procedures employed in the preparation of compounds of the invention will depend on the particular substituents present in a compound and that various protection and deprotection may be required as is standard in organic synthesis. In a general synthetic scheme compounds of the invention may be prepared using typical peptide chemistry techniques by coupling the amino acid residue analogues with typical amide coupling procedures. In scheme 1, amine-protected amino acid residue analogues are coupled and deprotected sequentially to give the final compounds.

Scheme 1

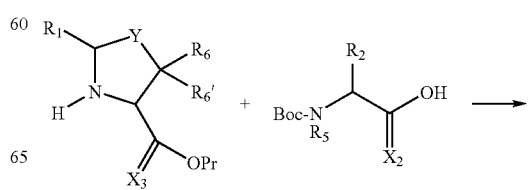

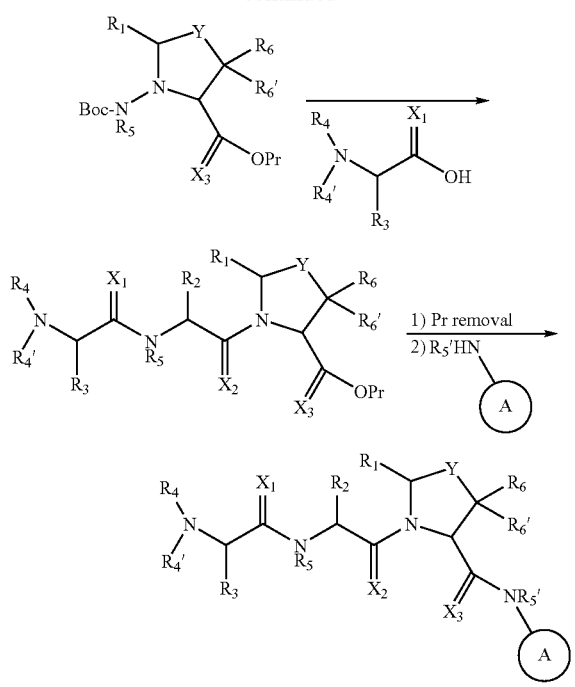

It will be appreciated that the amino acid analogs may be coupled any order and may be prepared using solid phase support which is routine in the art.

Amine substituted ring A which serves as an intermediate for preparing compounds of the invention are commercially available or else are prepared from commercially available reagents employing standard organic chemistry techniques. For example, 1-Aryl-5-aminotetrazoles, such as phenyl-5-aminotetrazole, may be prepared according to scheme 2 from commercially available phenyl thiourea by reacting with sodium azide and mercuric chloride.

Scheme 2

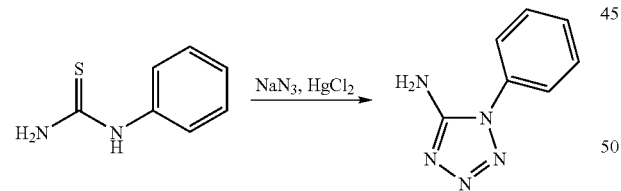

3-Aryl-5-amino-1,2,3-triazoles, such as 3-Phenyl-3H-[1,2,3]triazol-4-ylamine, may be prepared according to the procedures described in J. Org. Chem., 1981, 46:856-9 and illustrated in scheme 3 below by reacting phenylamine with aminoacetonitrile.

Scheme 3

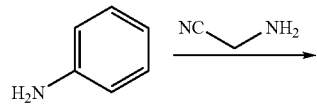

Similarly, 5-Amino-1-phenyl-1H-[1,2,3]triazole-4-carbonitrile may be prepared by reacting phenylamine with 2-amino-malononitrile as illustrated in scheme 4.

Scheme 4

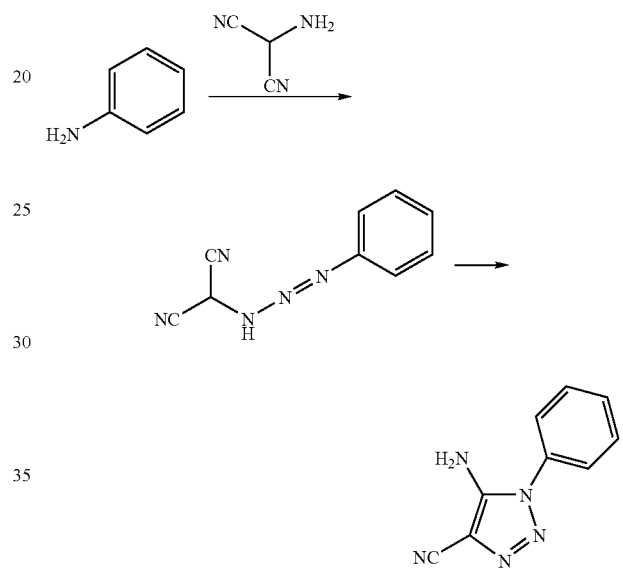

4-Aryl-5-amino-1,2,5-oxadiazoles, such as 4-phenyl-furazan-3-ylamine, may be prepared according to the procedures described in Lakhan et al, (Indian Journal of Chemistry, Section B: Organic Chemistry Including Medicinal Chemistry (1987), 26B(7), 690-2) and illustrated in Scheme 5 by reacting benzoyl cyanide with hydroxylamine.

Scheme 5

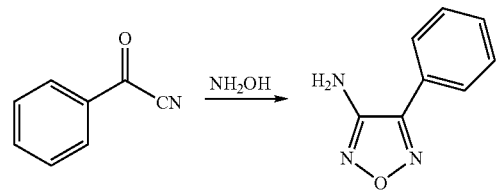

4-Aryl-3-amino-1,2,4-triazoles, such as 4-phenyl-4H-[1,2,4]triazol-3-ylamine, may be prepared by reacting phenylisothiocyanate with hydrazinecarboximidamide to give 5-amino-4-phenyl-4H-[1,2,4]triazole-3-thiol in which the thiol group may be removed with Raney nickel catalyst as illustrated in scheme 6.

Scheme 6

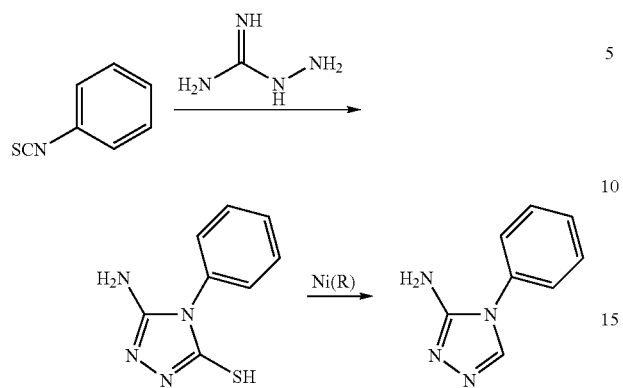

4-Aryl-5-amino-1,2,3-triazoles such as 3,5-diphenyl-3H-[1,2,3]triazol-4-ylamine according to the procedures described in J. Org. Chem., 1990, 55:3351-62 and illustrated in scheme 7, by reacting benzeneacetonitrile with azidobenzene (or alternatively trimethylsilylazide, TMS-$N_3$).

Scheme 7

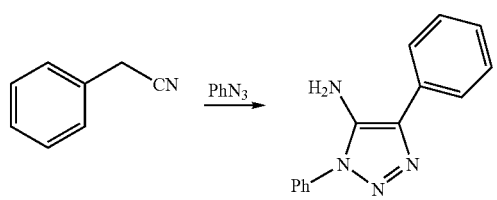

4-Aryl-3-aminopyrazoles such as 4-phenyl-2H-pyrazol-3-ylamine may be prepared according to the procedures described in patent EP269,859 and illustrated in scheme 8, by reacting benzeneacetonitrile with orthoformic acid triethyl ester to give 3-oxo-2-phenyl-propionitrile which is reacted with hydrazine.

Scheme 8

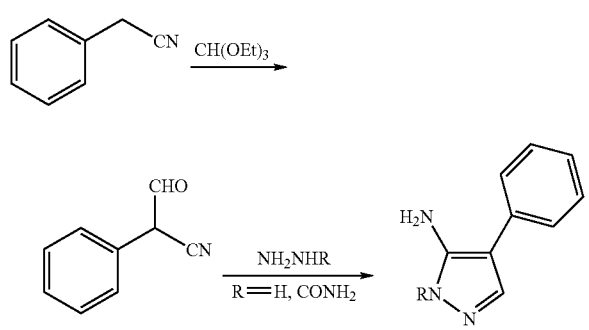

Various hydrazines and derivatives of benzeneacetonitrile can be used to prepare substituted-4-aryl-3-aminopyrazoles as illustrated in scheme 9.

Scheme 9

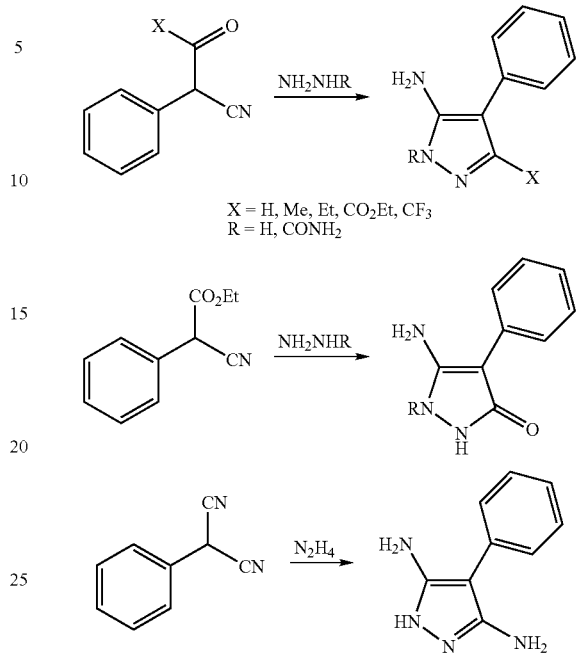

1-Aryl-5-aminopyrazoles such as 2-phenyl-2H-pyrazol-3-ylamine may be prepared by reacting phenylhydrazine with 3-oxo-propionitrile. Various nitriles can be used to introduce substitution at the 3-position of the pyrazole ring as illustrated in scheme 10.

Scheme 10

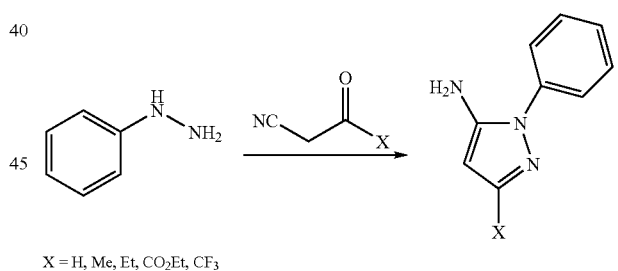

X = H, Me, Et, $CO_2Et$, $CF_3$

3-Aryl-4-aminoimidazoles such as 3-phenyl-3H-imidazol-4-ylamine may be prepared by reacting phenylamine with aminoacetonitrile and orthoformic acid triethyl ester as illustrated in scheme 11. Substitution at the 2-position of the imidazole can be introduced using analogs of the orthoformic acid triethylester as follows.

Scheme 11

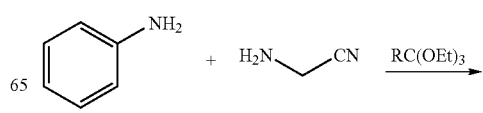

-continued

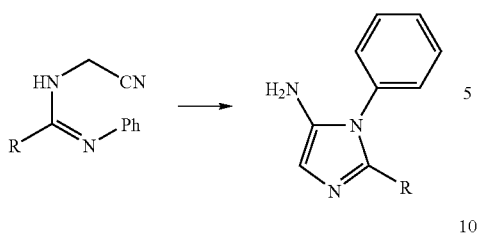

5-Aryl-4-aminoimidazoles such as 5-phenyl-3H-imidazol-4-ylamine may be prepared by reacting formamidine with aminophenylacetonitrile as illustrated in scheme 12. Substitution at the 2-position of the imidazole ring can be introduced using analogs of the formamidine.

Scheme 12

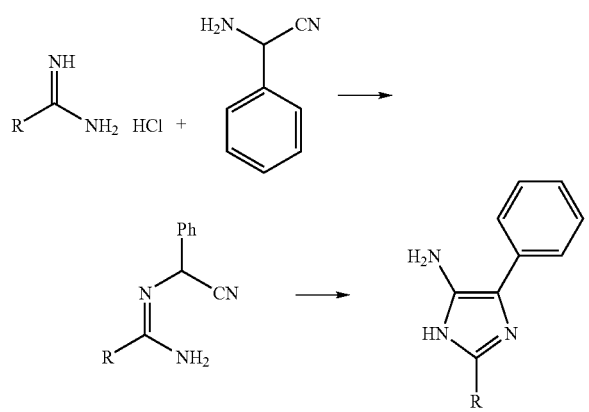

4-Aryl-[1,2,3]thiadiazol-5-ylamines such as 4-phenyl-[1,2,3]thiadiazol-5-ylamine may be prepared by procedure illustrated in scheme 13. 2-bromo-1-phenyl-ethanone is reacted with lithium phthalimide and the substitution product is reacted with hydrazinecarboxylate ethyl ester. The resulting hydrazinecarboxylate ethyl ester is cyclized to form a thiadiazole by reacting with thionyl chloride followed by removal of the phthalimide group with hydrazine.

Scheme 13

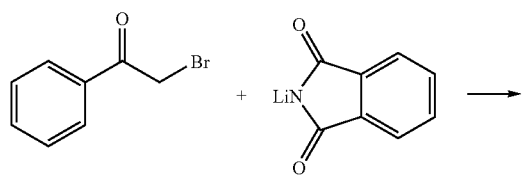

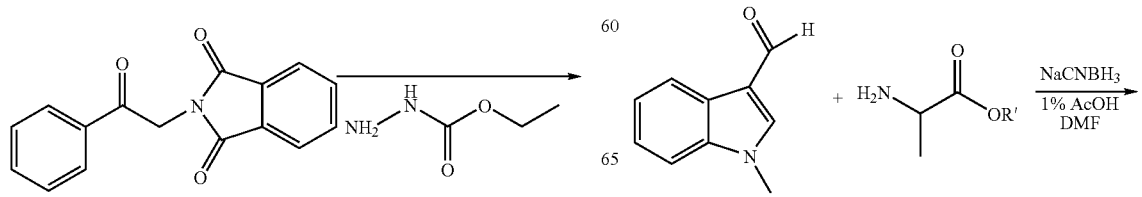

-continued

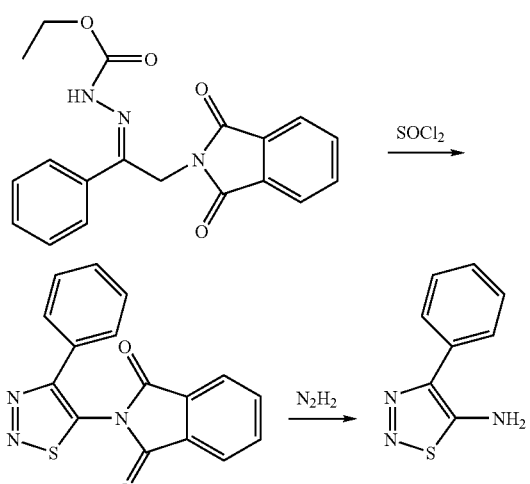

Compounds of the invention in which $R_4$ or $R_4'$ are other than H may be prepared according to standard organic chemistry techniques, for example by reductive amination in which a starting amino acid residue analog e.g. $NH_2$—$CH(R_3)$—$C(O)$—OH is reacted with a suitable aldehyde or ketone to give the desired $R_4$ and $R_4'$ substituents. See scheme 14. The resulting $R_4/R_4'$ substituted amino acid intermediate can then be conjugated to the next amino acid intermediate or the remainder of the compound using standard peptide coupling procedures.

Scheme 14

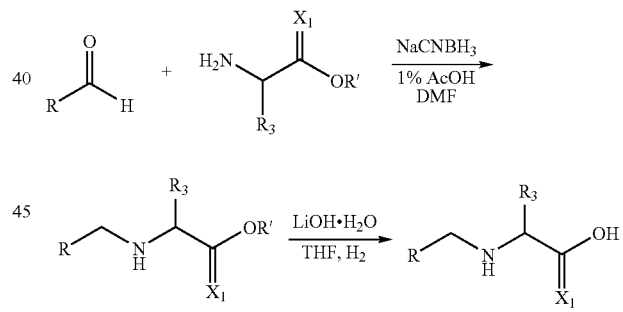

In a particular embodiment, alanine is reacted with 1-methylindole-2-carboxaldehyde and reduced with sodium cyanoborohydride dissolved in 1% HOAc/DMF to give the N-substituted alanine residue which may be used in preparing compounds of the invention. See scheme 15.

Scheme 15

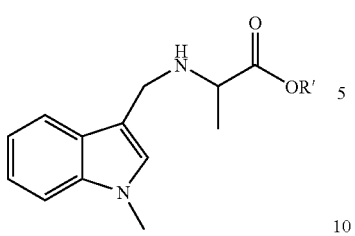

Alternatively, the reductive amination procedure to introduce R$_4$/R$_4$' substituents is the final step in the preparation of the compound.

When compounds of the invention incorporate R$_4$ or R$_4$' substituents other than H, they may also be prepared by substitution of a suitable acid intermediate which incorporates a leaving group with a desired amine. For example Br—CH(R$_3$)—C(O)—OH is substituted with an amine R$_4$—NH$_2$ or R$_4$—NH—R$_4$' according to scheme 16.

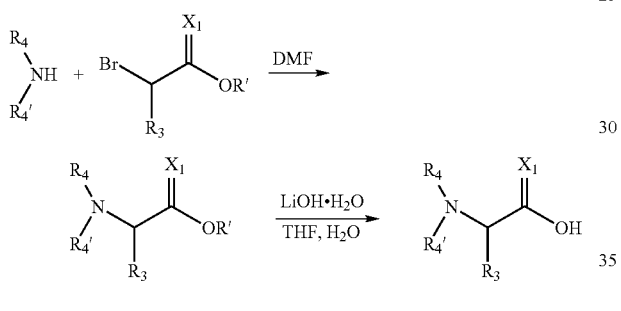

Scheme 16

Alternatively, the substitution reaction introducing R$_4$ or R$_4$' substituents may be performed as a final step in the preparation of the compound as illustrated in scheme 17.

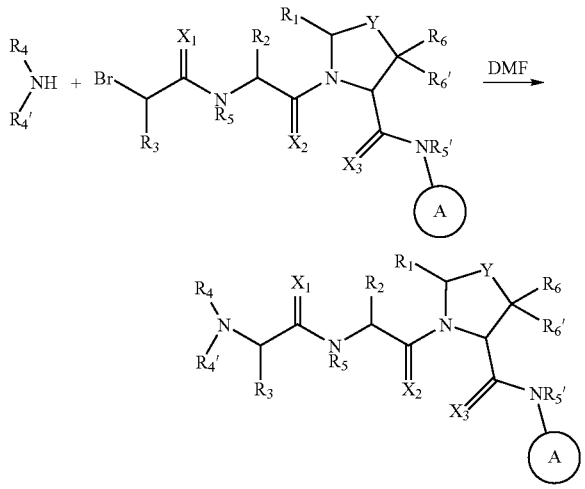

In a particular embodiment, 2-bromopropionic acid is reacted with the following amines dissolved in DMF and bubbled for until substitution is complete to form N-substituted alanine residues:

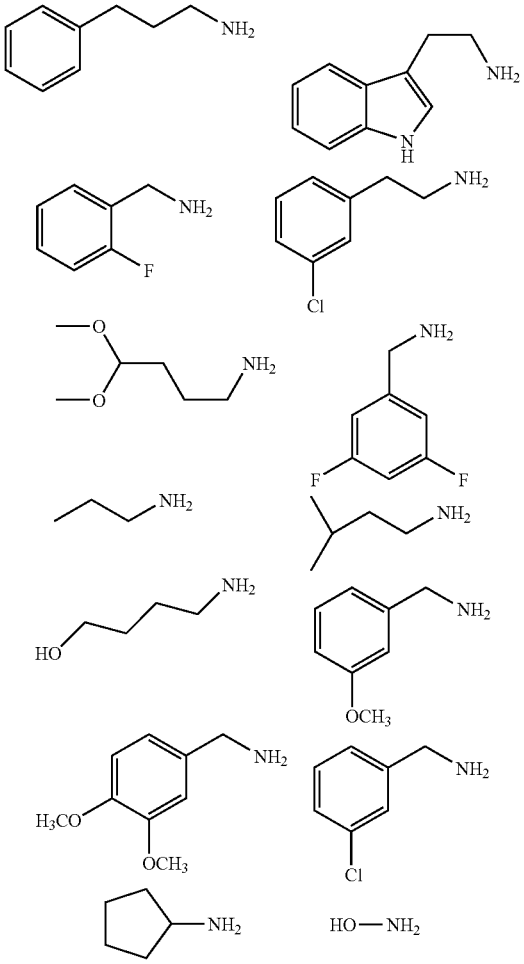

Compounds of the invention in which any one or more of X$_1$, X$_2$ and X$_3$ are sulfur, i.e. the compound incorporates a thioamide, may be prepared according to established organic chemistry techniques. For example, compounds in which X$_2$ is sulfur can be prepared according to scheme 18 starting from an Fmoc protected amino acid residue analog NH$_2$—CH(R$_2$)—COOH which is dissolved in THF and cooled to −25° C., with addition of DIPEA followed by addition of isobutyl-chloroformate. After 10 minutes, the diamine, 4-nitrobenzene-1,2-diamine, is added and the reaction mixture is continuously stirred at −25° C. for 2 hours, then at room temperature overnight. THF is vacuumed off and the mixture is then subjected to flash chromatography using 50% EtOAc/Hexane to yield the product. The Fmoc-alanine derivative, phosphorus pentasulfide and sodium carbonate are mixed in THF and stirred overnight. The solution is concentrated and direct chromatography using 80% EtOAc/Hexane yields the activated thioalanine. The activated thioalanine and sodium nitrite are then mixed in acetic acid and diluted with H$_2$O. The resulting precipitant is filtered and dried to yield the product. The thioalanine is coupled to an OH-protected proline amino acid residue analog by dissolving both in DMF. The thioamide product may then be deprotected with 20% PIP/DMA for 15 minutes and used to conjugate to the R$_4$/R$_4$'-N—CH(R$_3$)—COOH amino acid residue analog followed by OH-deprotection and coupling to an amino-substituted A ring intermediate. Alternatively the Fmoc-protected thioamide is first coupled to an amino substituted A ring intermediate followed by Fmoc deprotection and subsequent coupling to the R$_4$/R$_4$'—N—CH(R$_3$)—COOH amino acid residue analog.

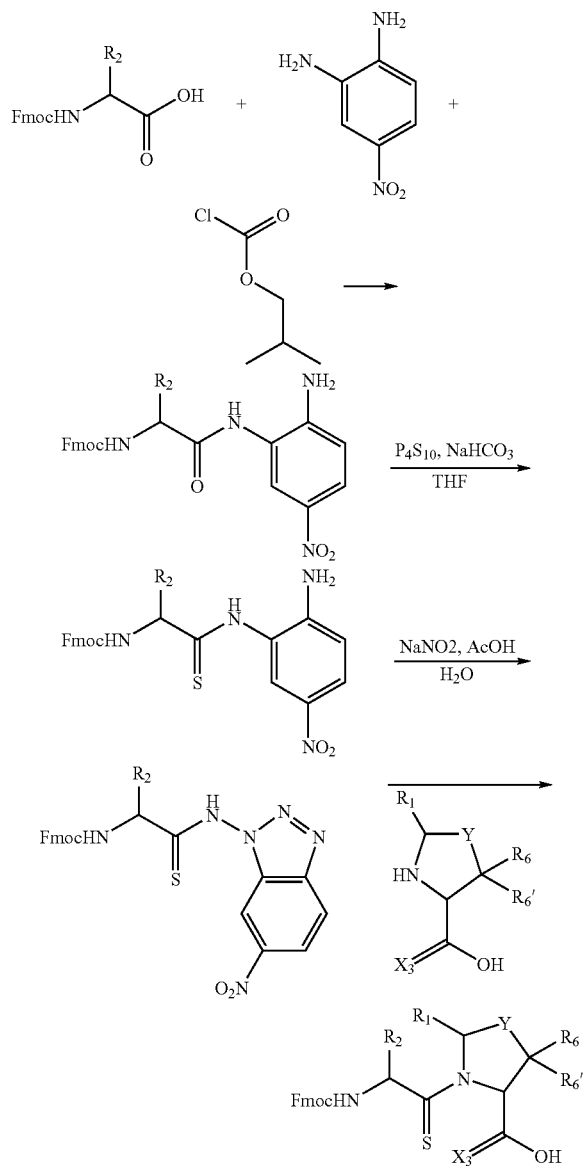

Scheme 18

Utility

The compounds of the invention inhibit the binding of IAP proteins to caspases, in particular X-IAP binding interaction with caspases 3 and 7. The compounds also inhibit the binding of ML-IAP to Smac protein. Accordingly, the compounds of the invention are useful for inducing apoptosis in cells or sensitizing cells to apoptotic signals, in particular cancer cells. Compounds of the invention are useful for inducing apoptosis in cells that overexpress IAP proteins. Alternatively, compounds of the invention are useful for inducing apoptosis in cells in which the mitochondrial apoptotic pathway is disrupted such that release of Smac from ML-IAP proteins is inhibited, for example by up regulation of Bcl-2 or down regulation of Bax/Bak. More broadly, the compounds can be used for the treatment of all cancer types which fail to undergo apoptosis. Examples of such cancer types include neuroblastoma, intestine carcinoma such as rectum carcinoma, colon carcinoma, familiary adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroidea carcinoma, papillary thyroidea carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyo sarcoma, craniopharyngeoma, osteosarcoma, chondrosarcoma, myosarcoma, liposarcoma, fibrosarcoma, Ewing sarcoma and plasmocytoma.

Compounds of the invention are useful for sensitizing cells to apoptotic signals. Accordingly, the compounds may be administered prior to, concomitantly with, or following administration of radiation therapy or cytostatic or antineoplastic chemotherapy. Suitable cytostatic chemotherapy compounds include, but are not limited to (i) antimetabolites, such as cytarabine, fludarabine, 5-fluoro-2'-deoxyuiridine, gemcitabine, hydroxyurea or methotrexate; (ii) DNA-fragmenting agents, such as bleomycin, (iii) DNA-crosslinking agents, such as chlorambucil, cisplatin, cyclophosphamide or nitrogen mustard; (iv) intercalating agents such as adriamycin (doxorubicin) or mitoxantrone; (v) protein synthesis inhibitors, such as L-asparaginase, cycloheximide, puromycin or diphtheria toxin; (Vi) topoisomerase I poisons, such as camptothecin or topotecan; (vii) topoisomerase II poisons, such as etoposide (VP-16) or teniposide; (viii) microtubule-directed agents, such as colcemid, colchicine, paclitaxel, vinblastine or vincristine; (ix) kinase inhibitors such as flavopiridol, staurosporin, STI571 (CPG 57148B) or UCN-01 (7-hydroxystaurosporine); (x) miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; (xi) hormones such as glucocorticoids or fenretinide; (xii) hormone antagonists, such as tamoxifen, finasteride or LHRH antagonists. In a preferred embodiment, compounds of the present invention are coadministered with a cytostatic compound selected from the group consisting of cisplatin, doxorubicin, taxol, taxotere and mitomycin C. Most preferred, the cytostatic compound is doxorubicin.

Another class of active compounds which can be used in the present invention are those which are able to sensitize for or induce apoptosis by binding to death receptors ("death receptor agonists"). Such agonists of death receptors include death receptor ligands such as tumor necrosis factor a (TNF-α), tumor necrosis factor β (TNF-β, lymphotoxin-α), LT-β (lymphotoxin-β), TRAIL (Apo2L, DR4 ligand), CD95 (Fas, APO-1) ligand, TRAMP (DR3, Apo-3) ligand, DR6 ligand as well as fragments and derivatives of any of said ligands. Preferably, the death receptor ligand is TNF-α. More preferably the death receptor ligand is Apo2L/TRAIL. Furthermore, death receptors agonists comprise agonistic antibodies to death receptors such as anti-CD95 antibody, anti-TRAIL-R1 (DR4) antibody, anti-TRAIL-R2 (DR5) antibody, anti-TRAIL-R3 antibody, anti-TRAIL-R4 antibody, anti-DR6 antibody, anti-TNF-R1 antibody and anti-TRAMP (DR3) antibody as well as fragments and derivatives of any of said antibodies.

For the purpose of sensitizing cells for apoptosis, the compounds of the present invention can be also used in combination with radiation therapy. The phrase "radiation therapy" refers to the use of electromagnetic or particulate radiation in the treatment of neoplasia. Radiation therapy is based on the principle that high-dose radiation delivered to a target area will result in the death of reproducing cells in both tumor and normal tissues. The radiation dosage regimen is generally defined in terms of radiation absorbed dose (rad), time and fractionation, and must be carefully defined by the oncologist. The amount of radiation a patient receives will depend on various consideration but the two most important considerations are the location of the tumor in relation to other critical structures or organs of the body, and the extent to which the tumor has spread. Examples of radiotherapeutic agents are provided in, but not limited to, radiation therapy and is known in the art (Hellman, Principles of Radiation Therapy, Cancer, in Principles I and Practice of Oncology, 24875 (Devita et al., 4th ed., vol 1, 1993). Recent advances in radiation therapy include three-dimensional conformal external beam radiation, intensity modulated radiation therapy (IMRT), stereotactic radiosurgery and brachytherapy (interstitial radiation therapy), the latter placing the source of radiation directly into the tumor as implanted "seeds". These newer treatment modalities deliver greater doses of radiation to the tumor, which accounts for their increased effectiveness when compared to standard external beam radiation therapy.

Ionizing radiation with beta-emitting radionuclides is considered the most useful for radiotherapeutic applications because of the moderate linear energy transfer (LET) of the ionizing particle (electron) and its intermediate range (typically several millimeters in tissue). Gamma rays deliver dosage at lower levels over much greater distances. Alpha particles represent the other extreme, they deliver very high LET dosage, but have an extremely limited range and must, therefore, be in intimate contact with the cells of the tissue to be treated. In addition, alpha emitters are generally heavy metals, which limits the possible chemistry and presents undue hazards from leakage of radionuclide from the area to be treated. Depending on the tumor to be treated all kinds of emitters are conceivable within the scope of the present invention.

Furthermore, the present invention encompasses types of non-ionizing radiation like e.g. ultraviolet (UV) radiation, high energy visible light, microwave radiation (hyperthermia therapy), infrared (IR) radiation and lasers. In a particular embodiment of the present invention UV radiation is applied.

The invention also includes pharmaceutical compositions or medicaments containing the compounds of the invention and a therapeutically inert carrier, diluent or excipient, as well as methods of using the compounds of the invention to prepare such compositions and medicaments. Typically, the compounds of formula I used in the methods of the invention are formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. Formulation in an acetate buffer at pH 5 is a suitable embodiment.

The inhibitory compound for use herein is preferably sterile. The compound ordinarily will be stored as a solid composition, although lyophilized formulations or aqueous solutions are acceptable.

The composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit IAP interaction with caspases, induce apoptosis or sensitize a malignant cell to an apoptotic signal. Such amount is preferably below the amount that is toxic to normal cells, or the mammal as a whole.

Generally, the initial pharmaceutically effective amount of the compound of the invention administered parenterally per dose will be in the range of about 0.01-100 mg/kg, preferably about 0.1 to 20 mg/kg of patient body weight per day, with the typical initial range of compound used being 0.3 to 15 mg/kg/day. Oral unit dosage forms, such as tablets and capsules, preferably contain from about 25 to about 1000 mg of the compound of the invention.

The compound of the invention may be administered by any suitable means, including oral, topical, transdermal, parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution is typically filtered, e.g. using a 0.2 micron filter, to remove impurities and contaminants.

EXAMPLES

The invention will be more fully understood by reference to the following examples. They should not, however, be construed as limiting the scope of the invention. Abbreviations used herein are as follows:
ACN: acetonitrile;
Chg: cyclohexylglycine;
DCM: dichloromethane
DIPEA: diisopropylethylamine;
DMAP: 4-dimethylaminopyridine;
DME: 1,2-dimethoxyethane;
DMF: dimethylformamide;
DMSO: dimethylsulfoxide
EDC: 1-ethyl-3-(3-dimethylaminopropyl)carbodiimide;

EEDQ: 2-ethoxy-1-ethoxycarbonyl-1,2-dihydroquinoline

LCMS: liquid chromatography mass spectrometry;

HATU: O-(7-Azobenzotriazol-1-yl)-1,1,3,3-tetramethyluronium hexafluorophosphate;

HOBt: N-Hydroxybenzotriazole

HBTU: 2-(1H-Benzotriazol-1-yl)-1,1,3,3-Tetramethyl-uronium Hexafluorophosphate

HPLC: high performance liquid chromatography;

NBS: N-bromosuccinamide;

TASF: tris(dimethylamino)sulfonium difluorotrimethylsilicate;

TEA: triethylamine;

TFA: trifluoroacetate;

THF: tetrahydrofuran;

Example 1

6-(1,3-Dioxo-1,3-dihydro-isoindol-2-yl)-5-oxo-octahydro-thiazolo[3,2-a]azepine-3-carboxylic acid ethyl ester

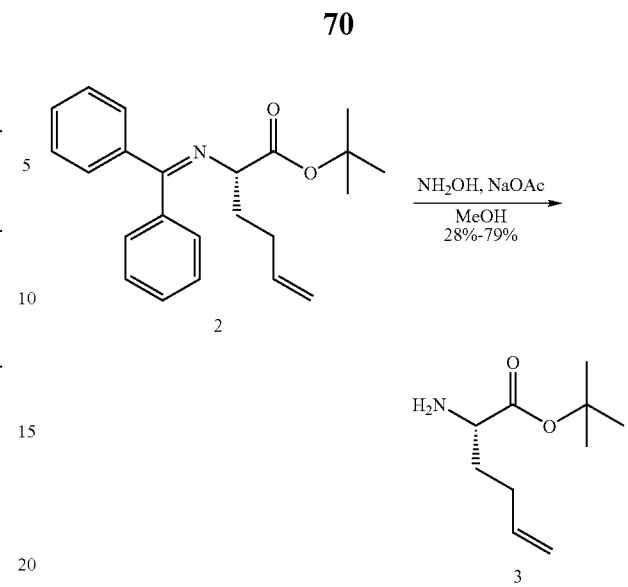

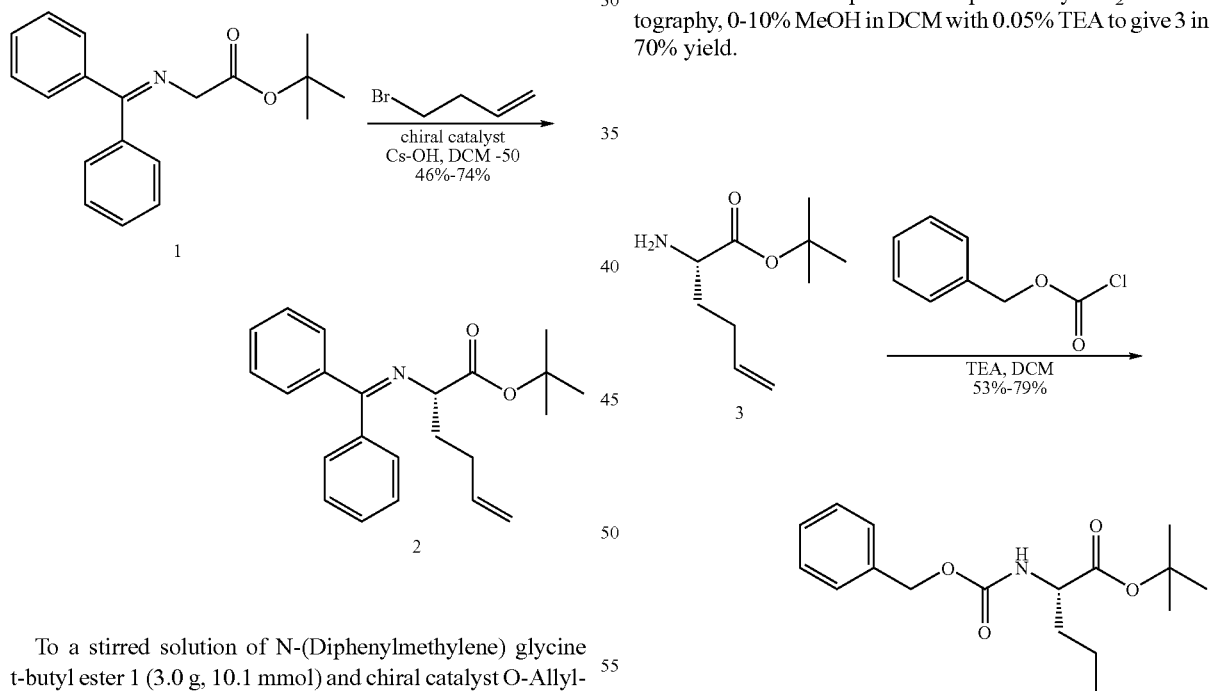

To a stirred solution of N-(Diphenylmethylene) glycine t-butyl ester 1 (3.0 g, 10.1 mmol) and chiral catalyst O-Allyl-N-(9-anthracenylmethyl)-cinchonidium bromide (613 mg, 1.0 mmol) in dry DCM (30 mL) was added cesium hydroxide (17 g, 101 mmol). The reaction was cooled to −78° C. in a dry ice acetone bath and 4-bromo-1-butene was added dropwise. After addition the reaction was stirred vigorously under $N_2$ at −48° C. for 48 hours. Ethyl ether was added followed by $H_2O$. The organic layer was separated and washed 2× with $H_2O$, 1× brine, dried with $MgSO_4$ and concentrated. The product was purified by $SiO_2$ chromatography over a gradient of 0-10% EtOAc in Hexanes to give 2 in 65% yield.

To a stirred solution of 2 (1.52 g, 4.3 mmol) in dry MeOH (50 mL) was added NaOAc (720 mg, 8.6 mmol) and $NH_2OH.HCl$ (540 mg, 7.6 mmol). Stirred under $N_2$ at room temperature for 2 hours. DCM and 0.1 N NaOH were added. The aqueous layer was separated and extracted 3× with DCM, dried with $Na_2SO_4$ and the DCM fractions were combined and concentrated. The product was purified by $SiO_2$ chromatography, 0-10% MeOH in DCM with 0.05% TEA to give 3 in 70% yield.

To a solution of 3 (610 mg, 3.3 mmol) in dry DCM (20 mL) was added triethylamine (550 μL, 3.9 mmol) and benzyl chloroformate (550 μL, 3.9 mmol). The reaction was stirred at room temperature for 2 hours. The solution was concentrated and purified by $SiO_2$ chromatography over a gradient of 0-30% EtOAc in Hexanes to give 4 in 66% yield.

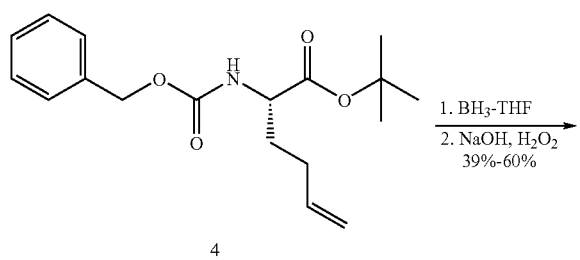

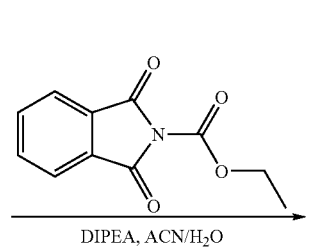

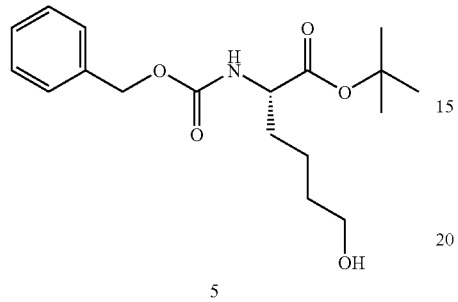

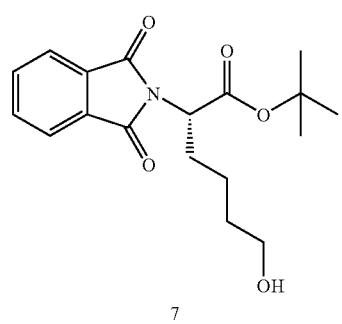

To a stirred solution of 4 (577 mg, 1.8 mmol) in THF (20 mL) under N$_2$ was added BH$_3$.THF. After 1 hour 3 N NaOH (300 μL, 0.9 mmol) and H$_2$O$_2$ (306 μL, 2.7 mmol) was added. The reaction was stirred overnight and subsequently diluted with H$_2$O, extracted 2× with ethyl ether, dried with MgSO$_4$ and concentrated. The product was purified by SiO$_2$ chromatography over a gradient of 10-45% EtOAc in Hexanes to give 5 in 50% yield.

To 6 (42 mg, 0.21 mmol) in ACN (2 mL) carbethoxyphthalimide (50 mg, 0.23 mmol) was added with DIPEA (40 μL, 0.23 mmol) and stirred at room temperature for 2 hours. H$_2$O (1 mL) was added and stirred for an additional 10 minutes. The ACN was evaporated off and DCM and 10% citric acid were added. The aqueous layer was separated and extracted 3× with DCM, the DCM portions were combined, dried with Na$_2$SO$_4$, and concentrated to give 7 in 95% yield.

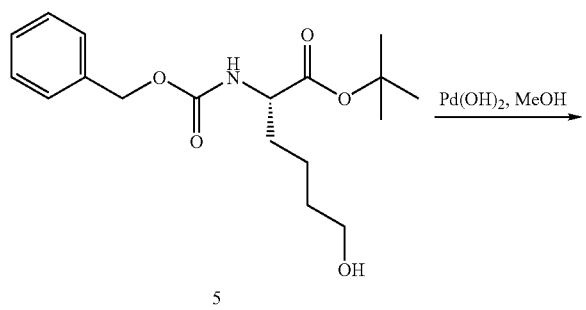

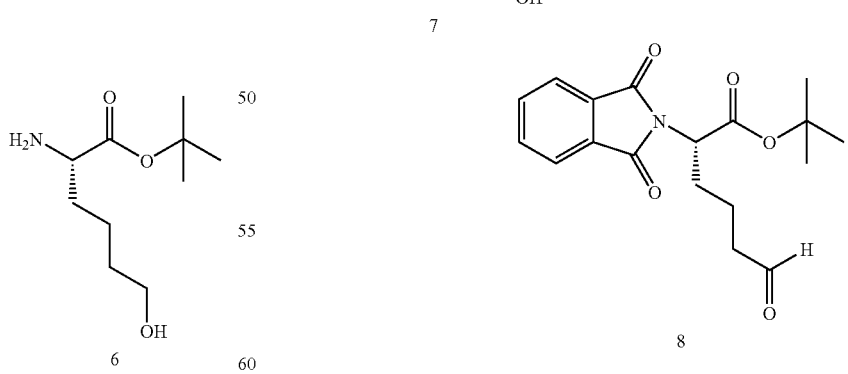

To a stirred solution of 5 (71 mg, 0.21 mmol) in MeOH (2 mL) under 1 atm H$_2$ 10% palladium hydroxide on carbon (30 mg) was added. The reaction was complete after 30 minutes. The reaction was filtered over Celite and concentrated to give 6 in quantitative yield.

Oxalyl chloride (561 μL, 6.60 mmol) was dissolved in DCM (35 mL), cooled to −78° C., stirred for 5 minutes followed by addition of a solution of dimethylsulfoxide (870 μL, 12.3 mmol) in DCM (2.5 mL). After stirring for 5 minutes 7 (1.05 g, 3.15 mmol) in dichloromethane (20 mL) was added followed by triethylamine (2.37 mL, 17.0 mmol). The reaction was slowly warmed to room temperature. DCM and H₂O were added, the aqueous layer separated and extracted 2× with DCM. The DCM portions were combined, filtered through Na₂SO₄, and concentrated to give 8 in 95% yield.

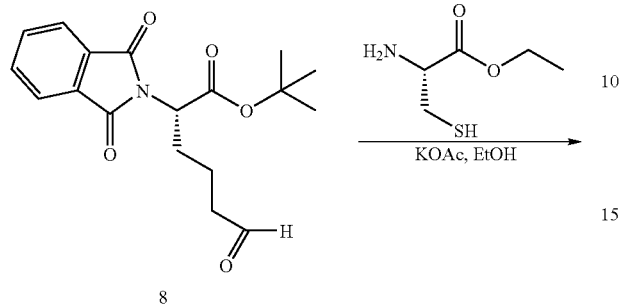

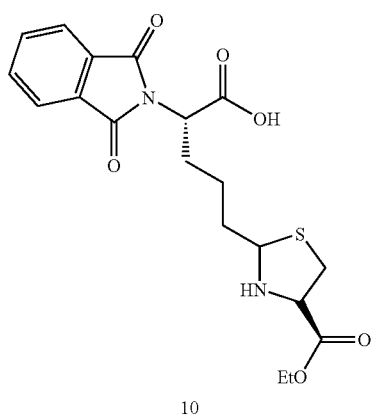

The diastereomers were redissolved in 1:1 TFA:DCM (10 mL) and stirred for 1 hour at room temperature. LCMS showed complete conversion to 10. The reaction was concentrated to give 10 in 95% yield for the two diastereomers.

L-cysteine ethyl ester hydrochloride (643 mg, 3.5 mmol) and potassium acetate (343 mg, 3.5 mmol) were dissolved in stirring EtOH (13 mL), and cooled to 0° C. in an ice water bath. Compound 8 was dissolved in EtOH (13 mL) and added. The reaction was stirred at 0° C. for 4 hours, LCMS confirmed the conversion of 8 into two diastereomeric products. The reaction was filtered, EtOH evaporated, redissolved in DCM and washed with brine, dried with MgSO₄ and concentrated to give a 1:1 mixture of diastereomers 9 in quantitative yield.

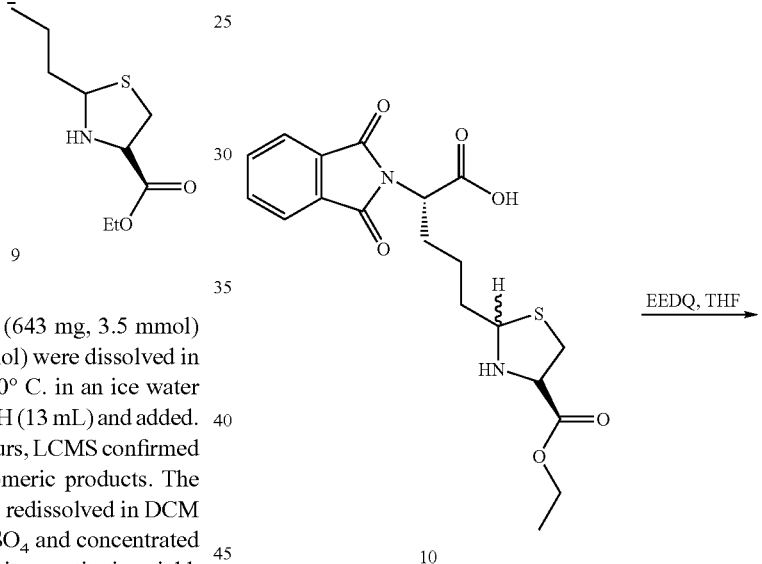

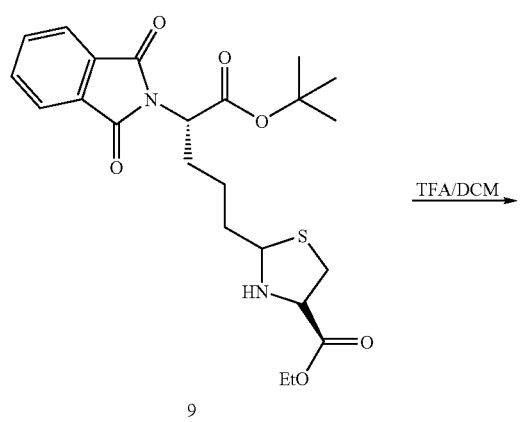

To a stirred solution of 10 (675 mg, 1.67 mmol) in THF (20 mL), EEDQ (619 mg, 2.50 mmol) was added. Stirred at room temperature for 2 days. The THF was removed under reduced pressure, the product redissoved in EtOAc. The organic layer was washed with 0.5 N HCl, 0.5% NaHCO₃, H₂O, brine. The EtOAc solution was dried with MgSO₄ and concentrated. The product was purified via reverse phase HPLC 10-70% ACN in H₂O to give two diastereomers 11, 20% yield for diastereomer 1 and 18% yield for diastereomer 2.

Example 2

1-[2-Cyclohexyl-2-(2-methylamino-propionylamino)-acetyl]-pyrrolidine-2-carboxylic acid (2-phenyl-2H-pyrazol-3-yl)-amide

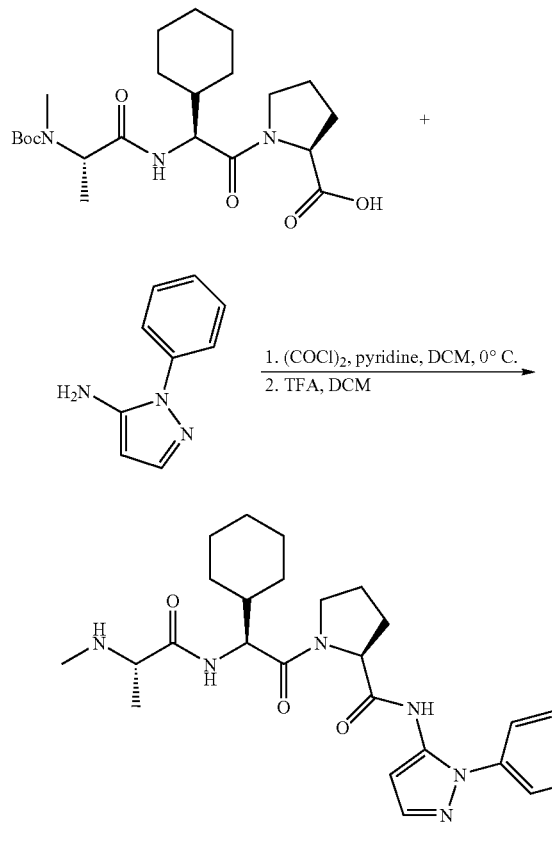

A solution of Boc-MeAla-Chg-Pro-OH (47.0 mg, 0.107 mmol) and pyridine (26 µl, 0.32 mmol) in anhydrous dichloromethane (300 µl) was cooled to 0° C. and a solution of oxalyl chloride in dichloromethane (54 µl, 2.0 M, 0.11 mmol) was added dropwise over 10 minutes. The mixture was stirred at 0° C. for 15 minutes, then at ambient temperature for 45 minutes, and a solution of 5-amino-1-phenylpyrazole (15.9 mg, 0.100 mmol; TCI America catalog #A0174) and pyridine (15.5 µl, 0.191 mmol) in dichloromethane (0.5 ml) was added. The resulting mixture was stirred at ambient temperature for 16 hours, diluted with dichloromethane to 20 ml, and washed with 0.2 N aqueous sodium hydroxide (20 ml). The organic phase was dried (MgSO₄) and concentrated under reduced pressure. The crude product was purified by column chromatography (silica gel, 60% ethyl acetate in hexanes, then 100% ethyl acetate) to yield a yellow oil: m/z 581 (MAO The oil was treated with 5% trifluoroacetic acid in dichloromethane (2 ml), and after 18 hours the solvent was removed in vacuo. The resulting oil (29.3 mg, 57% yield over 2 steps) was further purified by reversed-phase HPLC to yield the product (TFA salt, 9.6 mg, 15% yield): m/z 481 (M+H⁺), 503 (M+Na⁺).

Example 3

4-Phenyl-[1,2,3]thiadiazol-5-ylamine

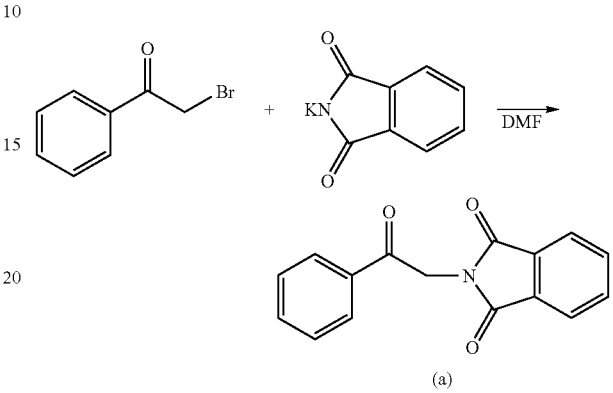

2-bromoacetophenone was dissolved in DMF (3 vol) and potassium phthalimide (1.1 eq.) was added. The reaction, initially mildly exothermic, was stirred overnight at room temperature.

The DMF was removed in vacuo and the reaction was diluted with DCM (~3 vol) followed by 0.1N NaOH (~3 vol; 1:1 aq/org) and stirred vigorously then extracted. The organic layer, containing some solid material, was concentrated in vacuo and the resulting solid was slurried in diethyl ether and collected by suction filtration to give (a) as a white crystalline solid in ~95% yield.

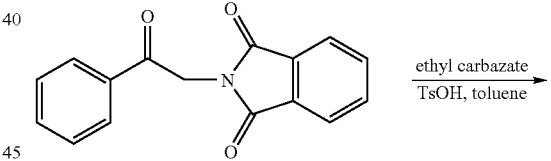

(a)

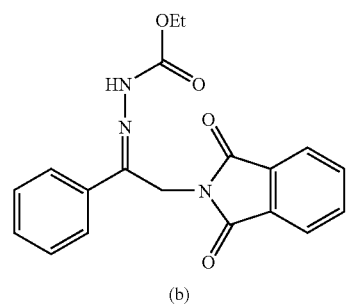

(b)

Compound (a), ethyl carbazate (1.5 eq) and TsOH—H₂O (0.1 eq) were combined in toluene (5 vol) and heated to reflux using a Dean-Stark trap to remove water. The solution turned a dark red color and was complete by TLC in ~2 hrs. Approximately half of the toluene was removed by distillation, the solution was cooled to r.t. and concentrated in vacuo. The resulting solid was slurried in EtOH (the minimum volume necessary for stirring), heated to reflux for 30 min and then cooled on ice to facilitate precipitation of both isomers. The solid was collected by suction filtration, washed with cold EtOH and dried under vacuum to give both isomers of compound (b) as an off-white solid in ~90% yield.

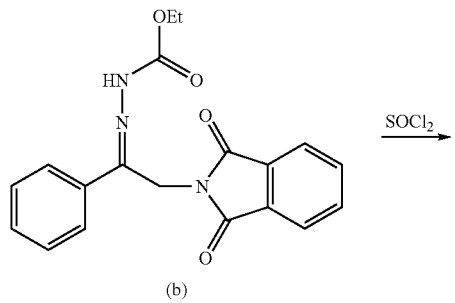

(b)

To ice-cooled thionyl chloride (4 eq, ~0.85 vol) was added, portion-wise (in order to control the exotherm), the isomer mixture of (b). The ice bath was removed and the reaction warmed to r.t and stirred overnight. Thionyl chloride was removed in vacuo, DCM (1 vol) was added and the reaction was stirred with 0.1M NaOH (1 vol; 1:1 aq/org). The suspension was extracted and the organics were concentrated in vacuo, slurried in refluxing EtOAc (the minimum volume necessary for easy stirring) for 30 min, cooled to r.t., collected by suction filtration and washed with a minimum of cold EtOAc to give (c) as an off-white crystalline solid in ~80% yield.

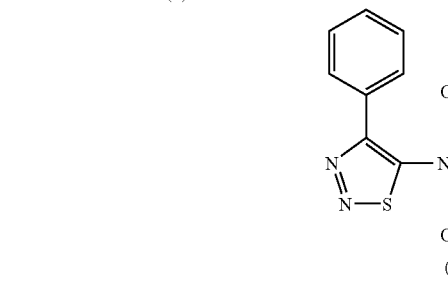

(c)

A solution of hydrazine hydrate (2.4 eq) in EtOH (1 vol) was added dropwise to a refluxing solution of (c) in EtOH (8 vol). A precipitate formed almost immediately and the reaction was completed by TLC in ~3 hrs. The solution was cooled to r.t. and the phthalimide cleavage by-product was filtered away and washed with DCM. The EtOH/DCM filtrate was concentrated in vacuo until crystal formation was observed. This suspension was stirred overnight and the crystalline/solid mixture was collected by suction filtration and washed with cold EtOH until colored impurities were removed, giving the thiadiazole amine (d) in ~75% yield as an off-white crystalline solid.

Example 4

1-[2-Cyclohexyl-2-(2-methylamino-propionylamino)-acetyl]-pyrrolidine-2-carboxylic acid (4-phenyl-[1,2,3]thiadiazol-5-yl)-amide

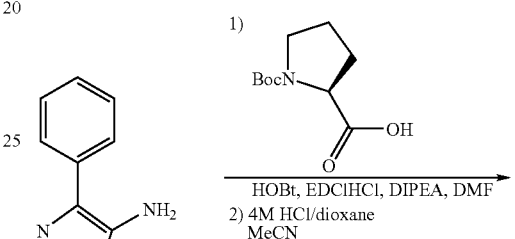

(d)

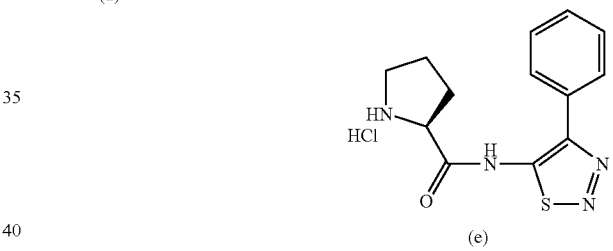

(e)

Boc-L-Pro (2 eq), HOBt (1.9 eq), EDC-HCl (1.9 eq) and DIPEA (5 eq) were dissolved in DMF (10-15 vol). To this was then added the thiadiazole amine (d). The reaction, initially mildly exothermic, was heated to 75° C. and stirred overnight, cooled to room temperature and the DMF was partially removed in vacuo. Dilution with EtOAc (10-15 vol) was followed by washing with 1M HCl (2×), NaHCO₃ (1×), and brine (1×) (1:1 aq/org). The organic layer was concentrated in vacuo and the resulting solid was slurried in refluxing MeCN (a minimum volume necessary for easy stirring) for 30 min and then cooled to r.t. Suction filtration gave Boc-protected conjugation product as an off-white crystalline solid in ~77% yield. The Boc-protected product was suspended in a solution of 4M HCl/dioxane (4-5 eq acid) and MeCN (1 vol eq to the dioxane solution) and stirred at r.t. until LCMS indicated complete deprotection, ~1 hr. The reaction mixture was concentrated in vacuo and the resulting solid was vigorously slurried in refluxing MeCN (a minimum volume necessary for easy stirring), cooled to r.t., and the solid collected by suction filtration and washed with cold MeCN until residual color was removed from the cake to yield the HCl salt (e) as an off-white solid in approximately quantitative yield.

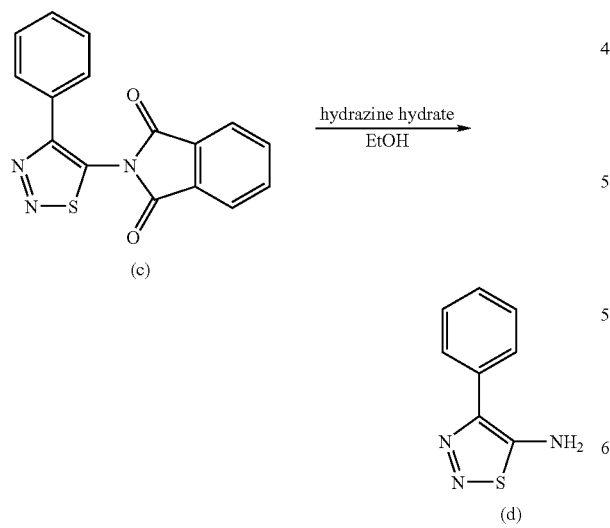

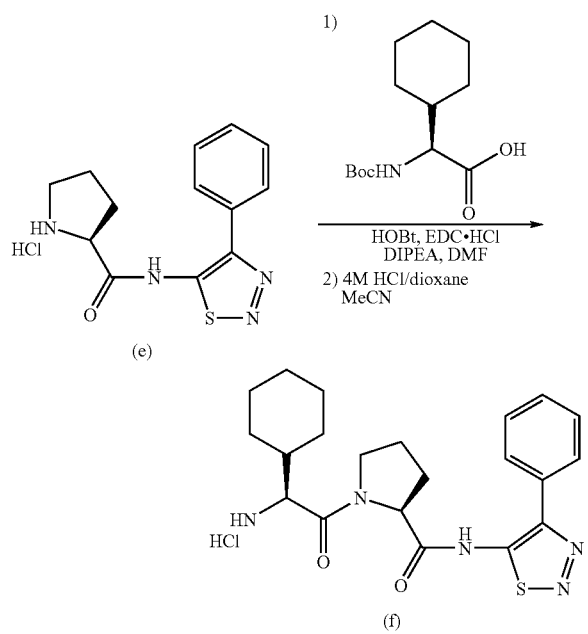

The HCl salt (e) was dissolved in DMF (10-15 vol) and DIPEA (5 eq). To this was added the Boc-L-Chg (1.5 eq), HOBt (1.4 eq) and EDC-HCl (1.4 eq). Coupling was complete after ~2 hrs by LCMS. The reaction was diluted with EtOAc (15 vol) and washed with 1M HCl (2×), NaHCO$_3$ (1×), and brine (1×) (1:1 aq/org). The organic extract was dried over sodium sulfate and concentrated in vacuo. The resulting solid is slurried in EtOH/Hexane (20:80) (a minimum volume necessary for easy stirring) and filtered to give Boc-protected conjugate product as a fluffy white solid in ~80% yield. The Boc-protected was dissolved in a solution of 4M HCl/dioxane (4-5 eq acid) and MeCN (0.25 volume eq to the dioxane solution) and stirred at r.t. until LCMS indicated complete deprotection, ~1 hr. The reaction was concentrated to dryness with toluene (2×) (the same volume as the deprotection solution) to yield the HCl salt (f) as a white crystalline solid in approximately quantitative yield.

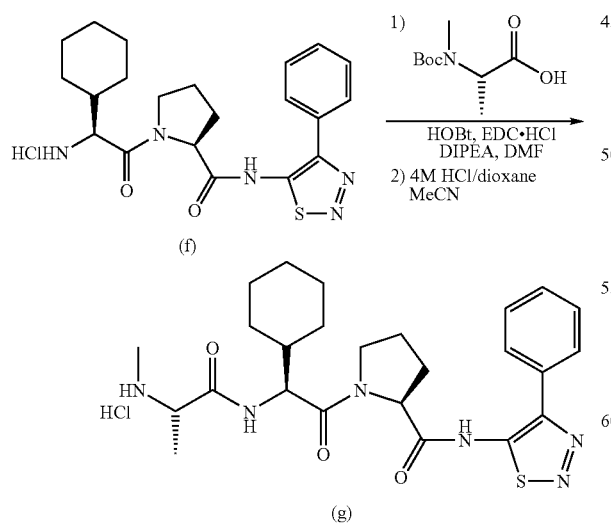

The HCl salt (f) was dissolved in DMF (10-15 vol) and DIPEA (5 eq). To this was added the Boc-L-N-methyl Ala (1.5 eq), HOBt (1.4 eq), and EDC-HCl (1.4 eq). Coupling was complete after ~1 hr by LCMS. The reaction was diluted with EtOAc (15 vol) and washed with 1M HCl (2×), NaHCO$_3$ (1×), and brine (1×) (1:1 aq/org). The organic extract was dried over sodium sulfate and concentrated in vacuo to give the Boc-protected conjugate product as a beige, foamy solid in ~85% yield. The Boc-protected conjugate was dissolved in a solution of 4M HCl/dioxane (4-5 eq acid) and MeCN (0.25 volume eq to the dioxane solution) and stirred at r.t. until LCMS indicated complete deprotection, ~1 hr. The reaction was concentrated to dryness with toluene (2×) (same volume as deprotection solution) and the resulting solid was slurried in a solution of MTBE/EtOAc (70:30) (minimal volume necessary for easy stirring), filtered and collected to yield crude (g) as an off-white free-flowing solid. The crude HCl salt (g) was suspended in MeOH (4 vol minimum) and dissolved with stirring at 65° C. Warm Isopropyl Acetate (6-8 vol) is added in two portions, keeping the temperature at approx. 60° C., and the solution was allowed to cool with stirring. Crystallization took place rapidly, the suspension was stirred at room temperature for several hours, then stirred at 0° C. for an hour before the solid was collected by suction filtration, washed with MeOH/iPrOAc (1:4, 2 vol) and dried to yield final the product as a white/off-white crystalline solid in ~80% yield from (f).

Example 5

2-[tert-butoxycarbonyl-(1H-pyrrol-2-ylmethyl)-amino]-propionic Acid

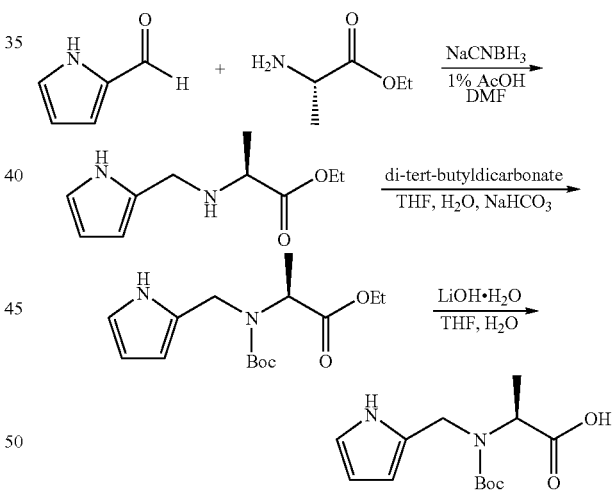

Alanine ethyl ester (5 g, 32.5 mmol), pyrrole-2-carboxaldehyde (3.1 g, 32.5 mmol), sodium cyanoborohydride (2.04 g, 32.5 mmol) and AcOH (1%) were mixed in DMF and stirred overnight. The reaction was quenched with H$_2$O, and DMF was evaporated. The mixture was diluted with EtOAc, washed by 0.1N NaOH, dried and concentrated to yield product 2.5 g. The resulting ester (2.5 g, 12.8 mmol), di-tert-butyldicarbonate (3.06 g, 14 mmol) were mixed in THF, H$_2$O with NaHCO$_3$ and stirred overnight. THF was evaporated, and the mixture was diluted with EtOAc, washed by 1N NaOH, sat. NH$_4$Cl and brine. After dried, the mixture was concentrated to yield the Boc-protected ester 3.3 g. The Boc-protected ester (1.67 g, 5.6 mol), lithium hydroxide mono hydrate (284 mg, 6.77 mmol) were mixed in THF and H$_2$O at 0° C. THF was vacuumed off, and the solution was acidified by dilute H₂SO₄, extracted by EtOAc twice. Organic layers were combined, dried and evaporated.

Example 6

Tetrahydropyranylglycine

Tetrahydropyranylglycine was purchased from NovaBiochem, or synthesized according to the literature: Ghosh, A. K.; Thompson, W. J.; holloway, M. K.; McKee, S. P.; Duong, T. T.; Lee, H. Y.; Munson, P. M.; Smith, A. M.; Wai, J. M; Darke, P. L.; Zugay, J. A.; Emini, E. A.; Schleife, W. A.; Huff, J. R.; Anderson, P. S. *J. Med. Chem.*, 1993, 36, 2300-2310.

Example 7

Piperidinylglycine

Piperidinylglycine was synthesized according to the literature: Shieh, W-C.; Xue, S.; Reel, N.; Wu, R.; Fitt, J.; Repic, O. *Tetrahedron: Asymmetry*, 2001, 12, 2421-2425.

Example 8

4,4-difluorocyclohexylglycine 4,4-difluorocyclohexylglycine was made according to the procedures described in US 2003/0216325.

Example 9

Boc (S)-2-amino-2-(4-hydroxycyclohexyl)acetic Acid

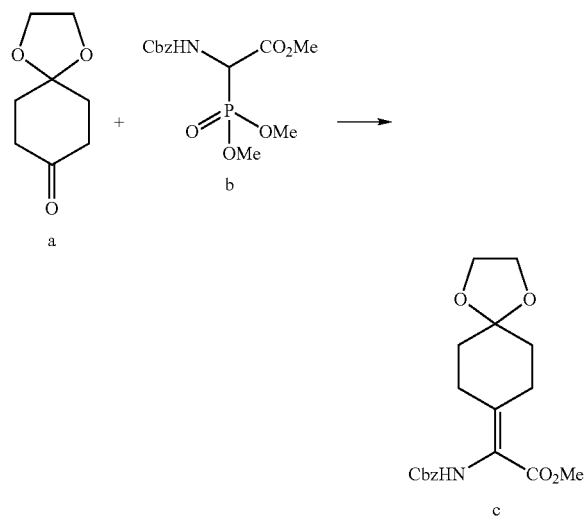

Following the procedure of Sheih, (*Tetrahedron: Asymmetry*, 2001, 12, 2421-2425), a solution of ketone a (8.4 g) and EtOAc (30 mL) was added to a solution of N-Cbz-phosphonoglycine methyl ester b, TMG (4.5 mL) and EtOAc (30 mL). The solution was maintained at rt for 48 h, then washed with 1N HCl (3×50 mL), brine (1×50 mL) dried (Na₂SO₄), filtered, and concentrated. The residue was adsorbed onto Celite, and purified by chromatography, then further purified by re-crystallization from EtOAc/hexanes to afford 5.2 g of product c.

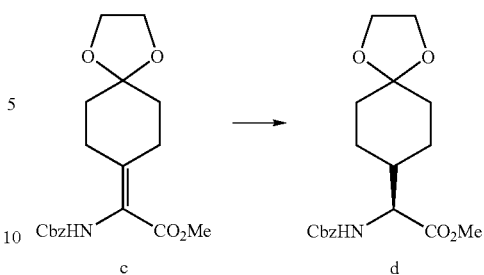

Following the procedure of Sheih, (*Tetrahedron: Asymmetry*, 2001, 12, 2421-2425), a solution of eneamide c (5.0 g), (S,S)-Me-BPE-Rh(I) (1.5 g, Strem Chemicals, Newburyport, Mass.), and MeOH (100 mL) was shaken virgorously under 70 psi of H₂ for 48 h. The solvent was removed under reduced pressure. The residue was taken up in EtOAc, and filtered through SiO₂ with more EtOAc. The solvent was removed under reduced pressure to afford 4.0 g of product d as a colorless solid.

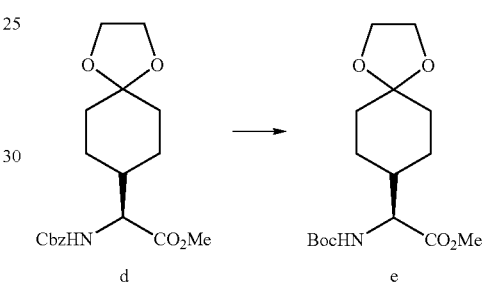

A mixture of Cbz-carbamate d, (4.0 g) Boc₂O, (2.9 g), 20% Pd(OH)₂.C (1.0 g) and MeOH (30 mL) was maintained under an atmosphear of H₂ for 6 h. The mixture was filtered through Celite with MeOH. The solvent was removed under reduced pressure to afford 4.5 g of residue e, which was taken on directly.

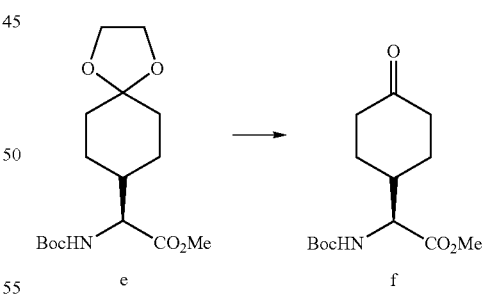

The residue e from above was dissolved in H₂O (10 mL), AcOH (30 mL), THF (5 mL), and dichloroacetic acid (3 mL) and maintained at rt overnight. Water (5 mL) was added and the solution and maintained until hydrolysis was complete, as monitored by HPLC-MS. Solid Na₂CO₃ was added cautiously until gas evolution ceased, the mixture was diluted with aq NaHCO₃, and extracted with 10% EtOAc/DCM. The combined organic phases were washed once with brine, dried (Na₂SO₄), filtered, and concentrated. The residue was purified by chromatography to afford 2.9 g of product 1.

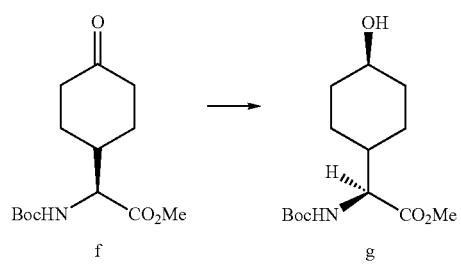

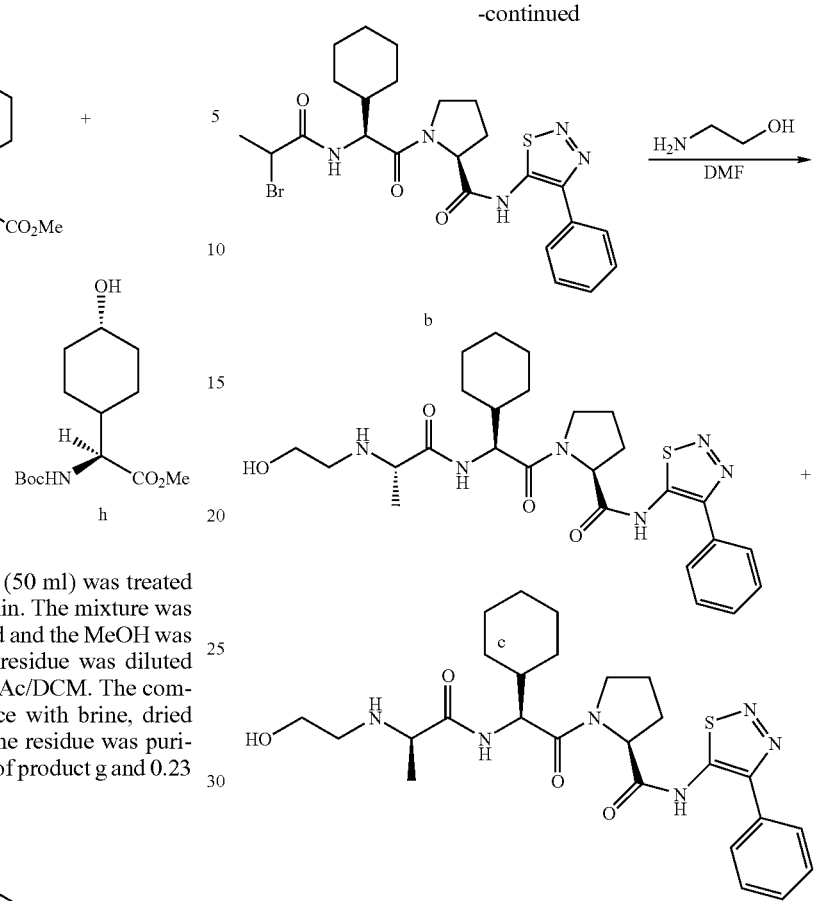

A mixture of ketone f (1.5 g) MeOH (50 ml) was treated with NaBH4 (290 mg) at 0° C. for 20 min. The mixture was acidified to ~pH1 with 10% aq citric acid and the MeOH was removed under reduced pressure. The residue was diluted with water and extracted with 20% EtOAc/DCM. The combined organic phases were washed once with brine, dried (Na$_2$SO$_4$), filtered, and concentrated. The residue was purified by chromatography to afford 1.17 g of product g and 0.23 g of product h.

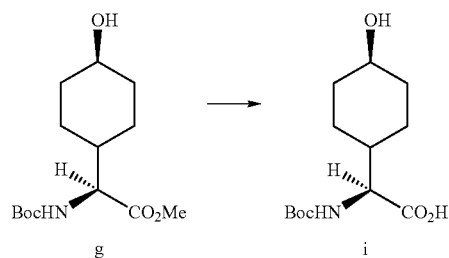

A mixture of ester g (1.17 g) LiOH.H2O (160 mg), THF (3 mL) and water (4.5 mL) was stirred vigorously at rt overnight. The mixture was diluted with brine and exhaustively extracted with EtOAc. The combined organic phases were washed once with brine, dried (Na$_2$SO$_4$), filtered, and concentrated to afford acid i (525 mg).

Example 10

Compound 29

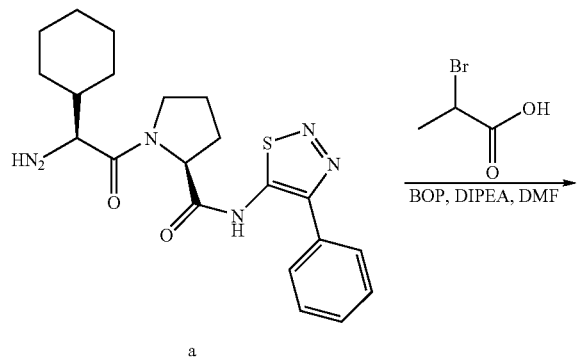

A mixture of amine a (1.56 mmol), 2-Bromopropionic acid (0.72 g, 4.68 mmol), BOP (2.1 g, 4.68 mmol) and DIPEA (1.6 ml, 9.36 mmol) in 10 ml DMF was stirred at room temperature for 2 hours. LCMS analysis indicated reaction completed. 100 ml EtOAc was added to the reaction and organic layer was washed with sat. NaHCO$_3$ followed by brine, dried over Na$_2$SO$_4$ and concentrated to dryness. The crude material was purified by chromatography using 50% EtOAc/hexane to obtain compound b.

The compound b (0.832 g, 1.5 mmol) was treated with ethanolamine (200 ul, 2.73 mmol) in 3 ml DMF and stirred overnight for completion. The reaction mixture was purified by reverse phase HPLC to obtain two diastereomers c (53 mg) and d (compound 29) (150 mg).

Example 11

N-Boc-N-cyclopropylmethyl-L-alanine

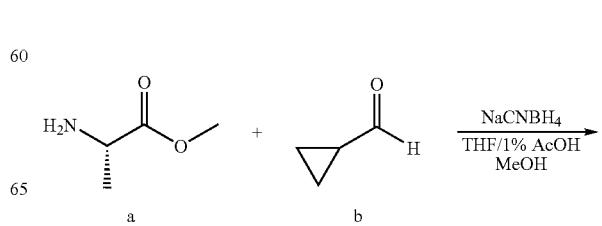

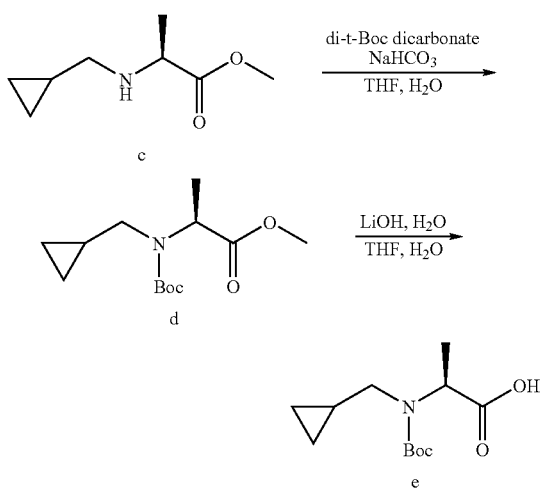

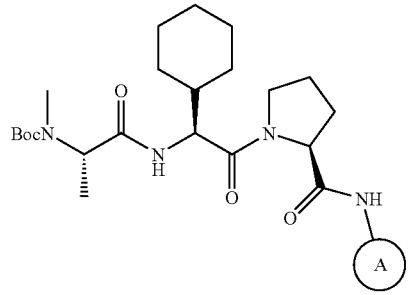

A solution of Boc-MeAla-Chg-Pro-OH (2.3 mmol) and pyridine (6.9 umol) in anhydrous dichloromethane (23 ml) was cooled to 0° C. and cyanuric fluoride (2.3 mmol) added dropwise over 30 sec. The mixture was stirred at 0° C. for 15 min, at ambient temperature for 5 hr, and then quenched with water. The mixture was extracted three times with dichloromethane (total 100 ml), and the combined organic phases washed with brine and dried over anhydrous sodium sulfate. Filtration and concentration in vacuo yielded the peptide acid fluoride as a clear, colorless oil used directly without further purification.

A solution of the crude acid fluoride (0.50 mmol) and pyridine (1.5 mmol) in dichloromethane (2.5 ml) was added to the solid amine (0.50 mmol), and the resulting mixture stirred either at ambient temperature or at 50° C. (sealed vessel). The mixture was poured into aqueous sodium bicarbonate and the extracted three times with dichloromethane (total 100 ml). The combined organic phases were washed with brine, dried over anhydrous sodium sulfate, filtered and concentrated in vacuo. The crude peptide amide was used directly without further purification.

L-alanine methyl ester hydrochloride a (5 g, 35.8 mmol) and cyclopropanecarboxaldehyde b (2.67 ml, 35.8 mmol) were suspended in 50 ml THF w/1% AcOH. Addition of 5 ml of CH$_3$OH made the cloudy solution turned to clear. NaCNBH$_4$ (2.25 g, 35.8 mmol) was added and the reaction mixture stirred overnight. The reaction was quenched by addition of 1N aq. NaOH, extracted by EtOAc twice, organic layers were dried over Na$_2$SO$_4$ and concentrated to dryness. The crude material was purified by chromatography using 30% EtOAc/hexane (stained by ninhydrin) to obtain the compound c (1 g, 18%). The compound c (1 g, 6.37 mmol) and di-t-bocdicarbonate (2.1 g, 9.55 mmol) were diluted in THF (20 ml) and H$_2$O (20 ml), NaHCO$_3$ (1.3 g, 15.9 mmol) was added. The reaction mixture stirred overnight for completion. THF was removed under reduced pressure, and the aqueous layer was extracted by EtOAc 3 times. Combined organic layers were washed by 1N NaOH, sat, NH$_4$Cl followed by brine, the concentrated to dryness. The Boc-protected compound d (1.39 g, 5.40 mmol) was stirred with LiOH.H$_2$O (1.14 g, 27 mmol) in THF (20 ml) and H$_2$O (20 ml) overnight at room temperature. THF was stripped off, and the aqueous layer was adjusted to pH=4 by adding 10% citric acid, then extracted by EtOAc 3 times. Combined organic layers were washed by brine and concentrated. The crude was purified by reverse phase C-18 column eluted by 0%-50% acetonitrile/H$_2$O to give pure compound e as a white solid (794 mg).

Example 12

Acid Fluoride Coupling Procedure

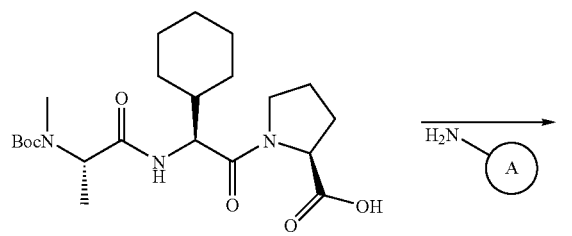

Example 13

1-phenyl-1H-pyrazol-5-amine

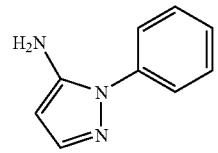

1-phenyl-1H-pyrazol-5-amine is commercially available from TCI America (catalog #A0174).

Example 14

3-methyl-1-phenyl-1H-pyrazol-5-amine

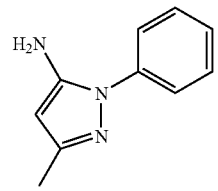

3-methyl-1-phenyl-1H-pyrazol-5-amine is commercially available from TCI America (catalog #A1311).

Example 15

5-phenylthiazole-2,4-diamine

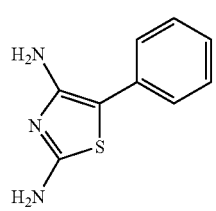

5-phenylthiazole-2,4-diamine is commercially available from Acros Organics (catalog #11234-0010).

Example 16

5-(trifluoromethyl)-4-phenylthiophen-3-amine

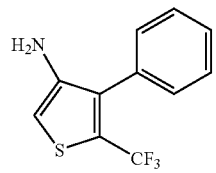

5-(trifluoromethyl)-4-phenylthiophen-3-amine is commercially available from Acros Organics (catalog #SEW03133DA).

Example 17

4-phenyl-1H-pyrazol-3-amine

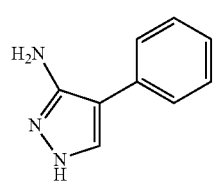

4-phenyl-1H-pyrazol-3-amine was prepared according to the procedures described in E. L. Anderson et al.; *J. Med. Chem.*, 1964, 7, 259-268.

Example 18

5-methyl-4-phenyl-1H-pyrazol-3-amine

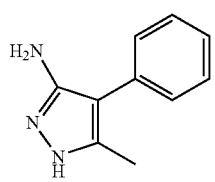

5-methyl-4-phenyl-1H-pyrazol-3-amine was prepared according to the procedures described in E. L. Anderson et al.; *J. Med. Chem.*, 1964, 7, 259-268.

Example 19

3-phenyl-3H-1,2,3-triazol-4-amine

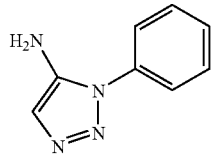

3-phenyl-3H-1,2,3-triazol-4-amine was prepared according to the procedures described in K. M. Baines, T. W. Rourke, K. Vaughan; *J. Org. Chem.*, 1981, 46, 856-859.

Example 20

4-phenylisoxazol-5-amine

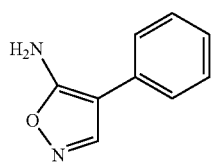

4-phenylisoxazol-5-amine was prepared according to the procedures described in H. Peeters, W. Vogt; EP 43024.

Example 21

3-phenyl-1H-pyrazol-4-mine

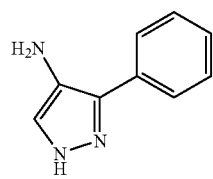

3-phenyl-1H-pyrazol-4-amine was prepared according to the procedures described in C. Chen, K. Wilcoxen, J. R. McCarthy; *Tetrahedron Lett.,* 1988, 39, 8229-8232.

Example 22

1-methyl-3-phenyl-1H-pyrazol-4-amine

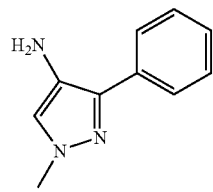

1-methyl-3-phenyl-1H-pyrazol-4-amine was prepared according to the procedures described in C. Chen, K. Wilcoxen, J. R. McCarthy; *Tetrahedron Lett.,* 1988, 39, 8229-8232.

Example 23

1-methyl-5-phenyl-1H-pyrazol-4-amine

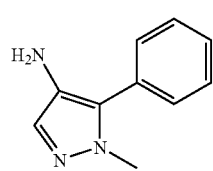

1-methyl-5-phenyl-1H-pyrazol-4-amine was prepared according to the procedures described in C. Chen, K. Wilcoxen, J. R. McCarthy; *Tetrahedron Lett.,* 1988, 39, 8229-8232.

Example 24

3-methyl-4-phenylisoxazol-5-amine

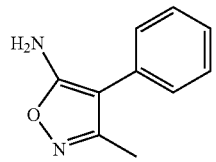

3-methyl-4-phenylisoxazol-5-amine was prepared according to the procedures described in H. Peeters, W. Vogt; EP 43024.

Example 25

1-phenyl-1H-tetrazol-5-amine

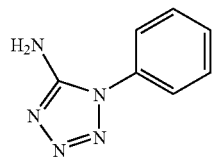

1-phenyl-1H-tetrazol-5-amine was prepared according to the procedures described in R. A. Batey, D. A. Powell; *Org. Lett.,* 2000, 2, 3237-3240.

Example 26

4-phenyl-1,2,5-oxadiazol-3-amine

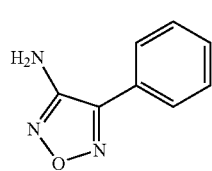

4-phenyl-1,2,5-oxadiazol-3-amine was prepared according to the procedures described in R. Lakhan, O. P. Singh; *Ind. J. Chem.*, 1987, 26B, 690-692.

Example 27

1-amino-5-phenyl-1H-tetrazole

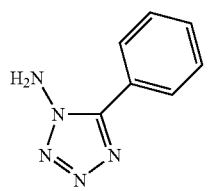

1-amino-5-phenyl-1H-tetrazole was prepared according to the procedures described in T. L. Gilchrist, G. E. Gymer, C. W. Rees; *J. Chem. Soc., Perkin Trans.* 1, 1975, 1747-1750.

Example 28

4-amino-3-phenyl-4H-1,2,4-triazole

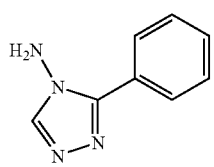

4-amino-3-phenyl-4H-1,2,4-triazole was prepared according to the procedures described in A. A. Ikizler, N. Yildirim; *J. Heterocyclic Chem.*, 1998, 35, 377-380.

Example 29

3-phenylthiophen-2-amine

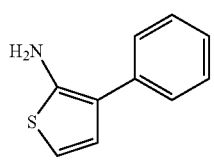

3-phenylthiophen-2-amine was prepared according to the procedures described in Y. Yoshikawa et al.; EP 737682 (U.S. Pat. No. 5,747,518).

Example 30

2-phenylthiophen-3-amine

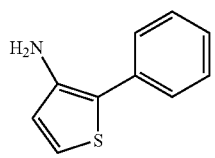

2-phenylthiophen-3-amine was prepared according to the procedures described in Y. Yoshikawa et al.; EP 737682 (U.S. Pat. No. 5,747,518).

Example 31

4-phenylthiophen-3-amine

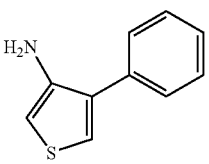

4-phenylthiophen-3-amine was prepared according to the procedures described in G. Kirsch, D. Cagniant, P. Cagniant; *J. Heterocyclic Chem.*, 1982, 19, 443-445.

Example 32

5-amino-4-phenylthiazole-2-thiol

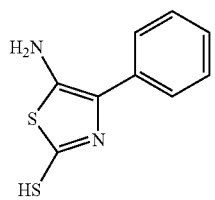

5-amino-4-phenylthiazole-2-thiol was prepared according to the procedures described in A. H. Cook, I. Heilbron, A. L. Levy; *J. Chem. Soc.*, 1947, 1598-1609.

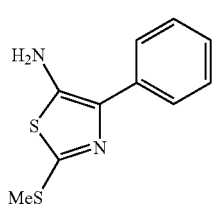

Example 33

2-(methylthio)-4-phenylthiazol-5-amine 2-(methylthio)-4-phenylthiazol-5-amine was prepared according to the procedures described in A. H. Cook, I. Heilbron, A. L. Levy; J. Chem. Soc., 1947, 1598-1609.

Example 34

5-amino-2-(methylsulfinyl)-4-phenylthiazole

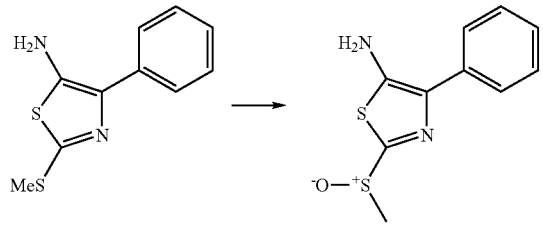

To 5-amino-2-(methylsulfanyl)-4-phenylthiazole (305 mg, 1.37 mmol) in acetic acid (3.0 ml) was added aqueous hydrogen peroxide (660 µl, 30% wt, 6.9 mmol) dropwise at ambient temperature. After 4 hr the mixture was partitioned between dichloromethane (60 ml) and water (60 ml). The organic phase was separated, washed with brine, dried over sodium sulfate, filtered and concentrated in vacuo. Flash chromatography on silica gel (ethyl acetate/hexanes) yielded pure 5-amino-2-(methylsulfinyl)-4-phenylthiazole (285 mg, 87%).

Example 35

5-amino-2-(methylsulfonyl)-4-phenylthiazole

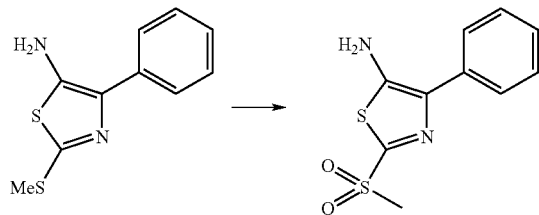

To 5-amino-2-(methylsulfanyl)-4-phenylthiazole (302 mg, 1.36 mmol) in dichloromethane (5.0 ml) was added portionwise 3-chloroperbenzoic acid (638 mg, 77% wt, 2.9 mmol) with cooling to 0° C. The mixture was diluted with dichloromethane (3.0 ml) and after 5 min allowed to warm to ambient temperature. After 3 hr a further quantity of 3-chloroperbenzoic acid (305 mg, 77% wt, 1.4 mmol) was added portionwise. After 20 hr the mixture was treated with sodium thiosulfate (2 ml, 1.0 M), poured into saturated aqueous sodium bicarbonate and extracted three times into dichloromethane (total 100 ml). The combined organic phases were washed with saturated aqueous sodium bicarbonate and brine, dried over sodium sulfate and concentrated in vacuo to give a dark brown foam. Flash chromatography on silica gel (ethyl acetate/hexanes) yielded pure 5-amino-2-(methylsulfonyl)-4-phenylthiazole (90 mg, 26%).

Example 36

5-amino-2-(aminosulfonyl)-4-phenylthiazole and 5-amino-4-phenylthiazole

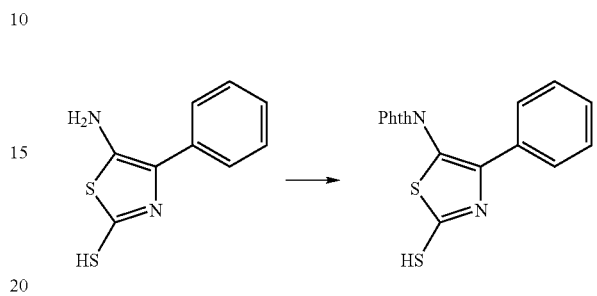

5-Amino-2-mercapto-4-phenylthiazole (1.01 g, 4.83 mmol) and phthalic anhydride (716 mg, 4.84 mmol) in acetic acid (20 ml) were heated at 100° C. for 64 hr and allowed to cool. The mixture was diluted into cold water (150 ml) and the precipitate collected by filtration, washed with water (50 ml) and dried under high vacuum (1.46 g, 90%). The phthalimide is contaminated with a minor quantity of disulfide but used without further purification.

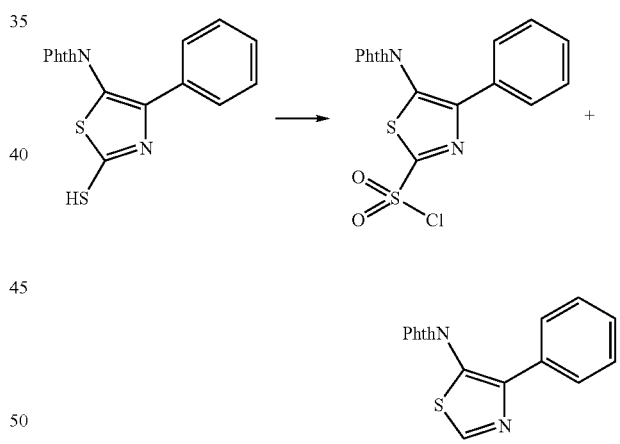

2-Mercapto-4-phenyl-5-phthalimido-thiazole (203 mg, 600 µmol) in acetic acid (4.5 ml) and water (0.5 ml) at 0° C. was treated with N-chlorosuccinimide (243 mg, 1.82 mmol) in one portion. The mixture was stirred at 0° C. for 10 min, allowed to warm to ambient temperature for 1 hr and then partitioned between dichloromethane (50 ml) and water (50 ml). The aqueous phase was extracted twice more with dichloromethane (2×25 ml), and the combined organic phases washed with brine and dried over sodium sulfate. Filtration and concentration in vacuo yielded a mixture (231 mg) of 2-(chlorosulfonyl)-4-phenyl-5-phthalimido-thiazole (major component) with 4-phenyl-5-phthalimido-thiazole (ca. 2:1), used without purification.

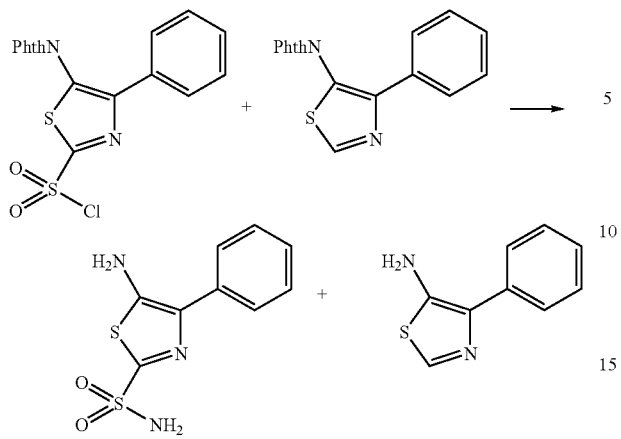

The crude mixture of sulfonyl chloride with 4-phenyl-5-phthalimido-thiazole (231 mg) in dichloromethane (10 ml) was treated with ammonia in methanol (900 μl, 2.0 M) dropwise at ambient temperature. After 10 min the mixture was concentrated in vacuo. The residue was suspended in ethanol (10 ml), treated with ethanolic hydrazine (660 μl, 1.0 M, 660 μmol) and heated to reflux. After 1.5 hr a further portion of ethanolic hydrazine was added (660 μl, 1.0 M, 660 mol) and reflux continued for 15 hr. The cooled mixture was filtered and concentrated in vacuo. Flash chromatography on silica gel (ethyl acetate/hexanes) yielded pure 5-amino-2-(aminosulfonyl)-4-phenylthiazole (56 mg, 36% for 3 steps) and 5-amino-4-phenylthiazole (17 mg, 16% for 3 steps).

Example 37

5-amino-2-(tent-butylsulfanyl)-4-phenylthiazole

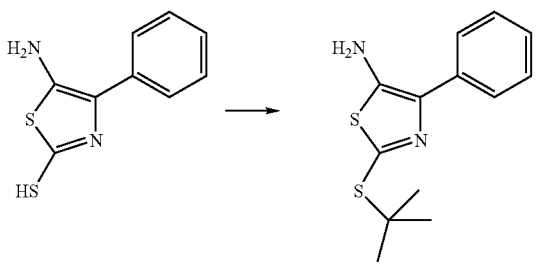

To a suspension of 5-amino-2-mercapto-4-phenylthiazole (210 mg, 1.01 mmol) in water (1.0 ml) and tert-butanol (82 mg, 1.1 mmol) was added concentrated sulfuric acid (3.0 ml) with cooling to ca. 20° C. After 1.5 hr at ambient temperature a further portion of tert-butanol in water (300 μl, 1.0 M, 300 μmol) was added. After 1.5 hr the mixture was poured into excess aqueous sodium bicarbonate and extracted three times into dichloromethane (total 120 ml). The combined organic phases were washed with brine, dried over sodium sulfate, filtered and concentrated in vacuo. Flash chromatography on silica gel (ethyl acetate/hexanes) yielded 5-amino-2-(tent-butylsulfanyl)-4-phenylthiazole (220 mg, 82%).

Example 38

5-amino-2-(tent-butylsulfinyl)-4-phenylthiazole

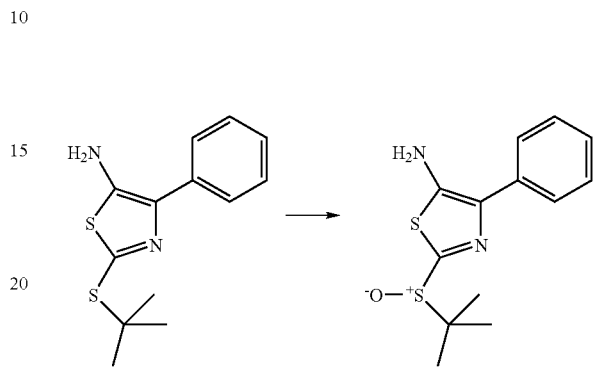

To 5-amino-2-(tent-butylsulfanyl)-4-phenylthiazole (102 mg, 385 mol) in acetic acid (5.0 ml) was added aqueous hydrogen peroxide (218 μl, 30% wt, 1.9 mmol) dropwise at ambient temperature. After 5 hr the mixture was partitioned between dichloromethane (50 ml) and water (50 ml). The aqueous phase was separated and extracted with dichloromethane (20 ml). The combined organic phases were washed with saturated aqueous sodium bicarbonate, dried over sodium sulfate, filtered and concentrated in vacuo to yield essentially pure 5-amino-2-(tent-butylsulfinyl)-4-phenylthiazole (110 mg, quant.).

Example 39

5-amino-4-phenyl-2-(trifluoromethylsulfanyl)thiazole

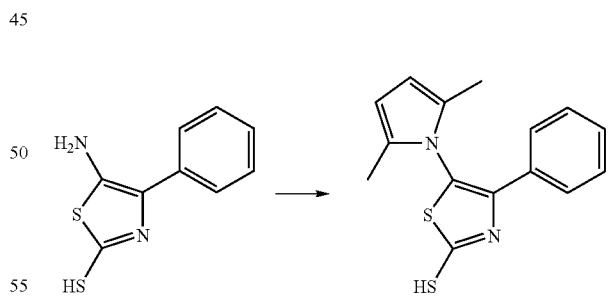

A suspension of 5-amino-2-mercapto-4-phenylthiazole (503 mg, 2.41 mmol) in acetic acid (5.0 ml) was treated with hexane-2,5-dione (290 μl, 2.47 mmol) at ambient temperature for 14 hr and then heated to reflux for 3 hr. The mixture became homogeneous at reflux and on cooling deposited a precipitate which was recovered by filtration, washed with acetic acid (3×1.0 ml) and dried in vacuo to yield the pure pyrrolidino-thiazole (624 mg, 90%) as a bright yellow microcrystalline solid.

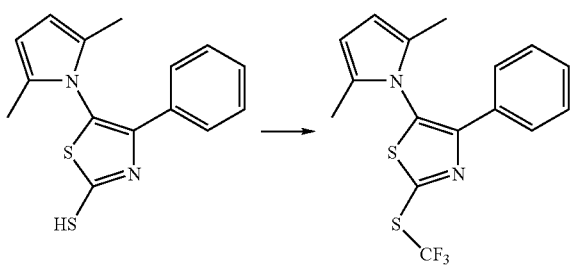

A solution of the mercapto-thiazole (201 mg, 701 mol) and potassium carbonate (291 mg, 2.11 mmol) in DMF (2.0 ml) was saturated with trifluoromethyl iodide by bubbling for 5 min, and the vessel sealed and heated at 50° C. for 30 min. The cooled mixture was again saturated with trifluoromethyl iodide, and heated to 100° C. for 1.5 hr. The mixture was once more saturated with trifluoromethyl iodide, returned to 100° C. (total 24 hr) and allowed to cool. The mixture was poured into water and extracted three times into ethyl acetate (total 100 ml). The combined organic phases were washed with water and brine, dried over magnesium sulfate, filtered and concentrated in vacuo. Flash chromatography on silica gel (ethyl acetate/hexanes) yielded the pure (trifluoromethylsulfanyl)-thiazole (72 mg, 29%) as a colorless crystalline film.

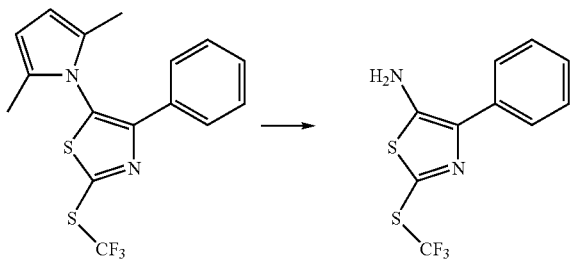

A suspension of the thiazole (72 mg) and hydroxylamine hydrochloride (71 mg, 1.0 mmol) in ethanol (5.0 ml) was heated to reflux for 17 hr, diluted with acetic acid (3 ml), refluxed for a further 2 hr, and concentrated to ca. 3 ml. The cooled mixture was treated with aqueous hydroxylamine (1.0 ml, 50% wt) and returned to reflux for 42 hr. The mixture was treated with water (50 ml) and saturated aqueous sodium bicarbonate (50 ml) and extracted three times into dichloromethane (total 100 ml). The combined organic phases were washed with brine, dried over sodium sulfate, filtered and concentrated in vacuo. Flash chromatography on silica gel (ethyl acetate/hexanes) yielded pure 5-amino-4-phenyl-2-(trifluoromethylsulfanyl)thiazole (12.5 mg, 22%).

Example 40

5-amino-4-phenyl-2-(trifluoromethyl)thiazole

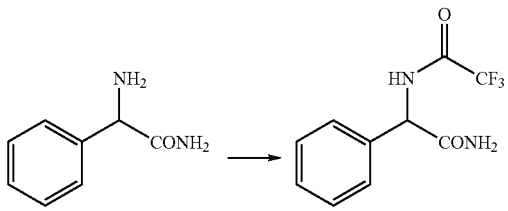

α-Aminophenylacetamide (2.00 g, 13.3 mmol) in methanol (50 ml) at 0° C. was treated with ethyl trifluoroacetate (3.2 ml, 27 mmol) for 30 min and allowed to warm to ambient temperature for 18 hr. The mixture was concentrated in vacuo, made homogeneous with methanol and again concentrated top yield the pure trifluoroacetamide (3.27 g, quant.).

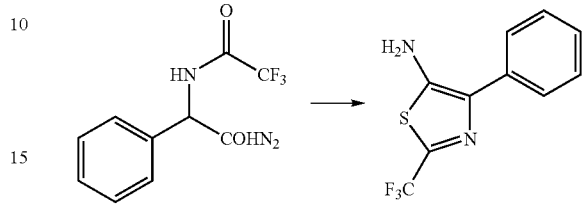

The trifluoroacetamide (881 mg, 3.58 mmol) and Lawesson's reagent (1.45 g, 3.59 mmol) were treated together with anhydrous pyridine (7.2 ml) and the mixture heated to 100° C. for 20 hr. The cooled mixture was poured into saturated aqueous sodium bicarbonate and extracted three times into chloroform (total 120 ml). The combined organic phases were washed with water containing one tenth volume saturated aqueous sodium bicarbonate, and brine, and dried over sodium sulfate. Filtration and concentration in vacuo yielded a red-brown oil (829 mg). The crude was treated with aqueous sodium hydroxide (25 ml, 1.0 N) for 15 min and extracted three times into dichloromethane (total 100 ml). The combined organic phases were washed with aqueous sodium hydroxide (25 ml, 1.0 N) and brine, dried over sodium sulfate, filtered and concentrated in vacuo. Flash chromatography on silica gel (ethyl acetate/hexanes) yielded pure 5-amino-4-phenyl-2-(trifluoromethyl)thiazole (65 mg, 7.5%).

Example 41

3-amino-4-phenyl-1,2,5-thiadiazole

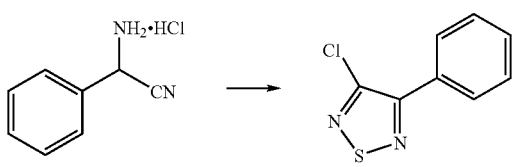

To a solution of sulfur monochloride (24.0 g, 178 mmol) in DMF (30 ml) at 0° C. was added α-aminophenylacetonitrile hydrochloride (10.0 g, 59.3 mmol) portionwise over 20 min. After 40 min the mixture was allowed to warm to ambient temperature for 20 min, diluted with DMF (20 ml) and stirred for a further 20 hr before pouring into ice-water. The mixture was extracted with ether (200 ml), filtered, and the extracted twice more with ether (2×50 ml). The combined organic phases were washed with brine, dried over magnesium sulfate and concentrated in vacuo to give 3-chloro-4-phenyl-1,2,5-thiadiazole as a mobile orange oil (10.1 g, 87%). Short-path distillation of this oil (9.35 g) at reduced pressure yielded a clear, colorless oil (7.75 g, 83%) which crystallized on standing.

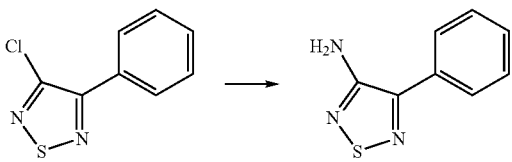

3-Chloro-4-phenyl-1,2,5-thiadiazole (3.19 g, 16.2 mmol) in THF (32 ml) at 0° C. was treated dropwise with a solution of lithium bis(trimethylsilyl)amide in THF (17.0 ml, 1.0 M, 17.0 mmol). After 10 min the mixture allowed to warm to ambient temperature for 1.5 hr, treated with 1N hydrochloric acid, and extracted three times into ether (total 300 ml). The combined organic phases were washed with saturated aqueous sodium bicarbonate and brine, and dried over magnesium sulfate and concentrated in vacuo. The residue was dissolved in methanol (50 ml) and triethylamine (0.5 ml) was heated to reflux for 15 hr and again concentrated in vacuo. Flash chromatography on silica gel (ethyl acetate/hexanes) yielded 3-amino-4-phenyl-1,2,5-thiadiazole (1.96 g, 68%) as a colorless solid.

Example 42

5-amino-2-methyl-4-phenylthiazole

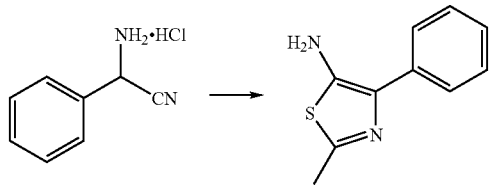

To a suspension of α-aminophenylacetonitrile hydrochloride (3.37 g, 20.0 mmol) and powdered sulfur (641 mg, 20.0 mmol) in ethanol (20 ml) at 0° C. was added triethylamine (4.18 ml, 30.0 mmol) and then acetaldehyde (2.3 ml, 41 mmol). The vessel was sealed and heated to 60-70° C. for 1 hr. The cooled mixture was filtered and concentrated in vacuo, and the residue treated with ethanol (20 ml) and hydrochloric acid (20 ml, 1N) for 15 hr. The mixture was treated with aqueous sodium carbonate and extracted three times into ethyl acetate (total 300 ml). The combined organic phases were washed with brine, dried over sodium sulfate and concentrated in vacuo to give a dark brown oil. Flash chromatography on silica gel (ethyl acetate/hexanes) yielded 5-amino-2-methyl-4-phenylthiazole (1.31 g, 34%), which crystallized from toluene.

Example 43

5-amino-2-methyl-4-phenylthiazole

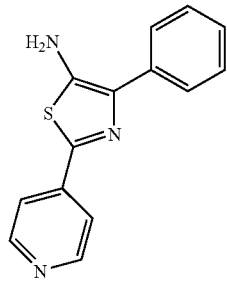

A suspension of α-aminophenylacetonitrile hydrochloride (1.69 g, 10.0 mmol), powdered sulfur (321 mg, 10.0 mmol) and 4-pyridinecarboxaldehyde (1.91 ml, 20.0 mmol) in ethanol (10 ml) was treated with triethylamine (2.09 ml, 15.0 mmol), and the mixture stirred at 50° C. for 80 min. The cooled mixture was diluted with ethanol (5 ml) and treated with aqueous hydroxylamine (700 μl, 50% wt, 11 mmol) at ambient temperature for 15 hr, and diluted with dichloromethane (50 ml). Saturated aqueous sodium bicarbonate was added and the separated aqueous phase was extracted twice more with dichloromethane (total 100 ml). The combined organic phases were dried over sodium sulfate and concentrated in vacuo to give a dark brown oily foam (3.23 g). Flash chromatography on silica gel (ethyl acetate/hexanes) yielded 5-amino-2-(4-pyridyl)-4-phenylthiazole (1.41 g, 56%).

Example 44

2,4-diphenylthiazol-5-amine

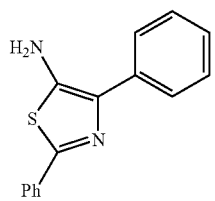

2,4-diphenylthiazol-5-amine was prepared according to the procedures described in K. Gewald, H. Schonfelder, U. Hain; *J. Prakt. Chem.*, 1974, 361, 299-303.

Example 45

4-phenyl-2-(pyridin-2-yl)thiazol-5-amine

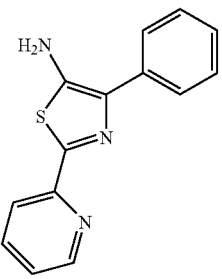

4-phenyl-2-(pyridin-2-yl)thiazol-5-amine was prepared according to the procedures described in K. Gewald, H. Schonfelder, U. Hain; *J. Prakt. Chem.*, 1974, 361, 299-303

Example 46

4-phenyl-2-(pyridin-3-yl)thiazol-5-amine

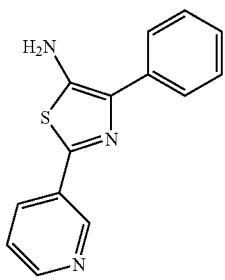

4-phenyl-2-(pyridin-3-yl)thiazol-5-amine was prepared according to the procedures described in K. Gewald, H. Schonfelder, U. Hain; *J. Prakt. Chem.*, 1974, 361, 299-303

Example 47

5-amino-2-(Fmoc-amino)-4-phenylthiazole

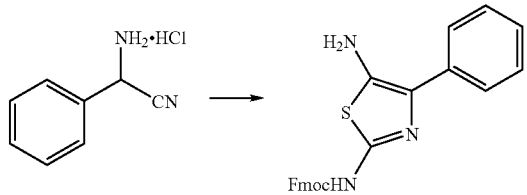

A suspension of α-aminophenylacetonitrile hydrochloride (3.19 g, 18.9 mmol) and Fmoc-isothiocyanate (5.31 g, 18.9 mmol) in DCM was treated with ethyldiisopropylamine (3.62 ml, 20.8 mmol) at 0° C. for 1 hr and then at ambient temperature for 3 hr. The mixture was poured into saturated aqueous sodium bicarbonate and extracted three times into ethyl acetate. The combined organic phases were washed with water and brine, and dried over sodium sulfate and concentrated in vacuo. Flash chromatography on silica gel (ethyl acetate/hexanes) yielded 5-amino-2-(Fmoc-amino)-4-phenylthiazole (3.75 g, 48%).

Example 48

N-(5-amino-4-phenylthiazol-2-yl)acetamide

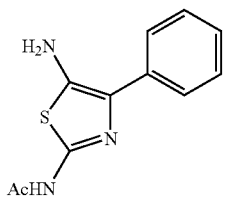

N-(5-amino-4-phenylthiazol-2-yl)acetamide was prepared according to procedures similar to those described in example 47.

Example 49

N-(5-amino-4-phenylthiazol-2-yl)benzamide

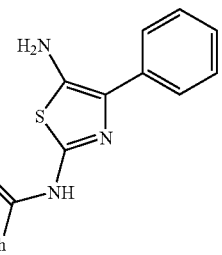

N-(5-amino-4-phenylthiazol-2-yl)benzamide was prepared according to procedures similar to those described in example 47.

Example 50

Ethyl 5-amino-4-phenylthiazol-2-ylcarbamate

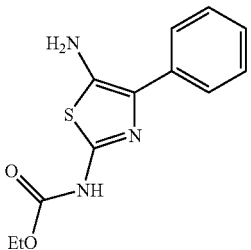

ethyl 5-amino-4-phenylthiazol-2-ylcarbamate was prepared according to procedures similar to those described in example 47.

Example 51

N-(5-amino-4-(2-chlorophenyl)thiazol-2-yl)acetamide

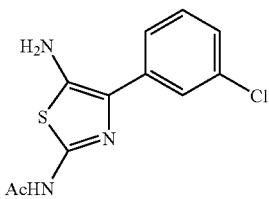

N-(5-amino-4-(2-chlorophenyl)thiazol-2-yl)acetamide was prepared according to procedures similar to those described in example 47.

Example 52

(9H-fluoren-9-yl)methyl 5-amino-4-(2-chlorophenyl) thiazol-2-ylcarbamate

(9H-fluoren-9-yl)methyl 5-amino-4-(2-chlorophenyl) thiazol-2-ylcarbamate was prepared according to procedures similar to those described in example 47.

Example 53

5-amino-2-(1-imidazolyl)-4-phenylthiazole

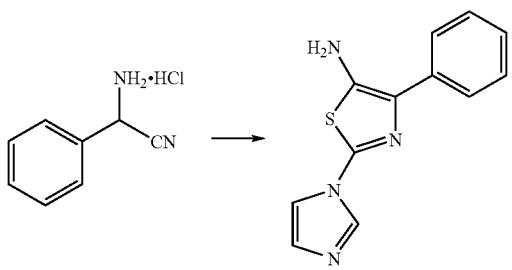

A suspension of α-aminophenylacetonitrile hydrochloride (5.01 g, 29.7 mmol) and thiocarbonyl diimidazole (5.30 g, 29.7 mmol) in DCM (100 ml) was treated with ethyldiisopropylamine (5.69 ml, 32.7 mmol) at 0° C. for 15 min and then at ambient temperature for 3 hr. The mixture was poured into saturated aqueous sodium bicarbonate (50 ml) and water (150 ml), and extracted three times into dichloromethane (total 300 ml). The combined organic phases were washed with brine, dried over magnesium sulfate and concentrated in vacuo to give a dark brown oil (8.18 g). Flash chromatography on silica gel (ethyl acetate/hexanes) yielded 5-amino-2-(1-imidazolyl)-4-phenylthiazole (2.47 g, 34%).

Example 54

MeAla-Chg-Pro peptide amide of 2,5-diamino-4-phenylthiazole

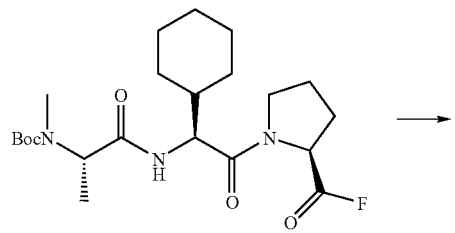

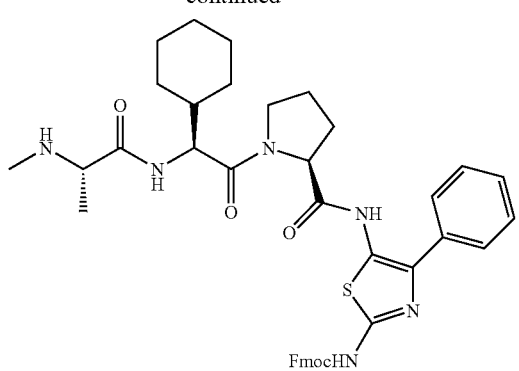

5-Amino-2-(Fmoc-amino)-4-phenylthiazole (250 mg, 605 μmol) was treated with the acid fluoride (730 μmol; derived form Boc-MeAla-Chg-Pro-OH as previously described) and pyridine (147 μl, 1.82 mmol) in dichloromethane (2.0 ml) at ambient temperature for 6 days. The mixture was poured into saturated aqueous sodium bicarbonate and extracted three times into dichloromethane (total 100 ml). The combined organic phases were washed with brine, dried over magnesium sulfate and concentrated in vacuo to yield the crude peptide amide as a yellow oil (525 mg), used subsequently without purification.

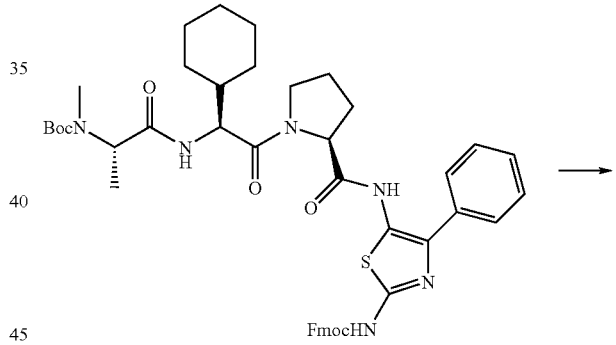

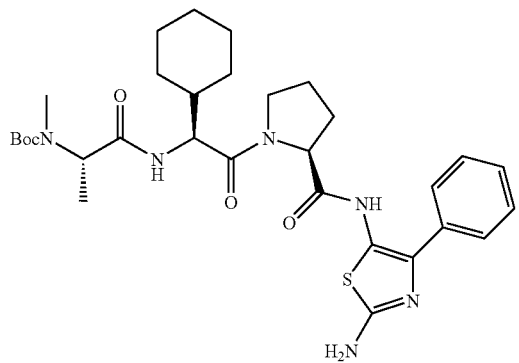

The crude peptide amide in DMF (9.0 ml) was treated with piperidine (1.0 ml) at ambient temperature for 20 min and then concentrated in vacuo. Flash chromatography on silica gel (ethyl acetate/hexanes) yielded the 2,5-diamino-4-phenylthiazole peptide amide (228 mg, 61% for 2 steps).

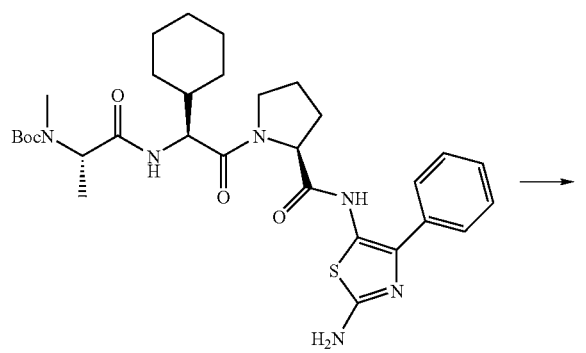

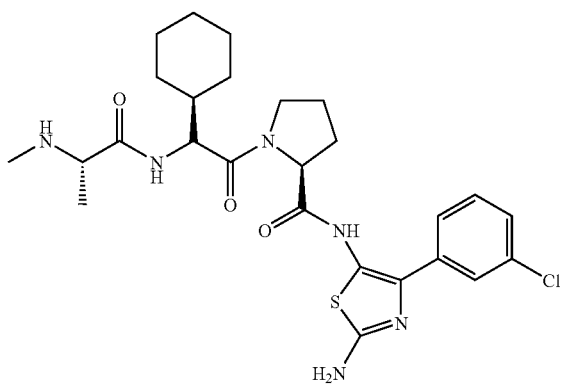

The crude peptide amide (48 mg, 78 µmol) in dichloromethane (2.0 ml) was treated with trifluoroacetic acid (2.0 ml) at ambient temperature for 30 min. The mixture was concentrated in vacuo, made homogeneous with dichloromethane and again concentrated. The residue was purified by preparative reverse phase HPLC (acetonitrile/water) to yield the fully deprotected peptide amide trifluoroacetic acid salt (42 mg, 73%) as a white amorphous solid.

Example 55

MeAla-Chg-Pro peptide amide of 2,5-diamino-4-(3-chlorophenyl)thiazole

MeAla-Chg-Pro peptide amide of 2,5-diamino-4-(3-chlorophenyl)thiazole was prepared using the same procedures described in example 55.

Example 56

MeAla-Chg-Pro amide of 5-amino-2-(pivaloylamino)-4-phenylthiazole

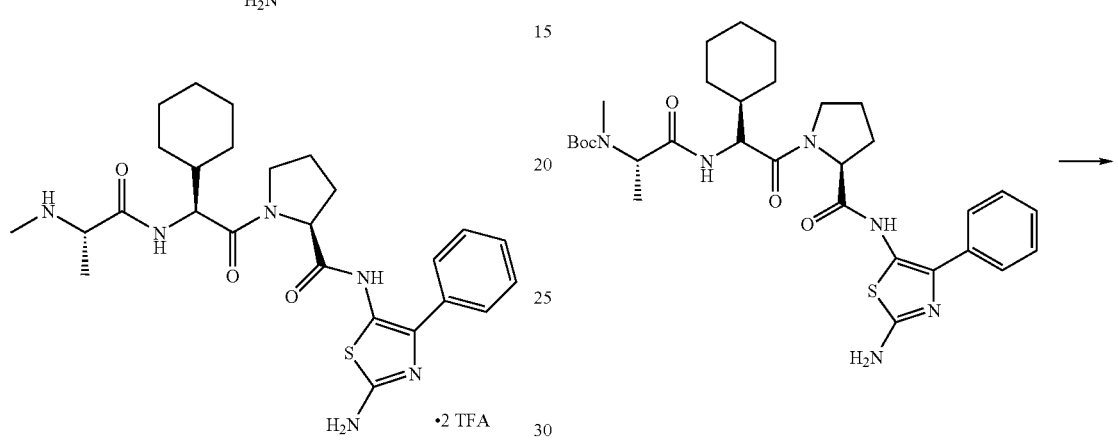

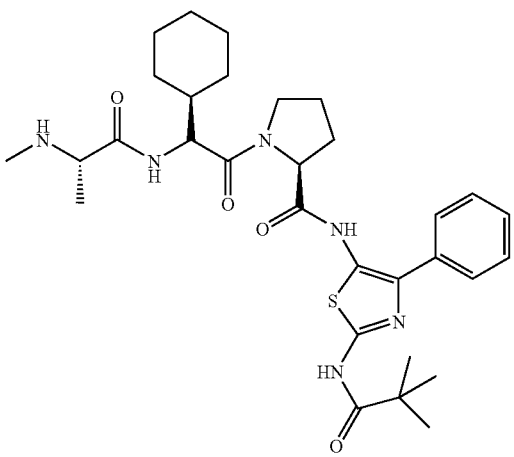

The Boc-peptide amino-thiazole (48 mg, 78 µmol) and ethyldiisopropylamine (140 µl, 0.80 mmol) in dichloromethane (2.0 ml) were treated with pivaloyl chloride (50 µl, 0.40 mmol) at ambient temperature for 3 hr, and then with saturated aqueous sodium bicarbonate and extracted three times into dichloromethane (total 60 ml). The combined organic phases were washed with brine, dried over magnesium sulfate and concentrated in vacuo. The crude oil was treated with trifluoroacetic acid (5.0 ml) in dichloromethane (5.0 ml) at ambient temperature for 20 min. The mixture was concentrated in vacuo, made homogeneous with dichloromethane and again concentrated. The residue was dissolved in aqueous acetic acid (50%) for purification by preparative reverse phase HPLC (acetonitrile/water) to yield the pure peptide amide trifluoroacetic acid salt (38 mg, 68% for 2 steps) as a white amorphous solid.

Example 57

MeAla-Chg-Pro amide of
5-amino-2-(pivaloylamino)-4-phenylthiazole

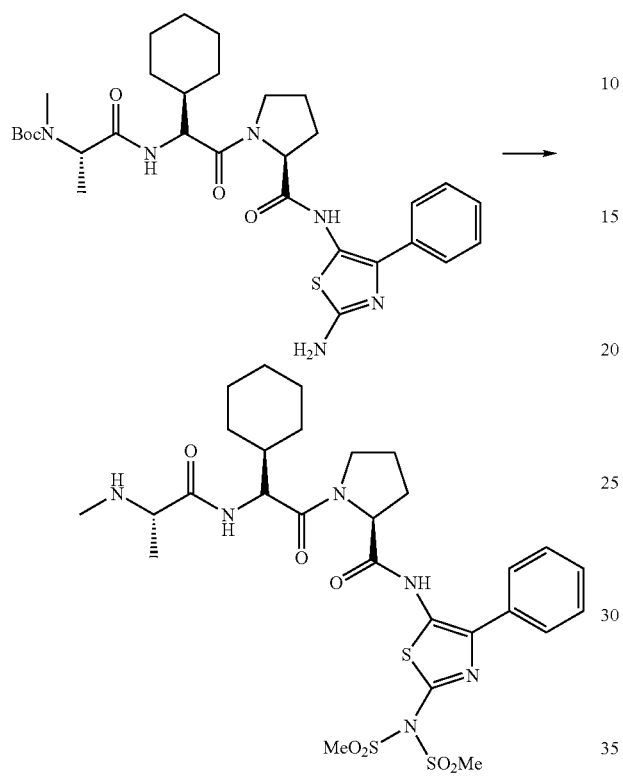

The Boc-peptide amino-thiazole (38 mg, 62 µmol) and ethyldiisopropylamine (107 µl, 0.61 mmol) in dichloromethane (2.0 ml) were treated with methanesulfonyl chloride (24 µl, 0.31 mmol) at ambient temperature for 20 min, and then with saturated aqueous sodium bicarbonate and extracted three times into dichloromethane. The combined organic phases were washed with brine, dried over magnesium sulfate and concentrated in vacuo. The crude oil was treated with trifluoroacetic acid (4 ml) in dichloromethane (4 ml) at ambient temperature for 20 min. The mixture was concentrated in vacuo, made homogeneous with dichloromethane and again concentrated. The residue was dissolved in aqueous acetic acid (50%) for purification by preparative reverse phase HPLC (acetonitrile/water) to yield the pure peptide amide trifluoroacetic acid salt (11 mg, 23% for 2 steps) as a white amorphous solid.

Example 57

2-(acetylamino)-4-amino-5-phenylthiazole

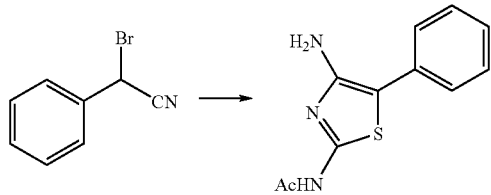

α-Bromophenylacetonitrile (1.08 g, 5.48 mmol) in ethanol (10 ml) was treated with N-acetylthiourea (649 mg, 5.49 mmol) at ambient temperature for 4 hr, and then heated to reflux for 3.5 hr. The cooled mixture was concentrated in vacuo and then partitioned between dichloromethane and saturated aqueous sodium bicarbonate. The organic phase was washed with brine, dried over sodium sulfate, filtered and concentrated in vacuo. Flash chromatography on silica gel (ethyl acetate/hexanes) yielded 2-(acetylamino)-4-amino-5-phenylthiazole (295 mg, 23%).

Example 58

2,5-diphenylthiazol-4-amine

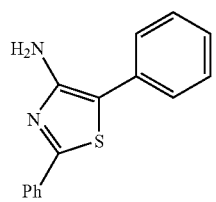

2,5-diphenylthiazol-4-amine was prepared using the same procedures described in example 57.

Example 59

5-phenyl-2-(pyrazin-2-yl)thiazol-4-amine

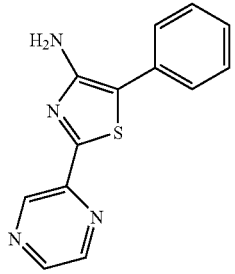

5-phenyl-2-(pyrazin-2-yl)thiazol-4-amine was prepared using the same procedures described in example 57.

Example 60

5-amino-1-(3'-nitrophenyl)pyrazole

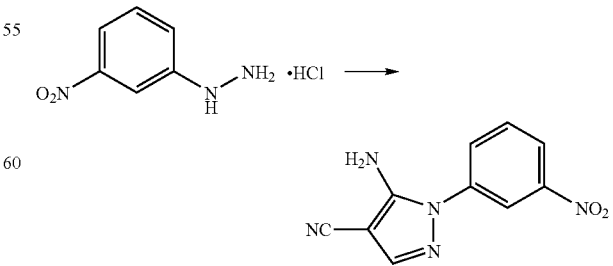

3-Nitrophenylhydrazine hydrochloride (7.03 g, 36.3 mmol), diisopropylethylamine (9.5 ml, 54.5 mmol), and ethanol (60 ml) were stirred under nitrogen at room temperature for 2 h. Ethoxymethylenemalononitrile (4.52 g, 36.3 mmol) was added, after which the reaction was refluxed for 1 h. Reaction was cooled to room temperature. Solvent was removed under reduced pressure until precipitate crashed out. The solid was filtered to yield 6.54 g of the cyclized product (78% yield).

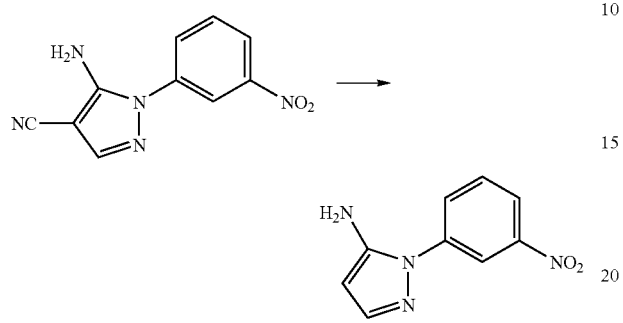

5-amino-1-(3'-nitrophenyl)-4-cyanopyrazole (559 mg, 2.44 mmol) and phosphoric acid (86%, 6 ml) were refluxed at 170° C. for 15 h. The reaction was cooled to room temperature and neutralized with ammonium hydroxide. The organics were extracted three times with diethyl ether (total 40 ml), washed with brine, and dried over magnesium sulfate. Removal of solvent gave 5-amino-1-(3'-nitrophenyl)-pyrazole as a yellow powder (398 mg, 80% yield).

Example 61

1-(2-fluorophenyl)-1H-pyrazol-5-amine

1-(2-fluorophenyl)-1H-pyrazol-5-amine was prepared using the same procedures described in example 60.

Example 62

1-(3-chlorophenyl)-1H-pyrazol-5-amine

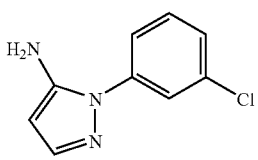

1-(3-chlorophenyl)-1H-pyrazol-5-amine was prepared using the same procedures described in example 60.

Example 63

1-(3-fluorophenyl)-1H-pyrazol-5-amine

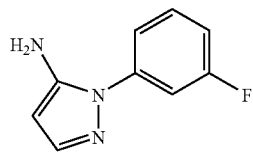

1-(3-fluorophenyl)-1H-pyrazol-5-amine was prepared using the same procedures described in example 60.

Example 64

1-(3-bromophenyl)-1H-pyrazol-5-amine

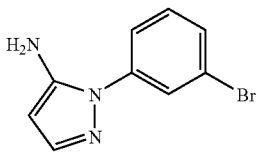

1-(3-bromophenyl)-1H-pyrazol-5-amine was prepared using the same procedures described in example 60.

Example 65

1-(3-trichloromethylphenyl)-1H-pyrazol-5-amine

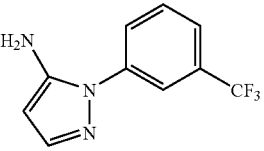

1-(3-trichloromethylphenyl)-1H-pyrazol-5-amine was prepared using the same procedures described in example 60.

Example 66

1-(pyridin-2-yl)-1H-pyrazol-5-amine

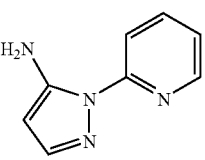

1-(pyridin-2-yl)-1H-pyrazol-5-amine was prepared using the same procedures described in example 60.

Example 67

1-(3-methoxyphenyl)-1H-pyrazol-5-amine

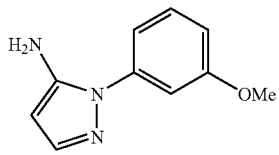

1-(3-methoxyphenyl)-1H-pyrazol-5-amine was isolated following decyanation of 5-amino-4-cyano-1-(3'-methoxyphenyl)pyrazole in example 60.

Example 67

1-(3-hydroxyphenyl)-1H-pyrazol-5-amine

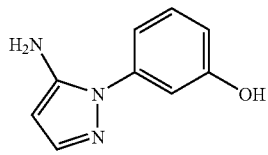

1-(3-hydroxyphenyl)-1H-pyrazol-5-amine was prepared using the same procedures described in example 60.

Example 68

4-amino-5-phenyl-1,2,3-thiadiazole

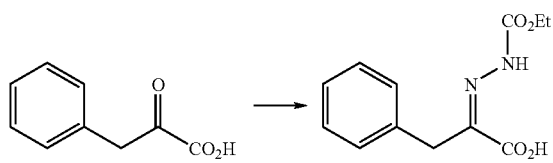

Phenylpyruvic acid (25 g, 149 mmol) and ethyl carbazate (16 g, 149 mmol) were refluxed in benzene (225 ml) for 2 hr, and the mixture concentrated in vacuo. The crude was dissolved in minimum warm dichloromethane to yield the hydrazone as a yellow precipitate upon cooling to ambient temperature, isolated by filtration (30.4 g, 81%) and used without further purification.

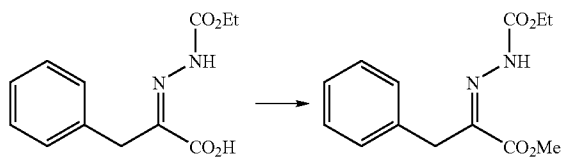

Diazomethane was generated by adding a solution of Diazald (N-methyl-N-nitroso-p-toluenesulfonamide; 18.6 g, 86.9 mmol) in diethyl ether (180 ml) to a solution of potassium hydroxide (18.2 g, 325 mmol) in water (37 ml) and 2-(2-ethoxyethoxy)-ethanol (37 ml) at 65° C., dropwise over 45 min. Distillation thus produced an ethereal solution of diazomethane which was added directly to a stirred solution of the hydrazone (10.9 g, 43.5 mmol) in methanol (150 ml) at 0° C. The system was rinsed with excess diethyl ether until distillate became clear, the mixture treated with acetic acid (1 ml), and concentrated in vacuo. The resulting oil was partitioned between ethyl acetate (200 ml) and sodium bicarbonate (200 ml), and the organic phase dried over sodium sulfate. Filtration and concentration in vacuo yielded the methyl ester as a yellow solid (10.2 g, 89%).

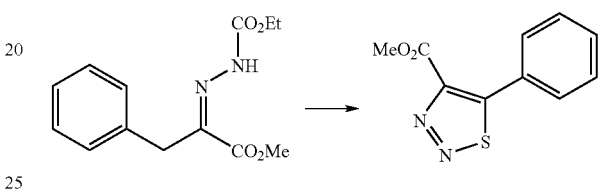

The hydrazone-methyl ester (10.2 g, 38.6 mmol) was treated with thionyl chloride (25 ml, 343 mmol) at ambient temperature for 24 hr, and the mixture concentrated in vacuo. Crystallization from hexanes yielded the thiadiazole-methyl ester (4.81 g, 56%).

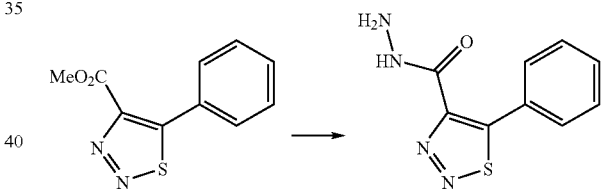

The thiadiazole-methyl ester (2.79 g, 12.7 mmol) was treated with hydrazine hydrate (1.09 ml, 93.9 mmol) in methanol (50 ml) at ambient temperature for 24 hr, and the resulting white precipitate recovered by filtration. Recrystallization from isopropanol yielded the thiadiazole-hydrazide (3.99 g, 83%).

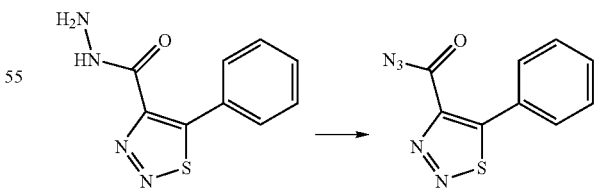

The thiadiazole-hydrazide (3.99 g, 18.1 mmol) in water (40 ml) and concentrated hydrochloric acid (1.8 ml, 21.9 mmol) was treated dropwise with a solution of sodium nitrite (1.52 g, 21.3 mmol) in water (15 ml) at 0° C. for 2 hr. The resulting precipitate was recovered by filtration to yield the thiadiazole-acid azide as an off-white solid (3.95 g, 94%).

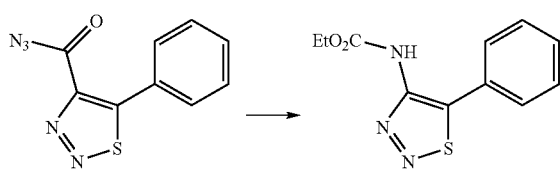

According to the procedures described in K. Masuda et al.; *Chem. Pharm. Bull.,* 1981, 29, 1743-1747, the thiadiazole-acid azide (3.95 g, 17.1 mmol) was at reflux in ethanol (40 ml) for 45 min, and the mixture concentrated in vacuo. Crystallization from benzene yielded the ethyl carbamate (3.37 g, 74%).

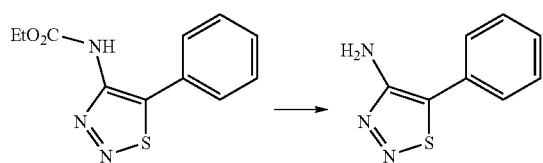

The ethyl carbamate (399 mg, 1.60 mmol) and hydrogen bromide in acetic acid (3 ml, 30% wt) were heated in a sealed vessel at 80° C. for 18 hr. The cooled mixture was partitioned between ethyl acetate (15 ml) and water (15 ml), and the organic phase concentrated in vacuo. Flash chromatography on silica gel (ethyl acetate/hexanes) yielded 4-amino-5-phenyl-1,2,3-thiadiazole (136 mg, 49%).

Example 69

4-amino-5-phenylisoxazole

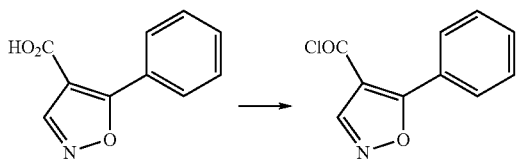

5-Phenyl-4-isoxazolecarboxylic acid (460 mg, 2.36 mmol) and thionyl chloride (1.71 ml, 23.6 mmol) were heated at reflux for 3 hr, and the mixture concentrated in vacuo to yield the acid chloride which was used without purification.

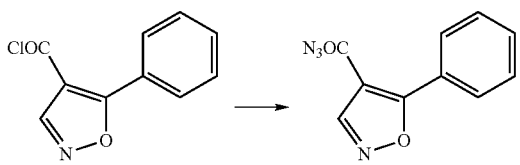

The crude acid chloride in acetone (7 ml) was treated with a solution of sodium azide (165 mg, 2.62 mmol) in water (2 ml) at 0° C. for 1.5 hr, and allowed to warm to ambient temperature and concentrated in vacuo. The resulting white solid was washed with water and dried in vacuo, and used without purification.

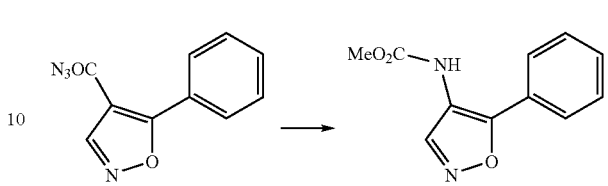

The acid azide (409 mg, 1.91 mmol) was heated at reflux in methanol for 6 hr, and the mixture concentrated in vacuo to yield the methyl carbamate as a white solid, used without purification.

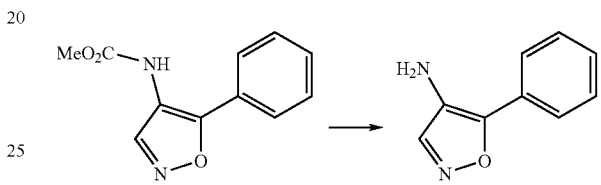

The methyl carbamate (378 mg, 1.73 mmol) was treated with hydrobromic acid (13 ml, 48% wt, 115 mmol), made homogeneous with acetic acid (2 ml), and heated at 65° C. for 48 hr, and allowed to cool. The mixture was neutralized with aqueous sodium hydroxide and extracted with ethyl acetate (2×125 ml). The combined organic phases were dried over sodium sulfate and concentrated in vacuo to yield 4-amino-5-phenylisoxazole as a white solid (193 mg, 70%).

Example 70

Synthesis of 5-alkyl-2-amino-3-phenylthiophenes

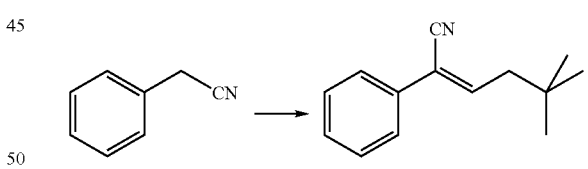

Benzyl cyanide (2.33 ml, 20 mmol) was treated with Verkade's base (2,8,9-trimethyl-2,5,8,9-tetraaza-1-phosphabicyclo[3.3.3]undecane; 441 mg, 2.0 mmol) and 3,3-dimethylbutyraldehyde (2.64 ml, 200 mmol) in methanol (4 ml) and the mixture heated in a sealed vessel at 45° C. for 16 hr. The cooled mixture was concentrated in vacuo to yield the unsaturated nitrile as a colorless oil, used without purification.

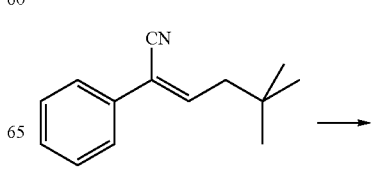

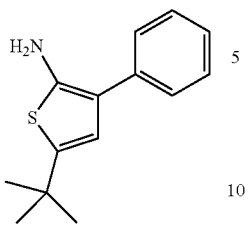

The nitrile (10.0 mmol), potassium carbonate (2.34 g, 23.4 mmol) and powdered sulfur (330 mg, 10.3 mmol) in ethanol (2 ml) were heated in a sealed vessel at 160° C. for 24 hr. The cooled mixture was diluted with water, extracted twice into diethyl ether and the combined organics concentrated in vacuo. Flash chromatography on silica gel (ethyl acetate/hexanes) yielded 5-amino-2-tert-butyl-4-phenylthiazole (75%).

Example 71

5-methyl-3-phenylthiophen-2-amine

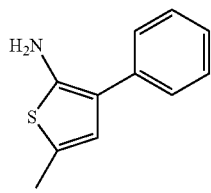

5-methyl-3-phenylthiophen-2-amine was prepared using the same procedures described in example 70.

Example 72

5-isopropyl-3-phenylthiophen-2-amine

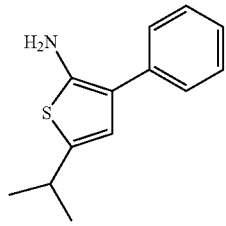

5-isopropyl-3-phenylthiophen-2-amine was prepared using the same procedures described in example 70.

Example 73

2-amino-5-chloro-3-phenylthiophene

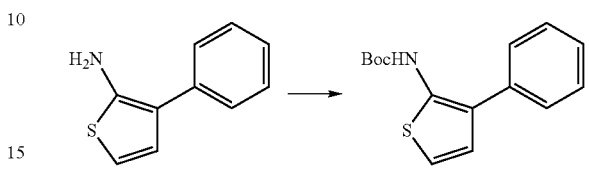

2-Amino-3-phenyl-thiophene (12.0 mmol) in THF (7 ml) was treated with di-tent-butyl dicarbonate (2.97 g, 13.3 mmol) and diisopropylethylamine (3.15 ml, 18.1 mmol) at ambient temperature for 60 hr, and the mixture concentrated in vacuo. Flash chromatography on silica gel (ethyl acetate/hexanes) yielded 2-(N-Boc-amino)-3-phenyl-thiophene (1.98 g, 59%).

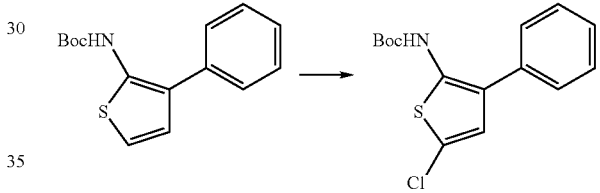

To 2-(N-Boc-amino)-3-phenyl-thiophene (89 mg, 0.32 mmol) in dichloromethane (4 ml) at 0° C. was slowly added N-chlorosuccinimide (48 mg, 0.36 mmol), and the mixture allowed warm to ambient temperature for 16 hr. The mixture was diluted with dichloromethane, washed with water, and the organic phase concentrated in vacuo. Flash chromatography on silica gel (ethyl acetate/hexanes) yielded 2-(N-Boc-amino)-5-chloro-3-phenyl-thiophene (66 mg, 66%).

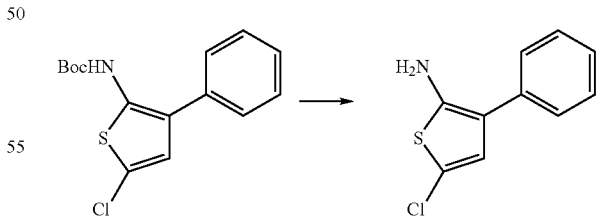

2-(N-Boc-amino)-5-chloro-3-phenyl-thiophene (66 mg, 0.21 mmol) was treated with trifluoroacetic acid (1 ml) in dichloromethane (3 ml) at ambient temperature for 1 hr. The mixture was diluted with DMF (1 ml) and the more volatile materials removed under reduced pressure. The resulting DMF solution of 2-amino-5-chloro-3-phenylthiophene was used in the subsequent coupling step without purification.

Example 74

1-Methyl-4-(methylamino)-3-phenylpyrazole

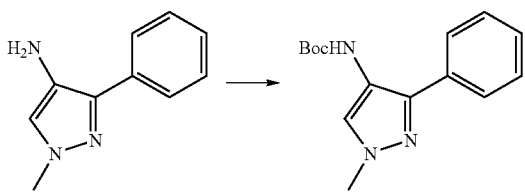

To 1-methyl-4-amino-3-phenylpyrazole (572 mg, 3.30 mmol) and di-tert-butyl dicarbonate (799 mg, 3.66 mmol) in THF (10 ml) and water (3 ml) was added dropwise saturated aqueous sodium bicarbonate (3 ml, 1.2 M, 3.6 mmol). The mixture was stirred at ambient temperature for 7 hr and then poured into aqueous citric acid (0.5 M) and extracted three times into ether (total 100 ml). The combined organic phases were washed with saturated aqueous sodium bicarbonate and brine, dried over magnesium sulfate and concentrated in vacuo to yield the crude carbamate as a brown oil (920 mg), used subsequently without purification.

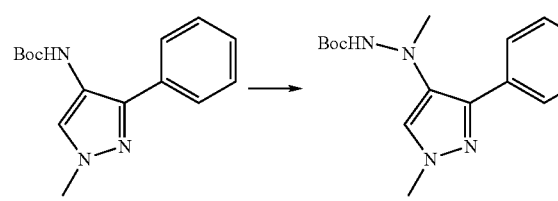

A suspension of sodium hydride in mineral oil (327 mg, 60% wt, 8.18 mmol) was washed with THF (2×5 ml) and suspended in THF (3.0 ml) at 0° C. To this was added dropwise the pyrazole (744 mg, 2.72 mmol) in THF (5.0 ml), and after 15 min, methyl iodide (187 μl, 3.00 mmol). After a further 30 min at 0° C. the mixture was allowed to warm to ambient temperature for 18 hr and then treated with saturated aqueous ammonium chloride and sufficient water to dissolve solids. The mixture was extracted three times into ether (total 120 ml), and the combined organic phases washed with brine, dried over magnesium sulfate and concentrated in vacuo to yield the crude N-methyl carbamate as a amber oil (750 mg, 96%), used without purification.

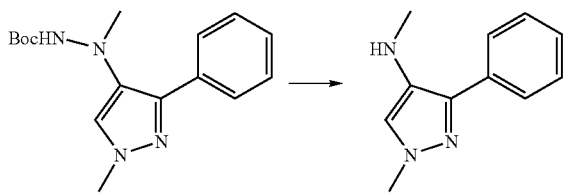

The crude N-methyl carbamate in DCM (1.0 ml) was treated with trifluoroacetic acid (1.0 ml) at ambient temperature for 40 min. The mixture was concentrated in vacuo, made homogeneous with dichloromethane and again concentrated to yield essentially pure 1-methyl-4-(methylamino)-3-phenylpyrazole (150 mg, quant.) as a brown oil.

Example 75

N-methyl-4-phenyl-1,2,3-thiadiazol-5-amine

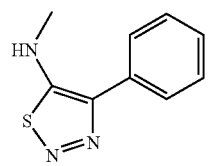

N-methyl-4-phenyl-1,2,3-thiadiazol-5-amine was prepared using the same procedures described in example 74.

Example 76

1-tent-Butyl-4-amino-3-phenylpyrazole and 1-tent-butyl-4-amino-5-phenylpyrazole

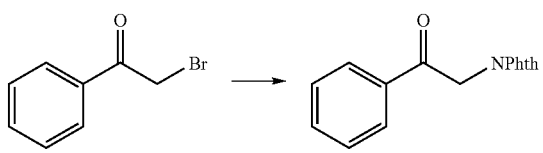

A solution of 2-bromoacetophenone (30.0 g, 151 mmol) in DMF (120 ml) was treated with potassium phthalimide (30.8 g, 166 mmol) portionwise at ambient temperature, and then heated to 40° C. for 3.5 hr. The cooled mixture was poured into water (600 ml) and extracted with chloroform (300 ml then 100 ml). The combined organic phases were washed with sodium hydroxide (200 ml, 0.2 N), water (2×100 ml) and brine (100 ml), dried over magnesium sulfate and concentrated in vacuo. The resulting cream solid was suspended in ether (100 ml), recovered by filtration, washed with ether (100 ml) and dried in vacuo to yield pure 2-phthalimidoacetophenone as a white solid (34.3 g, 86%).

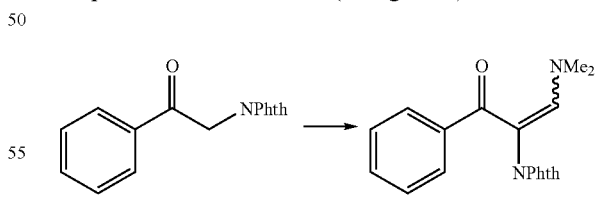

According to the procedures described in C. Chen, K. Wilcoxen, J. R. McCarthy; *Tetrahedron Lett.*, 1988, 39, 8229-8232 a suspension of 2-phthalimidoacetophenone (13.3 g, 50.0 mmol) in dimethylformamide dimethyl acetal (26.7 ml, 200 mmol) was heated at reflux for 28 hr and concentrated in vacuo. The resulting amber oil was crystallized form isopropanol (100 ml) and washed with isopropanol (2×5 ml) to yield of 3-(dimethylamino)-1-phenyl-2-phthalimido-2-propen-1-one as yellow needles (13.7 g, 85%).

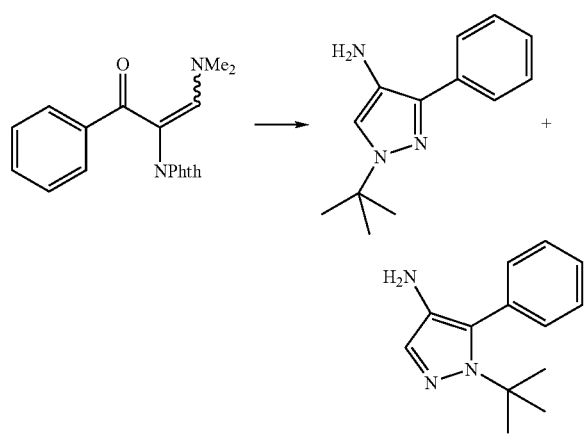

A mixture of 3-(dimethylamino)-1-phenyl-2-phthalimido-2-propen-1-one (3.00 g, 9.38 mmol) and tert-butyl hydrazine hydrochloride (1.29 g, 10.3 mmol) in ethanol (94 ml) and water (9.4 ml) was stirred at ambient temperature for 64 hr and then heated at reflux for 24 hr. The cooled mixture was treated with hydrazine (590 µl, 18.8 mmol) and returned to reflux for 75 min. On cooling and standing at ambient temperature a precipitate formed. The mixture was filtered, the solid washed with a mixture of ethanol (5 ml) and water (0.5 ml), and the filtrate concentrated in vacuo. The residue was partitioned between ether (250 ml) and saturated aqueous sodium bicarbonate (50 ml) diluted with water (100 ml), and the aqueous phase extracted twice more with ether (2×50 ml). The combined organic phases were washed with brine, dried over sodium sulfate and concentrated in vacuo to give a pale solid (1.92 g). Flash chromatography on silica gel (ethyl acetate/hexanes) yielded 1-tent-butyl-4-amino-3-phenylpyrazole (1.52 g, 75% for 2 steps) and 1-tent-butyl-4-amino-5-phenylpyrazole (114 mg, 6% for 2 steps).

Example 77

1-(2,2,2-trifluoroethyl)-3-phenyl-1H-pyrazol-4-amine and 1-(2,2,2-trifluoroethyl)-5-phenyl-1H-pyrazol-4-amine

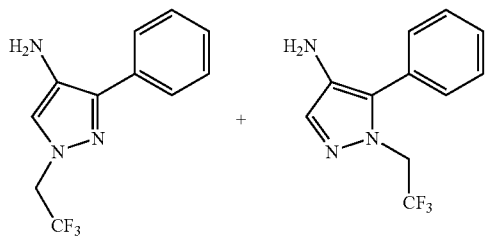

1-(2,2,2-trifluoroethyl)-3-phenyl-1H-pyrazol-4-amine and 1-(2,2,2-trifluoroethyl)-5-phenyl-1H-pyrazol-4-amine were prepared similarly from 2,2,2-trifluoroethylhydrazine according to the procedures described in example 76.

Example 78

IAP Inhibition Assays

In the following experiments was used a chimeric BIR domain referred to as MLXBIR3SG in which 11 of 110 residues correspond to those found in XIAP-BIR3, while the remainder correspond to ML-IAP-BIR. The chimeric protein MLXBIR3SG was shown to bind and inhibit caspase-9 significantly better than either of the native BIR domains, but bound Smac-based peptides and mature Smac with affinities similar to those of native ML-IAP-BIR. The improved caspase-9 inhibition of the chimeric BIR domain MLXBIR3SG has been correlated with increased inhibition of doxorubicin-induced apoptosis when transfected into MCF7 cells.

MLXBIR3SG sequence:
(SEQ ID NO.: 1)
MGSSHHHHHHSSGLVPRGSHMLETEEEEEEGAGATLSRGPAFPGMGSEEL

RLASFYDWPLTAEVPPELLAAAGFFHTGHQDKVRCFFCYGGLQSWKRGDD

PWTEHAKWFPGCQFLLRSKGQEYINNIHLTHSL

TR-FRET Peptide Binding Assay

Time-Resolved Fluorescence Resonance Energy Transfer competition experiments were performed on the Wallac Victor2 Multilabeled Counter Reader (Perkin Elmer Life and Analytical Sciences, Inc.) according to the procedures of Kolb et al (Journal of Biomolecular Screening, 1996, 1(4): 203). A reagent cocktail containing 300 nM his-tagged MLXBIR3SG; 200 nM biotinylated SMAC peptide (AVPI); 5 µg/mL anti-his allophycocyanin (XL665) (CISBio International); and 200 ng/mL streptavidin-europium (Perkin Elmer) was prepared in reagent buffer (50 mM Tris [pH 7.2], 120 mM NaCl, 0.1% bovine globulins, 5 mM DTT and 0.05% octylglucoside). (Alternatively, this cocktail can be made using europium-labeled anti-His (Perkin Elmer) and streptavidin-allophycocyanin (Perkin Elmer) at concentrations of 6.5 nM and 25 nM, respectively). The reagent cocktail was incubated at room temperature for 30 minutes. After incubation, the cocktail was added to 1:3 serial dilutions of an antagonist compound (starting concentration of 50 µM) in 384-well black FIA plates (Greiner Bio-One, Inc.). After a 90 minute incubation at room temperature, the fluorescence was read with filters for the excitation of europium (340 nm) and for the emission wavelengths of europium (615 nm) and a allophycocyanin (665 nm). Antagonist data were calculated as a ratio of the emission signal of allophycocyanin at 665 nm to that of the emission of europium at 615 nm (these ratios were multiplied by a factor of 10,000 for ease of data manipulation). The resulting values were plotted as a function of antagonist concentration and fit to a 4-parameter equation using Kaleidograph software (Synergy Software, Reading, Pa.). Indications of antagonist potency were determined from the IC50 values. Compounds of the invention where found to have IAP inhibitory activity which was demonstrated in this assay.

Fluorescence Polarization Peptide Binding Assay

Polarization experiments were performed on an Analyst HT 96-384 (Molecular Devices Corp.) according to the procedure of Keating, S. M., Marsters, J, Beresini, M., Ladner, C., Zioncheck, K., Clark, K., Arellano, F., and Bodary., S. (2000) in *Proceedings of SPIE: In Vitro Diagnostic Instrumentation* (Cohn, G. E., Ed.) pp 128-137, Bellingham, Wash. Samples for fluorescence polarization affinity measurements were prepared by addition of 1:2 serial dilutions starting at a final concentration of 5 µM of MLXBIR3SG in polarization buffer (50 mM Tris [pH 7.2], 120 mM NaCl, 1% bovine globulins 5 mM DTT and 0.05% octylglucoside) to 5-carboxyflourescein-conjugated AVPdi-Phe-NH₂ (AVP-diPhe-FAM) at 5 nM final concentration.

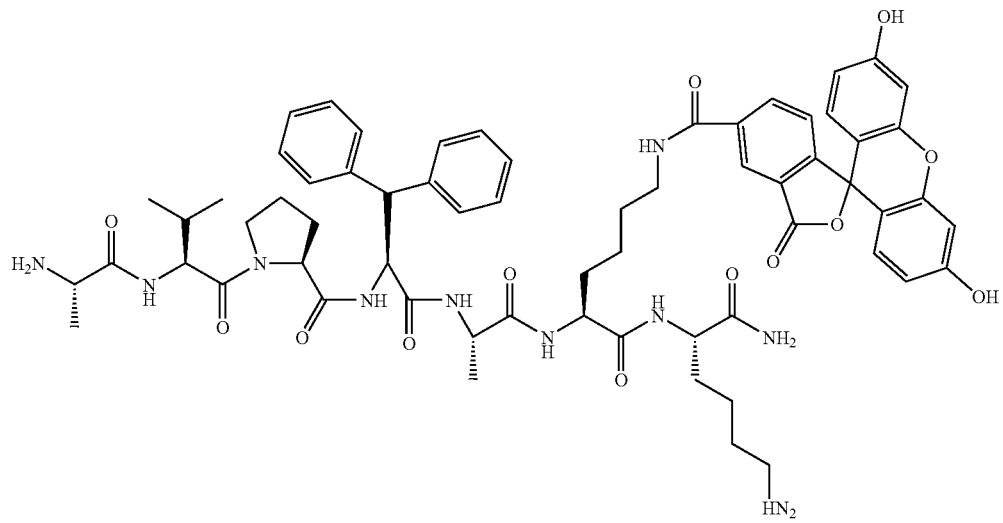

AVP-diPhe-FAM probe

The reactions were read after an incubation time of 10 minutes at room temperature with standard cut-off filters for the fluorescein fluorophore ($\lambda_{ex}$=485 nm; $\lambda_{em}$=530 nm) in 96-well black HE96 plates (Molecular Devices Corp.). Fluorescence values were plotted as a function of the protein concentration, and the IC50s were obtained by fitting the data to a 4-parameter equation using Kaleidograph software (Synergy software, Reading, Pa.). Competition experiments were performed by addition of the MLXBIR3SG at 30 nM to wells containing 5 nM of the AVP-diPhe-FAM probe as well as 1:3 serial dilutions of antagonist compounds starting at a concentration of 300 μM in the polarization buffer. Samples were read after a 10-minute incubation. Fluorescence polarization values were plotted as a function of the antagonist concentration, and the $IC_{50}$ values were obtained by fitting the data to a 4-parameter equation using Kaleidograph software (Synergy software, Reading, Pa.). Inhibition constants ($K_i$) for the antagonists were determined from the $IC_{50}$ values. Compounds of the invention where found to have IAP inhibitory activity which was demonstrated in this assay.

We claim:

1. A method of inducing apoptosis in a cell comprising introducing into said cell a compound a therapeutically effective amount of a compound of formula I:

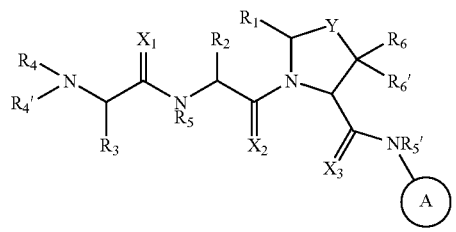

I wherein $X_1$, $X_2$ and $X_3$ are independently O or S;

Y is $(CHR_7)_n$, O or S; wherein n is 1 or 2 and $R_7$ is H, halogen, alkyl, aryl, aralkyl, amino, arylamino, alkylamino, aralkylamino, alkoxy, aryloxy or aralkyloxy;

A is a 5-member heterocycle comprising 1 to 4 heteroatoms optionally substituted with amino, hydroxyl, mercapto, halogen, carboxyl, amidino, guanidino, alkyl, alkoxy, aryl, aryloxy, acyl, acyloxy, acylamino, alkoxycarbonylamino, cycloalkyl, alkylthio, alkylsulfinyl, alkylsulfonyl, aminosulfonyl, alkylaminosulfonyl, alkylsulfonylamino or a heterocycle; wherein each alkyl, alkoxy, aryl, aryloxy, acyl, acyloxy, acylamino, cycloalkyl and heterocycle substitution is optionally substituted with hydroxyl, halogen, mercapto, carboxyl, alkyl, alkoxy, haloalkyl, amino, nitro, cyano, cycloalkyl, aryl or a heterocycle;

$R_1$ is H or $R_1$ and $R_2$ together form a 5-8 member ring;

$R_2$ is alkyl, cycloalkyl, cycloalkylalkyl, aryl, aralkyl, a heterocycle or heterocyclylalkyl; each optionally substituted with hydroxyl, mercapto, halogen, amino, carboxyl, alkyl, haloalkyl, alkoxy or alkylthio;

$R_3$ is H or alkyl;

$R_4$ and $R_4'$ are independently H, hydroxyl, amino, alkyl, aryl, aralkyl, cycloalkyl, cycloalkylalkyl, heteroaryl, or heteroarylalkyl wherein each alkyl, aryl, aralkyl, cycloalkyl, cycloalkylalkyl, heteroaryl and heteroarylalkyl is optionally substituted with halogen, hydroxyl, mercapto, carboxyl, alkyl, alkoxy, amino and nitro;

$R_5$ and $R_5'$ are each independently H or alkyl;

$R_6$, and $R_6'$ are each independently H, alkyl, aryl or aralkyl;

and a pharmaceutically acceptable salt thereof.

2. A method of sensitizing a cell to an apoptotic signal comprising introducing into said cell a compound a therapeutically effective amount of a compound of formula I:

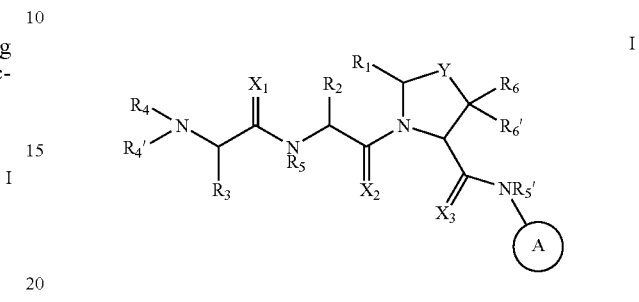

I wherein $X_1$, $X_2$ and $X_3$ are independently O or S;

Y is $(CHR_7)_n$, O or S; wherein n is 1 or 2 and $R_7$ is H, halogen, alkyl, aryl, aralkyl, amino, arylamino, alkylamino, aralkylamino, alkoxy, aryloxy or aralkyloxy;

A is a 5-member heterocycle comprising 1 to 4 heteroatoms optionally substituted with amino, hydroxyl, mercapto, halogen, carboxyl, amidino, guanidino, alkyl, alkoxy, aryl, aryloxy, acyl, acyloxy, acylamino, alkoxycarbonylamino, cycloalkyl, alkylthio, alkylsulfinyl, alkylsulfonyl, aminosulfonyl, alkylaminosulfonyl, alkylsulfonylamino or a heterocycle; wherein each alkyl, alkoxy, aryl, aryloxy, acyl, acyloxy, acylamino, cycloalkyl and heterocycle substitution is optionally substituted with hydroxyl, halogen, mercapto, carboxyl, alkyl, alkoxy, haloalkyl, amino, nitro, cyano, cycloalkyl, aryl or a heterocycle;

$R_1$ is H or $R_1$ and $R_2$ together form a 5-8 member ring;

$R_2$ is alkyl, cycloalkyl, cycloalkylalkyl, aryl, aralkyl, a heterocycle or heterocyclylalkyl; each optionally substituted with hydroxyl, mercapto, halogen, amino, carboxyl, alkyl, haloalkyl, alkoxy or alkylthio;

$R_3$ is H or alkyl;

$R_4$ and $R_4'$ are independently H, hydroxyl, amino, alkyl, aryl, aralkyl, cycloalkyl, cycloalkylalkyl, heteroaryl, or heteroarylalkyl wherein each alkyl, aryl, aralkyl, cycloalkyl, cycloalkylalkyl, heteroaryl and heteroarylalkyl is optionally substituted with halogen, hydroxyl, mercapto, carboxyl, alkyl, alkoxy, amino and nitro;

$R_5$, and $R_5'$ are each independently H or alkyl;

$R_6$, and $R_6'$ are each independently H, alkyl, aryl or aralkyl, and a pharmaceutically acceptable salt thereof.

3. The method of claim 2, wherein said apoptotic signal is induced by contacting said cell with a compound selected from the group consisting of cytarabine, fludarabine, 5-fluoro-2'-deoxyuiridine, gemcitabine, methotrexate, bleomycin, cisplatin, cyclophosphamide, adriamycin (doxorubicin), mitoxantrone, camptothecin, topotecan, colcemid, colchicine, paclitaxel, vinblastine, vincristine, tamoxifen, finasteride, taxotere and mitomycin C.

4. The method of claim 2, wherein said apoptotic signal is induced by contacting said cell with Apo2L/TRAIL.

* * * * *

SEQUENCE LISTING

```
<160> NUMBER OF SEQ ID NOS: 1

<210> SEQ ID NO 1
<211> LENGTH: 133
<212> TYPE: PRT
<213> ORGANISM: Homo sapiens

<400> SEQUENCE: 1

Met Gly Ser Ser His His His His His His Ser Ser Gly Leu Val
 1               5                   10                  15

Pro Arg Gly Ser His Met Leu Glu Thr Glu Glu Glu Glu Glu Glu
                20                  25                  30

Gly Ala Gly Ala Thr Leu Ser Arg Gly Pro Ala Phe Pro Gly Met
                35                  40                  45

Gly Ser Glu Glu Leu Arg Leu Ala Ser Phe Tyr Asp Trp Pro Leu
                50                  55                  60

Thr Ala Glu Val Pro Pro Glu Leu Leu Ala Ala Ala Gly Phe Phe
                65                  70                  75

His Thr Gly His Gln Asp Lys Val Arg Cys Phe Phe Cys Tyr Gly
                80                  85                  90

Gly Leu Gln Ser Trp Lys Arg Gly Asp Asp Pro Trp Thr Glu His
                95                  100                 105
```

```
Ala Lys Trp Phe Pro Gly Cys Gln Phe Leu Leu Arg Ser Lys Gly
            110             115                 120

Gln Glu Tyr Ile Asn Asn Ile His Leu Thr His Ser Leu
                125             130
```